United States Patent
Banerjee et al.

(10) Patent No.: US 8,486,720 B2
(45) Date of Patent: Jul. 16, 2013

(54) ARRAYS OF MAGNETIC PARTICLES

(75) Inventors: Sukanta Banerjee, North Brunswick, NJ (US); Michael Seul, Fanwood, NJ (US); Alice X. Li, Ithaca, NY (US)

(73) Assignee: BioArray Solutions, Ltd., Warren, NJ (US)

( * ) Notice: Subject to any disclaimer, the term of this patent is extended or adjusted under 35 U.S.C. 154(b) by 933 days.

(21) Appl. No.: 10/910,460

(22) Filed: Aug. 3, 2004

(65) Prior Publication Data
US 2005/0272049 A1 Dec. 8, 2005

Related U.S. Application Data

(63) Continuation of application No. 10/204,799, filed as application No. PCT/US01/20179 on Jun. 21, 2001, now Pat. No. 7,892,854.

(60) Provisional application No. 60/213,106, filed on Jun. 21, 2000.

(51) Int. Cl.
*G01N 33/553* (2006.01)
(52) U.S. Cl.
USPC ......... 436/526; 436/518; 436/525; 436/287.2
(58) Field of Classification Search
USPC ............... 436/526, 518, 525; 435/287.2, 526, 435/518, 525
See application file for complete search history.

(56) References Cited

U.S. PATENT DOCUMENTS

| | | | |
|---|---|---|---|
| 3,329,638 A | 7/1967 | Blyth |
| 3,574,614 A | 4/1971 | Carreira |
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |

(Continued)

FOREIGN PATENT DOCUMENTS

| CA | 1248873 | 1/1989 |
|---|---|---|
| DE | 4035714 | 5/1992 |

(Continued)

OTHER PUBLICATIONS

Armstrong et al., "Suspension arrays for high throughput, multiplexed single nucleotide polymorphism genotyping" Cytometry. vol. 40:102-108 (2000).

(Continued)

*Primary Examiner* — Mark Shibuya
*Assistant Examiner* — Pensee Do
(74) *Attorney, Agent, or Firm* — Womble Carlyle Sandridge & Rice LLP

(57) ABSTRACT

The present invention provides a method for the generation of novel libraries of encoded magnetic particles from sub-libraries of by the generation of novel sub-libraries of magnetic nanoparticles and encoded particles. The sub-libraries are functionalized on demand are useful in the formation of arrays. The present invention is especially useful for performing multiplexed (parallel) assays for qualitative and/or quantitative analysis of binding interactions of a number of analyte molecules in a sample.

5 Claims, 30 Drawing Sheets

U.S. PATENT DOCUMENTS

| | | |
|---|---|---|
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally ................. 156/629 |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,498 A * | 3/1995 | Gombinsky et al. ........... 204/464 |
| 5,395,688 A | 3/1995 | Wang et al. ................ 428/327 |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | Van Ness et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. ..................... 435/6 |
| 5,639,606 A | 6/1997 | Willey |
| 5,643,765 A | 7/1997 | Willey |

| Patent No. | Date | Inventor(s) | Ref |
|---|---|---|---|
| 5,648,124 A | 7/1997 | Sutor | 427/475 |
| 5,650,488 A | 7/1997 | O'Hare | |
| 5,650,489 A | 7/1997 | Lam et al. | |
| 5,652,059 A | 7/1997 | Margel | |
| 5,652,107 A | 7/1997 | Lizardi et al. | |
| 5,653,939 A | 8/1997 | Hollis et al. | |
| 5,660,990 A * | 8/1997 | Rao et al. | 435/6.11 |
| 5,667,667 A | 9/1997 | Southern | |
| 5,674,686 A | 10/1997 | Schumm et al. | |
| 5,674,698 A | 10/1997 | Zarling et al. | |
| 5,679,524 A | 10/1997 | Nikiforov et al. | |
| 5,690,894 A | 11/1997 | Pinkel et al. | |
| 5,698,271 A | 12/1997 | Liberti et al. | |
| 5,700,637 A | 12/1997 | Southern | |
| 5,700,897 A | 12/1997 | Klainer et al. | |
| 5,714,340 A | 2/1998 | Sutton et al. | |
| 5,714,521 A | 2/1998 | Kedem et al. | |
| 5,716,852 A | 2/1998 | Yager et al. | |
| 5,722,470 A | 3/1998 | Kedar et al. | |
| 5,723,218 A | 3/1998 | Haugland et al. | |
| 5,723,233 A | 3/1998 | Garza et al. | |
| 5,728,529 A | 3/1998 | Metzker et al. | |
| 5,736,349 A | 4/1998 | Sasaki et al. | |
| 5,744,299 A | 4/1998 | Henrickson et al. | |
| 5,744,305 A | 4/1998 | Fodor et al. | |
| 5,747,349 A | 5/1998 | Van den Engh et al. | |
| 5,751,629 A | 5/1998 | Nova et al. | 365/151 |
| 5,763,175 A | 6/1998 | Brenner | |
| 5,763,198 A | 6/1998 | Hirth et al. | |
| 5,763,263 A | 6/1998 | Dehlinger | |
| 5,766,711 A | 6/1998 | Barmakian | |
| 5,766,963 A | 6/1998 | Baldwin et al. | |
| 5,770,358 A | 6/1998 | Dower et al. | |
| 5,770,367 A | 6/1998 | Southern et al. | |
| 5,770,455 A | 6/1998 | Cargill et al. | |
| 5,770,721 A | 6/1998 | Ershov et al. | |
| 5,773,222 A | 6/1998 | Scott | |
| 5,776,711 A | 7/1998 | Vyas et al. | |
| 5,779,976 A | 7/1998 | Leland et al. | |
| 5,786,219 A | 7/1998 | Zhang et al. | |
| 5,789,147 A | 8/1998 | Rubinstein et al. | |
| 5,792,430 A | 8/1998 | Hamper | |
| 5,800,992 A | 9/1998 | Fodor et al. | |
| 5,807,755 A | 9/1998 | Ekins | |
| 5,812,272 A | 9/1998 | King et al. | |
| 5,814,524 A | 9/1998 | Walt et al. | |
| 5,831,045 A | 11/1998 | Stolowitz et al. | |
| 5,834,590 A | 11/1998 | Vinik et al. | |
| 5,837,501 A | 11/1998 | Beumer et al. | |
| 5,837,551 A | 11/1998 | Ekins | |
| 5,837,832 A | 11/1998 | Chee et al. | |
| 5,840,485 A | 11/1998 | Lebl et al. | |
| 5,843,660 A | 12/1998 | Schumm et al. | |
| 5,844,304 A | 12/1998 | Kata et al. | |
| 5,846,708 A | 12/1998 | Hollis et al. | |
| 5,855,753 A | 1/1999 | Trau et al. | |
| 5,856,092 A | 1/1999 | Dale et al. | |
| 5,858,804 A | 1/1999 | Zanzucchi et al. | |
| 5,866,099 A | 2/1999 | Owen et al. | |
| 5,866,331 A | 2/1999 | Singer et al. | |
| 5,874,219 A * | 2/1999 | Rava et al. | 435/6 |
| 5,876,946 A | 3/1999 | Burbaum et al. | |
| 5,898,071 A | 4/1999 | Hawkins | |
| 5,900,481 A | 5/1999 | Lough et al. | |
| 5,922,617 A | 7/1999 | Wang et al. | 436/518 |
| 5,939,021 A | 8/1999 | Hansen et al. | |
| 5,942,388 A | 8/1999 | Willner et al. | |
| 5,945,525 A | 8/1999 | Uematsu et al. | |
| 5,948,621 A | 9/1999 | Turner et al. | |
| 5,948,627 A | 9/1999 | Lee et al. | |
| 5,952,131 A | 9/1999 | Kumacheva et al. | |
| 5,952,174 A | 9/1999 | Nikiforoy et al. | |
| 5,959,098 A | 9/1999 | Goldberg et al. | |
| 5,961,923 A | 10/1999 | Nova et al. | |
| 5,965,235 A | 10/1999 | McGuire et al. | |
| 5,965,452 A | 10/1999 | Kovacs | |
| 5,968,736 A | 10/1999 | Still et al. | |
| 5,981,176 A | 11/1999 | Wallace | |
| 5,981,180 A | 11/1999 | Chandler et al. | 435/6 |
| 5,988,432 A | 11/1999 | Sun | |
| 5,989,835 A | 11/1999 | Dunlay et al. | |
| 5,993,935 A | 11/1999 | Rasmussen et al. | |
| 5,994,066 A | 11/1999 | Bergeron et al. | |
| 6,001,614 A | 12/1999 | Akhavan-Tafti | |
| 6,004,744 A | 12/1999 | Goelet et al. | |
| 6,007,996 A | 12/1999 | McNamara et al. | |
| 6,013,531 A * | 1/2000 | Wang et al. | 436/526 |
| 6,014,451 A | 1/2000 | Berry et al. | |
| 6,015,664 A | 1/2000 | Henrickson et al. | |
| 6,015,666 A | 1/2000 | Springer et al. | |
| 6,017,696 A | 1/2000 | Heller | |
| 6,018,350 A | 1/2000 | Lee et al. | |
| 6,023,540 A | 2/2000 | Walt et al. | |
| 6,023,590 A | 2/2000 | Abe et al. | |
| 6,025,905 A | 2/2000 | Sussman | |
| 6,027,889 A | 2/2000 | Barany et al. | |
| 6,027,945 A | 2/2000 | Smith et al. | |
| 6,033,547 A | 3/2000 | Trau et al. | |
| 6,043,354 A | 3/2000 | Hillebrand et al. | |
| 6,048,690 A | 4/2000 | Heller | |
| 6,054,270 A | 4/2000 | Southern | |
| 6,060,243 A | 5/2000 | Tang et al. | |
| 6,063,569 A | 5/2000 | Gildea et al. | |
| 6,068,818 A | 5/2000 | Ackley et al. | |
| 6,075,905 A | 6/2000 | Herman et al. | |
| 6,077,669 A | 6/2000 | Little et al. | |
| 6,077,674 A | 6/2000 | Schleifer et al. | |
| 6,080,585 A | 6/2000 | Southern et al. | |
| 6,083,699 A | 7/2000 | Leushner et al. | |
| 6,083,763 A | 7/2000 | Balch | |
| 6,084,991 A | 7/2000 | Sampas | |
| 6,086,736 A | 7/2000 | Dasgupta et al. | |
| 6,090,458 A | 7/2000 | Murakami | |
| 6,090,545 A | 7/2000 | Wohlstadter et al. | |
| 6,090,555 A | 7/2000 | Fiekowsky et al. | |
| 6,090,912 A | 7/2000 | Lebl et al. | |
| 6,096,368 A | 8/2000 | Sun | |
| 6,100,030 A | 8/2000 | Feazel et al. | |
| 6,103,379 A | 8/2000 | Margel et al. | |
| 6,106,685 A | 8/2000 | McBride et al. | |
| 6,120,666 A | 9/2000 | Jacobson et al. | |
| 6,122,599 A | 9/2000 | Mehta | |
| 6,123,263 A | 9/2000 | Feng | |
| 6,124,092 A | 9/2000 | O'Neill et al. | |
| 6,126,731 A | 10/2000 | Kemeny et al. | |
| 6,130,101 A | 10/2000 | Mao et al. | |
| 6,132,685 A | 10/2000 | Kercso et al. | |
| 6,132,997 A | 10/2000 | Shannon | |
| 6,133,436 A | 10/2000 | Koster et al. | |
| 6,136,171 A | 10/2000 | Frazier et al. | |
| 6,136,468 A | 10/2000 | Mitchell, Jr. et al. | |
| 6,139,831 A * | 10/2000 | Shivashankar et al. | 530/351 |
| 6,141,046 A | 10/2000 | Roth et al. | |
| 6,143,499 A | 11/2000 | Mirzabekov et al. | |
| 6,149,789 A | 11/2000 | Benecke et al. | |
| 6,150,095 A | 11/2000 | Southern et al. | |
| 6,151,062 A | 11/2000 | Inoguchi et al. | |
| 6,153,375 A | 11/2000 | Kobylecki et al. | |
| 6,153,389 A | 11/2000 | Haarer et al. | |
| 6,156,502 A | 12/2000 | Beattie | |
| 6,167,910 B1 | 1/2001 | Chow | |
| 6,172,218 B1 | 1/2001 | Brenner | |
| 6,180,226 B1 | 1/2001 | McArdle et al. | 428/332 |
| 6,183,970 B1 | 2/2001 | Okano et al. | |
| 6,187,540 B1 | 2/2001 | Staub et al. | |
| 6,193,866 B1 | 2/2001 | Bader et al. | |
| 6,193,951 B1 | 2/2001 | Ottoboni et al. | |
| 6,200,737 B1 | 3/2001 | Walt et al. | |
| 6,200,814 B1 | 3/2001 | Malmqvist et al. | |
| 6,203,993 B1 | 3/2001 | Shuber et al. | |
| 6,207,369 B1 | 3/2001 | Wohlstadter et al. | |
| 6,209,589 B1 | 4/2001 | Hare | |
| 6,218,111 B1 | 4/2001 | Southern et al. | |
| 6,221,598 B1 | 4/2001 | Schumm et al. | |
| 6,232,066 B1 | 5/2001 | Felder et al. | |
| 6,235,471 B1 | 5/2001 | Knapp et al. | |
| 6,238,863 B1 | 5/2001 | Schumm et al. | |
| 6,245,508 B1 | 6/2001 | Heller et al. | |

| | | |
|---|---|---|
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul ................................ 436/534 |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. ............. 436/523 |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,284,497 B1* | 9/2001 | Sabanayagam et al. ...... 435/91.2 |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1* | 3/2002 | Zhou et al. .................... 436/518 |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauver et al. |
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1* | 10/2006 | Walt et al. ................... 250/459.1 |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. ............. 428/403 |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |

| | | | | | |
|---|---|---|---|---|---|
| 2002/0150909 A1 | 10/2002 | Stuelpnagel et al. | WO | WO 9325563 | 6/1992 |
| 2002/0155481 A1 | 10/2002 | Hirota et al. | WO | WO 9302360 | 2/1993 |
| 2002/0166766 A1 | 11/2002 | Seul et al. | WO | WO 9306121 | 4/1993 |
| 2002/0182609 A1 | 12/2002 | Arcot | WO | WO 9324517 | 12/1993 |
| 2002/0187501 A1 | 12/2002 | Huang et al. | WO | WO 94000810 | 1/1994 |
| 2002/0197728 A1 | 12/2002 | Kaufman et al. | WO | WO 9428028 | 9/1994 |
| 2002/0198665 A1 | 12/2002 | Seul et al. | WO | WO 9509248 | 4/1995 |
| 2003/0003272 A1 | 1/2003 | Laguitton | WO | WO 9512608 | 5/1995 |
| 2003/0004594 A1 | 1/2003 | Liu et al. | WO | WO 9512808 | 5/1995 |
| 2003/0006143 A1 | 1/2003 | Banerjee et al. | WO | WO 9600148 | 1/1996 |
| 2003/0012693 A1 | 1/2003 | Otillar et al. | WO | WO 9602558 | 2/1996 |
| 2003/0012699 A1 | 1/2003 | Moore et al. | WO | WO 9603212 | 2/1996 |
| 2003/0022370 A1 | 1/2003 | Casagrande et al. | WO | WO 9604547 | 2/1996 |
| 2003/0022393 A1 | 1/2003 | Seul et al. | WO | WO 9607917 | 3/1996 |
| 2003/0031351 A1 | 2/2003 | Yim | WO | WO 96/30392 | 10/1996 |
| 2003/0038812 A1 | 2/2003 | Bartell | WO | WO 9630392 | 10/1996 |
| 2003/0040129 A1 | 2/2003 | Shah | WO | WO 9641011 | 12/1996 |
| 2003/0062422 A1 | 4/2003 | Fateley et al. | WO | WO 9714028 | 4/1997 |
| 2003/0077607 A1 | 4/2003 | Hopfinger et al. | WO | WO 9722720 | 6/1997 |
| 2003/0082487 A1 | 5/2003 | Burgess | WO | WO 9739151 | 10/1997 |
| 2003/0082530 A1 | 5/2003 | Soderlund et al. | WO | WO 9740383 | 10/1997 |
| 2003/0082531 A1 | 5/2003 | Soderlund et al. | WO | WO 9740385 | 10/1997 |
| 2003/0082587 A1 | 5/2003 | Seul et al. | WO | WO 9745559 | 12/1997 |
| 2003/0087228 A1 | 5/2003 | Bamdad et al. | WO | WO 9802752 | 1/1998 |
| 2003/0108913 A1 | 6/2003 | Schouten | WO | WO 9804950 | 2/1998 |
| 2003/0129296 A1 | 7/2003 | Kelso | WO | WO 9806007 | 2/1998 |
| 2003/0134326 A1 | 7/2003 | Hansen et al. | WO | WO 9820153 | 5/1998 |
| 2003/0138842 A1 | 7/2003 | Seul et al. | WO | WO 9821593 | 5/1998 |
| 2003/0148335 A1 | 8/2003 | Shen et al. | WO | WO 9838334 | 9/1998 |
| 2003/0152931 A1 | 8/2003 | Chiou et al. | WO | WO 9840726 | 9/1998 |
| 2003/0154108 A1 | 8/2003 | Fletcher-Haynes et al. | WO | WO 98/53093 | 11/1998 |
| 2003/0177036 A1 | 9/2003 | Oka et al. | WO | WO 9853093 | 11/1998 |
| 2003/0182068 A1 | 9/2003 | Battersby et al. | WO | WO 9909217 | 2/1999 |
| 2003/0186220 A1 | 10/2003 | Zhou et al. | WO | WO 9918434 | 4/1999 |
| 2003/0228610 A1 | 12/2003 | Seul | WO | WO 9919515 | 4/1999 |
| 2004/0002073 A1 | 1/2004 | Li et al. | WO | WO 9924822 | 5/1999 |
| 2004/0009614 A1 | 1/2004 | Ahn et al. | WO | WO 9935499 | 7/1999 |
| 2004/0014073 A1 | 1/2004 | Trau et al. | WO | WO 9936564 | 7/1999 |
| 2004/0021073 A1 | 2/2004 | Barbic et al. | WO | WO 9941273 | 8/1999 |
| 2004/0048259 A1 | 3/2004 | Hashmi et al. | WO | WO 9951773 | 10/1999 |
| 2004/0093238 A1 | 5/2004 | Deakter | WO | WO 9960170 | 11/1999 |
| 2004/0106121 A1 | 6/2004 | Ugolin et al. | WO | WO 9967641 | 12/1999 |
| 2004/0132122 A1 | 7/2004 | Banerjee et al. | WO | WO 0003004 | 1/2000 |
| 2004/0137641 A1 | 7/2004 | Holtlund et al. | WO | WO 0004372 | 1/2000 |
| 2004/0175734 A1 | 9/2004 | Stahler et al. | WO | WO 0007019 | 2/2000 |
| 2004/0219520 A1 | 11/2004 | Mirkin et al. | WO | WO 0013004 | 3/2000 |
| 2004/0229269 A1 | 11/2004 | Hashmi et al. | WO | WO 0020593 | 4/2000 |
| 2005/0048570 A1 | 3/2005 | Weber et al. | WO | WO 0022172 | 4/2000 |
| 2005/0112585 A1 | 5/2005 | Zichi et al. | WO | WO 0026920 | 5/2000 |
| 2005/0143928 A1 | 6/2005 | Moser et al. | WO | WO 0031356 | 6/2000 |
| 2005/0239098 A1 | 10/2005 | Hastings et al. | WO | WO 0039587 | 7/2000 |
| 2006/0024732 A1 | 2/2006 | Huang et al. | WO | WO 0046602 | 8/2000 |
| 2006/0035240 A1 | 2/2006 | Seul et al. | WO | WO 0051058 | 8/2000 |
| 2006/0275799 A1 | 12/2006 | Banerjee et al. | WO | WO 0062048 | 10/2000 |
| 2007/0031877 A1 | 2/2007 | Stahler et al. | WO | WO 0073777 | 12/2000 |
| 2007/0231810 A1 | 10/2007 | Todd et al. | WO | WO 0075373 | 12/2000 |
| 2007/0243534 A1 | 10/2007 | Seul et al. | WO | WO 0101184 | 1/2001 |
| 2008/0020374 A1 | 1/2008 | Greene et al. | WO | WO 0120179 | 3/2001 |
| 2008/0123089 A1 | 5/2008 | Seul et al. | WO | WO 0136679 | 5/2001 |
| 2008/0200349 A1 | 8/2008 | Wu et al. | WO | WO 0154813 | 8/2001 |
| 2008/0214412 A1 | 9/2008 | Stahler et al. | WO | WO 0156216 | 8/2001 |
| 2008/0261205 A1 | 10/2008 | Denomme | WO | WO 0184150 | 11/2001 |
| 2010/0062518 A1 | 3/2010 | Banerjee | WO | WO 0188535 | 11/2001 |
| | | | WO | WO 0194947 | 12/2001 |
| FOREIGN PATENT DOCUMENTS | | | WO | WO 0198765 | 12/2001 |
| EP | 0126450 | 11/1984 | WO | WO 0212888 | 2/2002 |
| EP | 179039 | 4/1986 | WO | WO 0214864 | 2/2002 |
| EP | 246864 | 11/1987 | WO | WO 0231182 | 4/2002 |
| EP | 269764 | 6/1988 | WO | WO 0233084 | 4/2002 |
| EP | 472990 | 3/1992 | WO | WO 0235441 | 5/2002 |
| EP | 478319 | 4/1992 | WO | WO 0237209 | 5/2002 |
| EP | 0529775 | 3/1993 | WO | WO 02057496 | 7/2002 |
| EP | 1394270 | 3/2004 | WO | WO 02058379 | 7/2002 |
| EP | 1564306 | 2/2005 | WO | WO 02061121 | 8/2002 |
| JP | 62265567 | 11/1987 | WO | WO 02079490 | 10/2002 |
| WO | WO 8911101 | 5/1989 | WO | WO 02084285 | 10/2002 |
| WO | WO 9109141 | 6/1991 | WO | WO 02096979 | 12/2002 |
| WO | WO 9119023 | 12/1991 | WO | WO 03020968 | 3/2003 |
| WO | WO 9210092 | 6/1992 | WO | WO 03025011 | 3/2003 |

| | | |
|---|---|---|
| WO | WO 03034029 | 4/2003 |
| WO | WO 03/058196 A2 | 7/2003 |
| WO | WO 03058196 | 7/2003 |
| WO | WO 03079401 | 9/2003 |
| WO | WO 0392546 | 11/2003 |
| WO | WO 04035426 | 4/2004 |
| WO | WO 05000236 | 1/2005 |
| WO | WO 05042763 | 5/2005 |
| WO | WO 05045059 | 5/2005 |
| WO | WO 05095650 | 10/2005 |
| WO | WO 0840257 | 4/2008 |
| WO | WO 0988893 | 7/2009 |
| WO | WO 1025002 | 3/2010 |
| WO | WO 1026038 | 3/2010 |
| WO | WO 1098765 | 9/2010 |
| WO | WO 10143678 | 12/2010 |

OTHER PUBLICATIONS

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B. -Y. Ha et al., "Counterion-Mediated Attraction between Two Like-Charged Rods, " Physical Review Letters, Aug. 18, 1997, vol. 79, No. 7, pgs. 1289-1292.

A. Hatch, et al., "Diffusion Immunoassay in Polyacrylamide Hydrogels". Micro Total Analysis Systems, pp. 571-572 (2001).

Aho et al., "Efficient String Matching: an Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369 - 375 (May 2006).

Albrecht et al., "Photo and electropatterning of hydrogel-encapsulated living cell arrays", Lab on a Chip, vol. 5, Issue 1, pp. 111-118 (2004).

Alford, R. L., "DNA Analysis in forensics, disease and animal/plant identification". Current Opinions in Biotechnology, vol. 5(1), pp. 29 - 33 (1994).

Al-Soud, W. A., "Purification and Characterization of PCR-Inhibitory Components in Blood Cells". Journal of Clinical Microbiology, vol. 39, No. 2, pp. 485 - 493 (Feb 2001).

Al-Soud, W. A., et al., "Identification and characterization of immunoglobulin G in blood as a major inhibitor of diagnostic PCR". Journal of Clinical Microbiology, vol. 38, No. 1, pp. 345 - 350 (Jan 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94 - 98.

Zhang, Y., et al., "Reproducible and inexpensive probe preparation for oligonucleotide arrays". Nucleic Acids Research, vol. 29, No. 13, pp. E66-6 (Jul. 1, 2001).

Arenko, et al., "Protein microchips: Use for immunoassay and enzymatic reactions". Analytical Biochemistry, vol. 278, pp. 123 - 131 (2000).

Assie et al., Correlation between low/high affinity ratios for 5-Ht Receptors and Intrinsic Activity, European Journal of Pharmacology, vol. 386, pp. 97 - 103 (1999).

Bakewell et al., "Characterization of the dielectrophoretic movement of DNA in microfabricated structures", Institute of Physics Conference Series (1999) Electrostatics (1999).

Balass et al. "Recovery of high-affinity phage from a Nitrostretavidin matrix in phage-display technology". Analytical Biochemistry. vol. 243: 264-269 (1996).

Baldwin, et al., "Phosphorylation of gastrin-17 by epidermal growth factor-stimulated tyrosine kinase". Nature, vol. 44, pp. 2403 - 2404 (1998).

Bandeira-Melo, C., et al., "EliCell: a gel-phase dual antibody capture and detection assay to measure cytokine release from eosinophils". Journal of Immunological Methods, vol. 244, pp. 105-115 (2000).

Bao, Y. P., et al., "Detection of Protein Analytes via Nanoparticle-Based Bio Bar Code Technology". Anal. Chem., vol. 78, pp. 2055 - 2059 (2006).

Barany, Francis, "Genetic Disease Detection and DNA Amplification using Cloned Thermostable Ligase". Proceedings of the National Academy of Sciences of the United States of America, vol. 88, pp. 189 - 193 (Jan. 1991).

Barnard et al. "A fibre-optic chemical sensor with descrete sensing sites". Nature, vol. 353:338-340 (1991).

Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481 - 488 (1997).

Battersby et al., "Toward Larger Chemical Libraries: Encoding with Fluorescent Colloids in Combinatorial Chemistry". J. Amer Chem Soc, vol. 122, pp. 2138 - 2139 (2000).

Baumgarth N. et al., a practical approach to multicolor flow cytometry for immunophenotyping, J. Immunological Methods, 2000, pp. 77-97, vol. 243.

Bavykin, S. G., et al., "Portable system for microbial sample preparation and oligonucleotide microarray analysis". Appl. Environmental Microbiol. 67(2), 922-928 (2001).

Beatty et al. "Probability of Finding HLA-mismatched Related or Unrelated Marrow or Cord Blood Donors", Human Immunology, 2001, vol. 61, pp. 834 - 840.

Beebe et al., "Functional Hydrogel structures for autonomous flow control inside microfluidic channels". Nature, vol. 404, No. 6778, pp. 588 - 590 (Apr. 6, 2000).

Beiboer, S. W., et al., "Rapid genotyping of blood group antigens by multiplex polymerase chain reaction and DNA microarray hybridization" 45 Transfusion 667-679 (2005).

Bennett, P. R., et al., "Prenatal Determination of Fetal RhD Type by DNA Amplification". The New England Journal of Medicine, vol. 329, No. 9, pp. 607 - 610 (Aug. 26, 1993).

Bernard, Philip S., "Homogenous Multiplex Genotyping of Hemochromatasis Mutations with Fluorescent Hybridization Probes". American Journal of Pthology, vol. 153, No. 4, pp. 1055 - 1061 (1998).

Bessetti, J., "An introduction to PCT Inhibitors". Profiles in DNA-PCR Inhibition, pp. 9 - 10 (Mar. 2007).

Bickel, P. J., "Discussion of the Evaluation of Forensic DNA Evidence". Proc. Natl. Acad. Sci., vol. 94, p. 5497 (May 1997).

Zhang, X., et al., "Strand invasion by mixed base PNAs and a PNA-peptide chimera". Nucleic Acids Research, vol. 28, No. 17, pp. 3332 - 3338 (2000).

Blaaderen, et al., "Synthesis and Characterization of Colloidal Dispersions of Fluorescent, Monodisperse Silica Spheres". Langmuir, vol. 8, No. 2, pp. 2921 - 2931 (1992).

Bonnet, G., et al., "Thermodynamic basis of the enhanced specificity of structured DNA probes," Proc. Natl. Acad. Science, USA, vol. 96, pp. 6171-6176, May 1999.

Bos et al., "Controlled release of pharmaceutical protein from hydrogels". Business Briefing: Pharmatech, pp. 184 - 187 (2002).

Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).

Boyd et al., "Tosyl Chloride activation of a rayon/polyester cloth for protein immobilization", Biotechnology Techniques, Apr. 1993, vol. 7, 4:277-282.

Braga et al., "Hydrophobic Polymer Modification with Ionic Reagents: Polysterene Staining with Water-Soluble Dyes". Langmuir, vol. 19, No. 18, pp. 7580 - 7586 (2003).

Breslauer, K. J. et al., "Predicting DNA duplex stability from the base sequence". PNAS USA, vol. 83, pp. 3746-3750 (1986).

Broude et al., "Multiplex allele-specific target amplification based on PCR suppression". PNAS. vol. 98, No. 1, pp. 206-211 (2001).

Brown, Patrick O., et al., "Exploring the new world of the genome with DNA microarrays". Nature Genetics Supplement, vol. 21, pp. 33 - 37 (Jan 1999).

Buck et al., "Design Strategies and Performance of Custom DNA Sequence Primers". BioTechniques, vol. 27, pp. 528 - 536 (Sep. 1999).

Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355 - 367 (Nov. 1995).

Bunce, M., et al., "Comprehensive serologically equivalent DNA typing for HLA-A by PCR using sequence specific primers (PCR_SSP)", Tissue Anitigens 45 : 81-90 (1995).

Burbulis, I, et al., "Using protein-DNA chimeras to detect and count small Numbers of molecules". Nature Methods, vol. 2, No. 1, pp. 31 - 37 (Jan 2005).

Cal et al., "Flow cytometry-based minisequencing: A new platform for high-throughput single-nucleotide polymorphism scoring", Genomics 66:135-143 (2000).

Campbell, C. J., et al., "Cell Interaction Microarray for Blood Phenotyping". Analytical Chemistry, vol. 78, pp. 1930 - 1938 (2006).

Campian et al. Colored and fluorescent solid supports. Innovation and Perspectives in Solid Phase Synthesis. Ed: E. Birmingham (Mayflower, London), pp. 469-474 (1994).

Cao et al., "High and intermediate resolution DNA typing systems for class I HLA-A, B, C genes by hybridization with sequence-specific oligonnucleotide probes (SSOP)", Rev Immunogenetics 1:177-208 (1999).

Cao et al., "Nanoparticles with Raman Spectroscopic Fingerprints for DNA and RNA Detection", Science 197:1536-1539 (2002).

Caruso et al., "Magnetic Core-Shell Particles: Preparation of Magnetite Multilayers on Polymer Latex Microspheres". Advanced materials, vol. 11, No. 11, pp. 950 - 953 (1999).

Caruso, et al., "Magnetic Nanocomposite Particles and Hollow Spheres Constructed by a Sequential Layering Approach". Chem Mater, vol. 13, No. 1, pp. 109 - 116 (2001).

Caruso. "Nanoengineering of Particle Surfaces". Advanced Materials, vol. 12, No. 1, pp. 11 - 22 (2001).

Casnellie J E, et al., "Phosphorylation of synthetic peptides by a tyrosine protein kinase from the particulate fraction of a lymphoma cell line". Proc natl Sci USA, vol. 79, No. 2, pp. 282 - 286 (1982).

Chalmers, et al., "An instrument to determine the magnetophoretic mobility of labeled, biological cells and paramagnetic particles". Journal of Magnetism and Magnetic Materials, vol. 194, pp. 231 - 241 (1999).

Chan et al. (1995). The Bipohysics of DNA Hybridization with Immobilized Oligonucleotide Probes. Biophysical Journal 69:2243-2255.

Chang, et al., "New Approach to Produce monosized Polymer Microcapsules by the Solute Co-diffusion Method". Langmuir, vol. 17, No. 18, pp. 5435 - 5439 (2001).

Zhang et al., "Reconstruction of DNA sequencing by hybridization". Bioinformatics, vol. 19, No. 1, pp. 14 - 21 (2003).

Chaudhry et al., "Reactivity of human apurinic/apyrimidinic endonuclease and Escheria coli exonucleonase III with bistranded abasic sites in DNA". The Journal of Biological Chemisty., vol. 272: 15650 - 15655 (1997).

Chee, M. et al., "Accessing genetic information with high-density DNA arrays". Science, vol. 274, pp. 610-613 (1996).

Chen et al., "A Microsphere-Based assay for multiplexed single nucleotide polymorphism analysis using single base chain extension", Genome Research, Cold Spring Harbor Laboratory Press 10:549-557 (2000).

Zhang et al., "Nuclear DNA analysis in genetic studies of populations; practice, problems and prospects" Molecular Ecology. vol. 12:563-584 (2003).

Chen, Y X, et al., "Deletion of arginine codon 229 in the Rhce gene alters e and f but not c antigen expression". vol. 44, No. 3, pp. 391-398 (Mar. 2004).

Cheng, et al., "A Synthetic peptide derived from p34cdc2 is a Specific and Efficient Substrate of SRC-Family Tyrosine Kinases". J Biol Chem, pp. 9248 - 9256. vol. 267, No. 13 (1992).

Zborowski, et al., "Continuous cell separation using novel magnetic quadruple flow sorter". Journal of Magnetism and Magnetic Materials, vol. 194, pp. 224 - 230 (1999).

Cherepinsky, Vera, "On mathematical aspects of genomic analysis", Ph.D. Thesis, published Mar. 2004.

Cheung, V. G., et al., "Making and Reading Microarrays". vol. 21, pp. 15 - 19 (Jan 1999).

Choi, et al., "An on-chip magnetic separator using spiral electromagnets with semi-encapsulated permalloy". Biosensors & Bioelectronics, vol. 16, pp. 409 - 416 (2001).

Yellen, B. B., et al., "Programmable Assembly of Colloidal Particles Using Magnetic Microwell Templates". Langmuir, page est 6.5 (2004).

Clerc, P., et al., "Advanced deep reactive ion etching: a versatile tool for microelectromechanical systems". J. Micromech Microeng, vol. 8, No. 4, pp. 272 - 278 (Dec. 1998).

Coffer et al., "Characterization of Quanum-Confined CdS Nanocrystallites Stabilized by Deoxyribonucleic Acid (DNA)" Nanotechnology, 1992 3:69-75.

Yeh, S. R., et al., "Assembly of ordered colloidal aggregares by electric-field-induced fluid flow". Nature, Mar 6, 1997; vol. 386, No. 6620, pp. 57 - 59.

Colombie, et al., "Role of Mixed Anionic-Nonionic Systems of Surfactants in the Emulsion Polymerization of Styrene: Effect on Particle Nucleation". Macromolocules. vol. 33, No. 20, pp. 7283 - 7291 (2000).

Cosgrove et al. "A Small-angle neutron scattering study of the structure of gelatin at the surface of polystyrene latex particles". Langmuir. vol. 14:5376-5382 (1998).

Coyne et al., "Assymetric PCR for ssDNA Production", Molecular Biology Techniques Manual. Third Edition. Jan. 1994, Feb. 2001; http://www.mcb.uct.ac.za/pcrcond.htm.

Crisp, M., et al., "Preparation of Nanoparticle Coatings on Surfaces of Complex Geometry". Nano Letters, vol. 3, No. 2, pp. 173 - 177 (2003).

Cronin M. T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).

Cruse et al., "Illustrated Dictionary of Immunology". Boca Raton: CRC Press, p. 512 (2003).

Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138 - 1143 (2001).

Dasgupta, et al., "Flow of multiple fluids in a small dimension". Analytical Chemistry, vol. 74, No. 7, pp. 208 - 213 (2002).

De Farias, P., et al., Investigation of red blood cell antigens with highly fluorescent and stable semiconductor quantum dots, J. Bimedical Optics, 2005, pp. 1-4, vol. 10(4).

Decher, G., "Fuzzy Nanoassemblies: Toward Layered Polymeric Multicomposites". Science, vol. 277, pp. 1232 - 1237 (Aug 29, 1997).

Denomme, G. A., et al., "High throughput multiplex single-nucloetide polymorphism analysis for red cell and platelet antigen genotypes". Transfusion, vol. 45, pp. 660 -666 (May 2005).

Denkov et al. "Mechanism of Formation of Two-Dimensional Crystals from Latex Particles on Substrates," langmuir, 1992, pp. 3183-3190, vol. 8.

Ding et al., "Direct molecular haplotyping of long-range genomic DNA with M1-PCR", Jun. 2003, vol. 100, 13: 7449 - 7453.

Du et al., "Sensitivity and Specificity of Metal Surface-Immobilized," Molecular Beacon, Biosensors; JACS 2005, vol. 127, No. 21, pp. 7932-7940.

Duggan, David J., et al., "Expression profiling using cDNA microarrays". Nature Genetics Supplement, vol. 21, pp. 10 - 14 (Jan 1999).

Dunbar S A et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.

Duquesnoy HLA Matchmaker: a Molecularly Based Algorithm for Histocompatibility Determination. I. Description of the Algorithm. Human Immunology, vol. 63, pp. 339-352 (2002).

Dziennik, S. R., et al., "Nondiffusive mechanisms enhance protein uptake rates in ion exchange particles". PNAS, vol. 100, no. 2, pp. 420-425 (2003).

Easteal, S. "DNA Fingerprinting by PCR Amplification of HLA Genes". DNA and Criminal Justice. 1991; Human Genetics Group, John Curtin School of Medical Research, pp. 121 - 127.

Egner et al. "Tagging in combinatorial chemistry: the use of coloured and fluorescent beads". Chem. Commun. pp. 735-736 (1997).

Elaissari et al., "Hydrophilic and cationic latex particles for the specific extraction of nucleic acids". J. Biomater, Sci Polymer Edn, vol. 10, pp. 403 - 420 (1999).

Erdogan et al., "Detection of mitochondrial single nucleotide polymorphisms using a primer elongation reaction on oligonucleotide microarrays", Nucleic Acid Research, 29 : 1-7 (2001).

Ericsson, O., et al., "A dual-tag microarray platform for high-performance nucleic acid and protein analyses". Nucleic Acids Research, vol. 36, No. 8 e45, pp. 1 - 9 (2008).

Erlich, et al., "HLA DNA Typing and Transplantation", Immunity, 14: 347 - 356 (2001).

Fan et al., "Parallel Genotyping of Human SNPs Using Generic High-density Oligonucleotide Tag Arrays", Genome Research, vol. 10, pp. 853 - 860 (2000).

Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).

Ferguson et al., "High-Density Fiber-Optic DNA Random Microsphere Array". Anal. Chem, vol. 72, pp. 5618 - 5624 (2000).

Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598 - 1603 (2001).

Finkel, et al. "Barcoding the Microworld". Analytical Chemistry, pp. 353 - 359 (Oct. 1, 2004).

Fitch, J. P. et al., "Rapid Development of Nucleic Acid Diagnostics", Proceedings of the IEEE 90 (11): 1708-1720 (Nov. 2002).

Fluorescent Microspheres (Tech. Note #19). Bangs Laboratories (1997).

Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767 - 773 (Feb 15, 1991).

Fowke, Keith R., et al. "Genetic analysis of human DNA recovered from minute amounts of serum or plasma". Journal of Immunological Methods, vol. 80, pp. 45-51 (1995).

Frengen, Jomar, et al., "Demonstration and Minimization of Serum Interference in Flow Cytometric Two-Site Immunoassays". Clinical Chemistry, vol. 40, No. 3, pp. 420 - 425 (1994).

Fuh et al. Single Fibre Optic Fluorescence pH Probe. Analyst, 112:1159-1163 (1987).

Fuh et al., "A Method for Determination of Particle Magnetic Susceptibility with Analytical Magnetapheresis". Anal. Chem, vol. 72, pp. 3590 - 3595 (2000).

Fulton et al. "Advanced multiplexed analysis with the FlowMetrix system". Clinical Chemistry, vol. 43:9, pp. 1749-1756 (1997).

Gahan, P. B., "Circulating Nucleic Acid in Plasma and Serum: Diagnosis and Prognosis in Cancer". Oncology, vol. 32, No. 6, pp. 20 - 22 (Oct. 2008); Weekly news updates on www.cli-online.com.

Gates, et al., "Photonic Crystals that can be Addressed with an External Magnetic Field". Adv Mater, vol. 13, No. 21, pp. 1605 - 1608 (2001).

Gelfi, C., et al., "Investigation of the Properties of Novel Acrylamido Monomers by Capilary Zone Electrophoresis", Journal of Chromatography, vol. 608, pp. 333-341 (1992).

Gerlach. Human Lymphocyte Antigen Molecular Typing. Archives of Pathology & Laboratory Medicine. vol. 126, pp. 281-284 (2002).

Ghazaly, et al., "Synthesis and Characterization of a Macromonomer Crosslinker". Journal of Applied Polymer Science, vol. 77, pp. 1362 - 1368 (2000).

Ghosh et al. "Covalent attachement of oligonucleotides to solid supports". Nucleic Acids Research. vol. 16, No. 13; pp. 5363-5371 (1987).

Ghosh, P., et al., " a Simple Lithographic Approach for Preparing Patterned, Micron-Scale Corrals for Controlling Cell Growth". Angew. Chem. Int. Ed., vol. 38, No. 11, pp. 1592-1595 (1999).

Giorgi, R., et al., "Nanotechnologies for Conservation of Cultural Heritage: Paper and Canvas Deacidification". Langmuir, vol. 18, pp. 8198 - 8203 (2002).

Good, L., et al., "Bactericidal antisense effects of peptide-DNA conjugates". Nature Biotechnology, vol. 19, pp. 360 - 364 (2001).

Goodey et al., "Development of multianalyte sensor arrays composed of chemically derivatized polymeric microspheres localized in micromachined cavitites". Journal of American Chemical Society, vol. 123, pp. 2559 - 2570 (2001).

Graf et al., "A general method to coat colloidal particles with silica". Langmuir, vol. 19, pp. 6693 - 6700 (2003).

Grazia et al. In-vivo biomedical monitoring by fiber-optic system. Journal of Lightwave Technology. 13, 1396-1406 (1995).

Yellen, et al., "Statistical Analysis of Weakest Link in Chains of Magnetic Particle Carriers for Applications in Printing Biochemical Arrays". European Cells and Materials, vol. 3, pp. 88 - 91 (2002).

Grondahl, et al., "Encoding Combinatorial Libraries: A Novel Application of Fluorescent Silica Colloids". Langmuir, vol. 16, No. 25, pp. 9709 - 9715 (2000).

Gruttner, et al., "New types of silica-fortified magnetic nanoparticles as tools for molecular biology applications". Journal of Magnetism and Magnetic Materials, vol. 94, pp. 8 - 15 (1999).

Gubin et al., "Identification of the Dombrock blood group glycoprotein as a polymorphic member of the ADP-ribosyltransferase gene family", Blood, Oct. 1, 2000, vol. 96, No. 7, pp. 2621-2627.

Gullberg, M., et al., "Cytokine detection by antibody-based proximity ligation". PNAS, vol. 101, No. 22, pp. 8420 - 8424 (Jun. 2004).

Guo, Zhen et al. "Oligonucleotide arrays for high-throughput SNPs detection in the MHC class I genes: HLA-B as a model system". Genome Research; vol. 12, No. 3, pp. 447-457 (Mar. 2002).

Guo, Zhen, "Direct fluorescence analysis of genetic polymorphisms . . .oligonucleotide arrays on glass supports". Nucleic Acids Research, Jul. 1994, Oxford Univ Press, pp. 5456 - 5465.

Gupta et al. ("Hydrogels: from controlled release to pH-responsive drug delivery" Drug Discov Today. May 15, 2002;7(10):569-79.

Gustafsdottir, S. M., "In vitro analysis of DNA - protein interactions by proximity ligation". PNAS, vol. 104, No. 9, pp. 3067 - 3072 (Feb. 2007).

Haab et al. Single Molecule Fluorescence Burst Detection of DNA Fragments Separated by Capillary Electrophoresis. Analytical Chemistry, vol. 67 (No. 18) : 3253-3256 (1995).

Hacis et al., "Resequencing and mutational analysis using oligonucleotide microarrays", Nature America; 21 : 42-47 (1999).

Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581 - 5585 (1998).

Hashimi et al., "A Flexible Array format for large-scale, rapid blood group DNA typing". Transfusion, Published Online Apr. 6, 2004, vol. 45, Issue 5, pp. 680 - 688 (May 2005).

Hashmi, G., et al, "Determination of 24 minor red blood cell antigens for more than 2000 blood donors by high-throughput DNA analysis". Transfusion, vol. 47, No. 4, pp. 736-747 (Apr. 2007).

Zaer, Farid, et al., "Antibody Screening by Enzyme-Linked Immunosorbent Assay Using Pooled Soluble HLA in Renal Transplant Candidates". Transplantation, vol. 63, No. 1, pp. 48 - 51 (Jan 15, 1997).

Heinrich, et al., "Interleukin-6-type Cytokine Signaling through the gp 130/Jak/STAT pathway". Biochem J, vol. 334, pp. 297 - 314 (1998).

Helgesen, et al., "Aggregation of magnetic microspheres: experiements and simulations". Physical Review Letters, vol. 61, No. 15, pp. 1736 - 1739 (1998).

Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515 - 523 (1990).

Yershov et al., "DNA analysis and diagnostics on oligonulceotide microchips". Proceedings of the National Academy of Sciences of the United States of America, vol. 93, No. 10, pp. 4913 - 4918 (May 14, 1996).

Hiller, J., et al., "Reversibly erasable nanoporous anti-reflection coatings from polyelectrolyte multilayers". Nature Materials, vol. 1, pp. 59 - 63 (Sep 2002).

Hirata, H., et al., "Caspases Are Activated in a Branched Protease Cascade and Control Distinct Downstream Processes in Fas-induced Apoptosis". J. Exp. Med., vol. 187, No. 4, pp. 587 - 600 (1998).

Hizume, et al., "Tandem repeat DNA localizing on the proximal DAPI bands of chromosomes in Larix, pinaceae". Genome, vol. 45, pp. 777 - 783 (2002).

Holtz, J., et al., "Intelligent Polymerized Crystalline Colloidal Array: Novel Sensor Materials", Analytical Chemistry, vol. 70, No. 4, pp. 780 - 791 (1998).

Houghton. "General method for the rapid solid-phase synthesis of large numbers of peptides: specificity of anitgen-antibody interaction at the level of individual amino acids". Proc. Natl. Avad. Sci. USA. vol. 82:5131 - 5135 (1985).

Huff et al., "Technical Milestone: Development of the Logical Observation Identifier Names and Codes (LOINC) Vocabulary". JAIMA, vol. 5, pp. 276 - 292 (1998).

Iannone, Marie A., et al., "Multiplexed Single Nucleotide Polymorphism Genotyping by Oligonucleotide Ligation and Flow Cytometry". Cytometry, vol. 39, Issue 2, pp. 131 - 140 (Feb. 17, 2000).

Ide et al., "Synthesis and damage specificity of a novel probe for the detection of abasic sites in DNA". Biochemistry. vol. 32: 8276 - 8283 (1993).

Ito, Y., et al., "Patterned Immobilization of Thermoresponsive Polymer", Langmuir, vol. 13, pp. 2756 - 2759 (1997).

Iwayama, et al., "Optically Tunable Gelled Photonic Crystal Covering Almost the Entire Visible Light Wavelength Region", Langmuir (2002).

Jackman, R. J., et al., "Using Elastomeric Membranes as Dry Resists and for Dry Lift-Off", Langmuir, vol. 15, pp. 2973 - 2984 (1999).

Jeon, N. L., et al., "Patterned polymer growth on silicon surfaces using microcontact printing and surface-initiated polymerization", Applied Physics Letters, vol. 75, No. 26, pp. 4201 - 4203 (1999).

John C. Guatelli et al., "Isothermal, in vitro amplification of nucleic acids by a multienzyme reaction modeled after retroviral replication, " Proc. Nat'l Academy of Science USA, vol. 87: pp. 1874-1878 (1990).

Johnson, K. L., et al., "Surface Energy and the Contact of Elastic Solids". Proceedings of the Royal Society of London, Series A, Mathematical and Physical Sciences, vol. 324, No. 1558, pp. 301 - 313 (Sep 8, 1971).

Jones et al., "Constraint, Optimization, and Hierarchy: Reviewing Stereoscopic Correspondence of Complex Features". Computer Vision and Image Understanding, vol. 65, No. 1, pp. 57 - 78 (1997).

Jones et al., "Dielectrophoretic liquid actuation and nanodroplet formation", Journal of Applied Physics, vol. 89, No. 2, pp. 1441-1448 (Jan 15, 2001).

Kakabakos et al. "Immobilization of Immunoglobulins onto Surface-treated and Untreated Polystyrene Beads for Radioimmunoassays" Clin. Chem. 36 (1990), 492-496.

Kalinina, O., et al., "A core-shell Approach to Producing 3D Polymer Nanocomposites", Macromolecules, vol. 32, pp. 4122 - 4129 (1999).

Kamholz, et al., "Optical measurement of transverse molecular diffusion in a microchannel". Biophysical Journal, vol. 80, pp. 1967 - 1972 (2001).

Kamm, R. C., et al. "Nucleic Acid Concentrations in Normal Human Plasma". Clinical Chemistry, vol. 18, pp. 519 - 522 (1972).

Kandimalla et al., "Cyclicons" as Hybridization-Based Fluorescent Primer-Probes: Bioorganic & Medicinal Chemistry 8 (2000) 1911 to 1916.

Kelly, J. J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).

Klintschar, et al., "Genetic variation at the STR loci D12S391 and CSF1PO in four populations from Austria, Italy, Egypt and Yemen". Forensic Sci. Int. vol. 97:37-45 (1998).

Kim, E., et al., "Polymer microstructures formed by moulding in capillaries", Nature, vol. 376, pp. 581 - 584 (1995).

Knipper, et al., Accession No. AF221125.1.1 on Electronic Database at NCBI (Feb. 16, 2000).

Koch et al., "PNA-Peptide Chimerae". Tetrahedron Letters, vol. 36, pp. 6933 - 6936 (1995).

Koh, et al., "Molding of Hydrogel Microstructures to Create Multiphenotype Cell Microarrays". Analytical Chemistry (2003).

Koh, et al., "Poly(ethylene glycol) Hydrogel Microstructures Encapsulating Living Cells". Langmuir, vol. 18, pp. 2459-2462 (2002).

Kolch. "Meaningful Relationships: the Regulation of the Ras/Raf/MEK/ERK pathway by protein interactions". Biochem J, vol. 351, pp. 289 - 305 (2000).

Kotov, N., et al., "Layer-by-Layer Self-Assembly of Polyelectrolyte-Semicondictor Nanoparticle Composite Films". J. Phy Chem, vol. 99, pp. 13065 - 13069 (1995).

Krausa et al. "A Comprehensive PCR-ssP typing system for identification of HLA-A locus alleles", Tissue Antigens, 47 (3) : 237 - 244 (1996).

Krsko, P., et al., "Electron-Beam Surface Patterned Poly(ethylene glycol) Microhydrogels". Langmuir, vol. 19, pp. 5618 - 5625 (2003).

Krutzik P. O. et al., "Fluorescent cell barcoding in flow cytometry allows high-throughput drug screening and signal profiling". Nature Methods, vol. 3, No. 5, pp. 361-368 (2006).

Kubo et al., "A Novel Sensitive and specific assay for abasic sites, the most commonly produced DNA lesion". Biochemistry, vol. 13: 3703 - 3708 (1992).

Kumacheva, E., et al., "Three-dimensional Arrays in Polymer Nanocompositites", Advanced Materials, vol. 11, No. 3, pp. 231 - 234 (1999).

Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325 - 332 (2001).

Vorlop, K. D., et al., "Entrapment of Microbial Cells within Polyurethane Hydrogel Beads with the Advantage of Low Toxicity", Biotechnology Techniques, vol. 6, No. 6, pp. 483 - 488 (1992).

Kwoh et al., "Transcription based amplification system and detection of amplified human immunodeficiency virus type 1 with a bead-based sandwich hybridization format". Proc. Natl. Acad. Sci, vol. 86, pp. 1173 - 1177 (Feb 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604 - 615 (2000).

Lagerholm et al., "Theory for Ligand Rebinding at Cell Membrane Surfaces," Biophysical Journal (1998), vol. 74, pgs. 1215-1228.

Lamb, D. J., et al., "Modification of Natural and Artificial Polymer Colloids by Topology-Controlled Emulsion Polymerization". Biomacromolecules, vol. 2, No. 2, pp. 518 - 525 (2001).

Lander, E. S. "The New Genomics: Global Views of Biology". Sciences, vol. 274, No. 5287, pp. 536 - 539 (Oct. 25, 1996).

Lander, E. S., et al., "Array of Hope". Nature Genetics Supplement, Perspective, vol. 21, pp. 3 - 4, (Jan 1999).

Latour, P., et al., "Polymorphic Short Tandem Repeats for Diagnosis of the Charot-Marie-Tooth IA Duplication". Clinical Chemistry, vol. 47, pp. 829 - 837 (2001).

Lau, F. Y., et al., "Provision of phenotype-matched blood units: no. need for pre-transfusion antibody screening", Haematologica, vol. 86, No. 7, Jul. 2001, pp. 742 - 748.

Lee et al. "Quantitation of residual WBCs in filtered blood components by high-throughput, real time kinetic PCR", Blood Components, transfusion, vol. 42, pp. 87-93 (Jan. 2002).

Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278 - 5283 (1996).

Lee, H. J., et al., "Fabricating RNA Microarrays with RNA-DNA Surface Ligation Chemistry". Analytical Chemistry, vol. 77, no. 23, pp. 7832 - 7837 (Dec. 1, 2005).
Lee, S., et al., "Control of Core-Shell Latex Morphology". Polymer Latexes, ACS Symposium, American Chemical Society, pp. 234 - 253 (1992).
Lemieux: "high throughput single nucleotide polymorphism genotyping technology" Current Genomics. vol. 1:301-311 (2000).
Lhomme et al. "Abasic DNA structure, reactivity and recognition". Biopolymers. vol. 52 : 65 - 83 (1999).
Li, A., et al., "Multiplexed analysis of polymorphisms in the HLA gene complex using bead array chips". Tissue Anitigens, vol. 63, pp. 518 - 528 (2004).
Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).
Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235 - 246 (1999).
Liebert, M. R., et al., "Dynamics of the holes in human erythrocyte membrane ghosts". J. Biological Chemistry, vol. 257, No. 19, pp. 11660 - 11666 (1982).
Lin et al. "Raman Studies of Bovine Serum Albumin" . Biopolymers 15:203-218 (1976).
Lindahl et al., "Rate of depuriniation of native deoxyribonucleic acid". Biochemistry. vol. 11, No. 19: 3610 - 1617 (1972).
Lindahl et al., "Rate of chain breakage at apurinic sites in double-stranded deoxyribonclueic acid" Biochemistry, vol. 11, No. 19:3618-3623 (1972).
Lipshultz, R. J., et al., "High Density Synthetic Oligonucleotide Arrays". vol. 21, pp. 20-24 (Jan 1999).
Liu, et al., "Development of a Carbon Dioxide-Base Microencapsulation Technique for Aqueous and Ethanol-Based Latexes". Langmuir (2002).
Liu, V, et al, "Three-Dimensional Photopatterning of Hydrogels Containing Living Cell". Biomedical Microdevices, vol. 4, No. 4, pp. 257 - 266 (2002).
Lofas, et al., "Methods for site controlled coupling to carboxymethyldextran surfaces in surface plasmon resonance sensors". Biosensors & Bioelectronics, vol. 10, pp. 813 - 822 (1995).
Loomans, E., et al., "Assessment of the functional affinity constant of monoclonal antibodies using an improved enzyme-linked immunosorbent assay". Journal of Immunological Methods, vol. 184, pp. 207 - 217 (1995).
Ye et al., "Fluorescent Microsphere-Based Readout Technology for Multiplexed Human Single Nucleotide Polymorphism Analysis and Bacterial Identification" Human Mutation, Apr. 2001, 17 (4); 305-16).
Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).
Luo et al., "Emulsion Copolymerization of Butyl Acrylate with Cationic Monomer Using Interfacial Redox Initiator System". Journal of Polymer Science, vol. 39, pp. 2696 - 2709 (2001).
Lvov, Y, et al., "Alernate Assembly of Ordered Multilayers of SIO2 and Other Nanoparticles and Polyions". Langmuir, vol. 13, pp. 6195 - 6203 (1997).
Maldonado-Rodriguez et al., "Hybridization of glass-tethered oligonucleotide probes to . . .", Molecular Biotechnology, vol. 11, No. 1, pp. 1-12 (1999).
Marras et al., Multiplex detection of single-nucleotide variations using molecular beacons: Genetic Analysis: Biomolecular Engineering 14 (1999) 151-156.
Martin, M., et al. "A Method for Using Serum or Plasma as a Source of DNA for HLA Typing". Human Immunology, vol. 33, pp. 108 - 113 (1992).
Martinell, J. et al., "Three mouse models of human thalassemia", Proc. Natl. Acad. Sci, USA. Aug. 1981, vol. 78, No. 8, pp. 5056 - 5060 (see especially p. 5057, col. 1, last paragraph, Figure 4, and the legend to Figure 4.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675 - 1678 (1992).
Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679 - 1684 (1992).
Matthews et al., "Biochemistry: A Short Course". New York: John Wiley & Sons, Inc, p. 25 (1997).
Maxam et al., "A new method for sequencing DNA," Proc. Natl. Acad. Sci. USA. vol. 74, No. 2, pp. 560-564, Feb. 1977.
McCloskey, et al., "Magnetic Cell Separation: Characterization of Magnetophoretic Mobility". Anal. Chem., vol. 75, pp. 6868 - 6874 (2003).
McCloskey, et al., "Magnetophoretic Mobilities Correlate to Antibody Binidng Capacities". Cytometry, vol. 40, pp. 307 - 315 (2000).
Mei et al. "Genome-wide Detection of Allelic Imbalance Using Human SNPs and High-Density DNA Arrays". Genome Research. vol. 10, pp. 1126-1137 (2000).
Michael, et al., "Randomly ordered addressable high-density optical ssensor arrays". Anal. Chem, vol. 70, pp. 1242 - 1248 (1999).
Micheletto et al., "A simple method for the production of a two-dimensional ordered array of small latex particles". Langmuir, vol. 11, pp. 3333-3336 (1995).
Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539 - 1545 (May 27, 1996).
Moore, et al., "The use of magnetite-doped polymeric microspheres in calibrating cell tracking velocimetry". J. Biochem. Biophys. Methods, vol. 44, pp. 115 - 130 (2000).
Morag et al. "Immobilized nitro-avidin and nitro-streptavidin as reusable affinity matrices for application in avidin-biotin technology". Analytical Biochemistry. vol. 243: 257-263 (1996).
Mori, et al., Computer program to predict liklihood of finding an HLA-matched donor: Methodology, validation, and application. Biology of Blood and Marrow Transplantation, vol. 2, pp. 134 - 144 (1996).
Morishima et al., "Microflow system and transportation of DNA molecule by dielectrophoretic force utilizing the conformational transition in the higher order structure of DNA molecule". Proceedings — IEEE Annual International Workshop on Micro Electro Mechanical Systems: An investigation of micro structures, sensors, actuators, machines and robots. Nagoya, Jan 26-30, 1997.
Muller et al., "Gene and Haplotype Frequencies for the Loci HLA-A, HIB-B, and HLA-DR Based on Over 13,000 German Blood Donors". Human Immunology, 2003, 64: 137 - 151.
Mullis et al. Specific Synthesis of DNA in Vitro via a Polymerase-Catalyzed Chain Reaction Methods in Enzymology, 1987; vol. 155, pp. 335-350.
Nagarajan et al., "Identifying Spots in Microarray Images", IEEE Transactions on Nanobioscience, vol. 1, No. 2, pp. 78-84 (Jun. 2002).
Nagayama et al., "Fabrication of two-dimensional colloidal arrays". Phase Transitions, vol. 45, 185-203 (1993).
Nam, J., et a., "Colorimetric Bio-Barcode Amplification Assay for Cytokines". Anal. Chem., vol. 77, pp. 6985 - 6988 (2005).
Nau et al., "A Command Processor for the Determination of Specificities fro Matrices of Reactions Between Blood Cells and Antisera". Computers and Biomedical Research, vol. 10, pp. 259 - 269 (1977).
Nazarenko et al. (2002) Multiplexed quantititaive PCR using self-quenched primers labeled with a single fluorophore. Nucleic Acids Research, 30 (9), e37.
Niemeyer et al., "DNA-directed Immobilization: Efficient, Reversible, and Site-Selective Surface Binding of Proteins by means of Covalent Stretavidin Conjugates". Analytical Biochemistry, vol. 268, pp. 54 - 63 (1999).
Niemeyer et al., "Oligonucleotide-directed self-assembly of proteins: semisynthetic DNA - streptavidin hybrid molecules as connectors for the generation of macroscopic arrays and the construction of supramolecular bioconjugates". Nucleic Acids Research, vol 22, pp. 5530 - 5539 (1994).

Nygren, "Molecular Diagnostics of Infectious Diseases" Royal Institute of Technology Department of Biotechnology, Stockholm 2000, pp. 1-68.

Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.

Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo et al., "Preparation of micron-size monodisperse polymer particles by seeded polymerization utilizing the dynamic monomer swelling method". Colloid and Polymer Science, vol. 269, No. 3, pp. 222 - 226 (1991).

Olejnik et al., "Photocleavable blotin phosphoramidite for 5'-end-labelling, purification & phosphorylation of oligonucleotides", Nucleic Acids Research 1996, vol. 24, 2:361-366.

Oliver, D., et al., "Use of Single Nucleotide Polymorphisms (SNP) and Real-Time.Polymerase Chain Reaction for Bone Marrow Engraftment Analysis". Journal of Molecular Diagnostics, vol. 2, No. 4, pp. 202 - 208 (Nov. 2000).

Olson et al. "A common langauage for physical mapping of the human genome". Science, vol. 245, pp. 1434 - 1435 (1989).

Otero, T. F., et al., "Electrochemically initiated acrylic acid/acrylamide copolymerization", J. Electroanal. Chem., vol. 256, pp. 433-439 (1998).

Otero, T. F., et al., "Electroinitiated polymerization of acrylamide in DMG: Attempts at an interfacial model", J. Electroanal. Chem., vol. 304, pp. 153-170 (1991).

Pastinen, et al., "A System for specific, high-throughput genotyping by allele-specific primer extension on microarrays". Genome Res., vol. 10, pp. 1031 - 1042 (2000).

Peter, C., et al., "Optical DNA-sensor chip for real-time detection of hybridization events". Fresenius J. Anal. Chem, vol. 371, pp. 120 - 127 (Jun. 2001); Published online Springer-Verlay 2001.

Wilson, M. R., et al., "A New Microsphere-based Immunofluorescence Assay for Antibodies to Membrane-associated Antigens". Journal of Immunological Methods, vol. 107, pp. 231 - 237 (1988).

Peterson, et al. "Fiber Optic pH probe for physiological use". Anal. Chem. vol. 52, 864-869 (1980).

Peterson, et al., " Fiber Optic Sensors for Biomedical Applications". Science, vol. 13; pp. 123-127 (1984).

Peytavi et al., "Correlation between microarray DNA hybridization efficiency and the position of short capture probe on the target nucleic acid". Biotechniques, vol. 39, No. 1, pp. 89 - 96 (2005).

Pooga, M., et al., "Cell-Penetrating constructs regulate galanin receptor levels and modify pain transmission in vivo" Nature Biotechnology, vol. 16, pp. 857 - 861 (1998).

Pope. "Fiber optic chemical microsensors employing optically active silica microspheres". SPIE, vol. 2388; pp. 245-256 (1995).

Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, pp. 182-185.

Pregibon et al., "Magnetically and Biologically Active Bead-Patterned Hydrogels". Langmuir, vol. 22, pp. 5122 - 5128 (2006).

Preza, "Phase Estimation using rotational diversity for differential interference contrast microscopy". Dissertation presented to the Washington University, Server Institute of Technology, Department of Electrical Engineering; St. Louis, MO (Aug. 1998).

Proudinikov et al., "Chemical methods of DNA and RNA fluorescent labeling". Nucleic Acids Research. vol. 24, No. 22: 4535 - 4542 (1996).

Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).

Quon, R., et al., "Measurement of the Deformation and Adhesion of Rough Solids in Contact". J. Phys. Chem., vol. 103, pp. 5320 - 5327 (1999).

Rabbany et al., "Assessment of hetrogeneity in antibody displacement reactions". Anal Chem, vol. 69, pp. 175 - 182 (1997).

Radtchecnko et al., "Core-shell structures formed by the solvent-controlled precipitation of luminescent ScTe nanocrystals on latex spheres". Advanced Materials, vol. 13, No. 22, pp. 1684 - 1687 (2001).

Radtkey et al., "Rapid, high-fidelity analysis of simple sequence repeats on an electronically active DNA microchip". Nucleic Acids Research, vol. 28, No. 7, pg. e17 (2000).

Ramsay, G., "DNA Chips: State-of-the-Art". Nature Biotechnology, vol. 16, pp. 40 - 44 (Jan. 1998).

Reddy et al., "Determination of the Magnetic Susceptibility of Labeled Particles by Video Imaging". Chemical Engineering Science, vol. 51, No. 6, pp. 947 - 956 (1996).

Reid M. E., et al., "Novel Dombrock blood group genetic variants . . .", Blood (ASH Annual Meeting Abstract) 2004, 104: Abstract 383.

Relogio, A. et al., "Optimization of oligonucleotide-based DNA microarrays", Nucl. Acids Res., vol. 30, e51, pp. 1-10 (2002).

Richardson et al., "The use of coated paramagnetic particles as a physical label in a magneto-imnnunassay". Biosensors & Bioelectronics, vol. 16, pp. 989 - 993 (2001).

Richardson, et al., "A novel measuring system for the determination of paramagnetic particle lables for use in magneto-immunoassays". Biosensors & Bioelectronics, vol. 16, pp. 1127 - 1132 (2001).

Richetti et al., "Two-dimensional aggregations and crystallization of a colloidal suspension of latex spjeres", J. Physique Letter. vol. 45, pp. L-1137 to L-1143 (1984).

Righetti, P. G., et al., "Electrophoresis gel media: the state of the art", J. Chromatogr B., Biomed Sci Appl, vol. 699, No. 1-2, pp. 63 - 75 (Oct. 10, 1997).

Roberts et al. "Patterned magnetic bar array for high-thoughput DNA detection" IEEE Transaction on Magnetics. vol. 40, No. 4: 3006-3008 (2004).

Rubina et al, "Hydrogel drop microchips with immobilized DNA: properties and methods for large-scale production". Analytical Biochemistry, vol. 325, pp. 92 - 106 (2004).

Rudzinski, et al., "pH-sensitive acrylic-based copolymeric hydrogels for the controlled release of a pesticide and a micronutrient". Journal of Applied Polymer Science, vol. 87, pp. 394 - 403 (2003).

Sacchetti, et al. "Efficiency of Two Different Nine-Loci Short Tandem Repeat Systems for DNA Typing Purposes". Clinical Chemistry, vol. 45, No. 2, pp. 178 - 183 (1999).

Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665 - 669 (1999).

Sambrook et al., "Precipitation with Ethanol or Isopropanol", Concentrating Nucleic Aicds, Molecular Cloning vol. 3, pp. E3-E4 and E.10-E.15 (1989).

Sano, T, et al., "Immuno-PCR: Very Senisitive Antigen Detection by Means of Specific Antibody-DNA Conjugates". Science, vol. 258, pp. 120 - 122 (Oct. 2, 1992).

Santa Lucia, J. Jr., "A unified view of polymer, dumbbell, and oligonucleotide DNA nearest-neighbor thermodynamics". PNAS USA, vol. 95, pp. 1460-1465 (1998).

Schaid et al., "Score Tests for Association between traits and Haplotypes when Linkage Phase is Ambiguous", American Journal of Genetics. vol. 70, pp. 425 - 434 (2002).

Schena et al., "Quantitative Monitoring of Gene Expression Patterns with a Complementary DA Microarray". Science, vol. 270, pp. 467-470 (1995).

Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).

Schreiber, G. B., et al., "Increasing Blood Availability by changing Donation Patterns". Transfusion, vol. 43, pp. 591 - 597 (2003).

Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409 - 437 (1999).

Schumaker, et al., "Mutation Detection by solid phase primer extension", Human Mutation 7:346 - 354 (1996).

Wilson et al., "A generalized method for magnetite nanoparticle steric stabilization utilizing block copolymers containing carboxylic acids". European Cells and Materials, vol. 2, pp. 202 - 209 (2002).

Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).

Scillian, James J., et al., "Early Detection of Antibodies Against rDNA-Produced HIV Proteins with a Flow Cytometric Assay". Clinical Chemistry, vol. 40, No. 3, pp. 420 - 425 (1994).

Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).

S. Dubiley et al., "Polymorphism Analysis and Gene Detection by minsequencing on an array of gel immobilized primers." Nucleic Acids Research, 1999;i-vi. vol. 27, No. 16.

S. Ebel et al. "Very Stable Mismatch Duplexes: Structural and Thermodynamic Studies on G-A Mismatches in DNA" Biochemistry 31:12083-86 (1992).

Seeman, P., et al., "Structure of Membrane Holes in Osmotic and Saponin Hemolysis"; The Journal of Cell Biology, vol. 56; 519 - 527 (1973).

Sehgal et al. "A method for the high effieiency of water-soluble carbodiimide-mediated amidation". Analytical Biochemistry. vol. 218:87-91 (1994).

Seltsam, et al., Systematic analysis of the ABO gene diversity within exons 6 and 7 by PCR screening reveals new ABO alleles, Transfusion, vol. 43, pp. 428-439 (2003).

Sennerfors, T., et al., "Adsorption of Polyelectrolyte-Nanoparticle Systems on Silica: Influence of Ionic Strength". Journal of Colloid and Interface Science, vol. 254, pp. 222 - 226 (2002).

Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088 - 4094 (1998).

Sethu, P; "Microfluidic diffusive filter for apheresis (leukopheresis)"; Lab Chip, vol. 6, No. 1, pp. 83-89 (Jan 2006); Published electronically Nov 11, 2005.

Seul et al., "Domain Shapes and Patterns: The Phenomenology of Modulated Phases". Science, vol. 267:476-483 (1995).

Seul et al., "Scale transformation of magnetic bubble arrays: coupling of topological disorder and polydispersity". Science, vol. 262 : 558-560 (1993).

Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427 - 444 (1972).

Sham , P. et al., "Haplotype Association of Discrete and Continuous Traits Using Mixture of Regression Models", Behavior Genetics, Mar. 2004, 34(2), pp. 207 - 214.

Shevkoplyas, S., et al., "Biomimetic autoseparation of leukocytes from whole blood in a microfluidic device"; American Chemical Society; vol. 77, No. 3, pp. 933 - 937 (Feb. 1, 2005).

Shon. "Application Note — New Best Practices for Biosample Management: Moving Beyond Freezers". American Biotechnology Laboratory, vol. 23, No. 2, pp. 10 - 13 (2005).

Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626 - 630 (1995).

Siegel, D., "Phage display-based molecular methods in immunohematology". Transfusion, vol. 47, pp. 89S - 94S (Jul. 2007 Supplement).

Simon, R. "Application of optimization methods to the hematological support of patients with disseminated malignacies", Mathematical Biosciences, vol. 25, 1975, pp. 125 - 138.

Skalnik et al., "A Rapid Method for Characterizing transgenic Mice", S. Biotechniques 8:34 (1990).

Skolnick et al. "Simultaneous analysis of multiple polymorphic loci using amplified sequence polymorphisms (ASPs)". Genomics, vol. 2, pp. 273 - 279 (1988).

Smay, J., et al., "Colloidal Inks for Directed Assembly of 3-D Peridoic Structures". Langmuir, vol. 18, pp. 5429 - 5437 (2002).

Smith, J. W., et al., "RED: a Red-Cell Antibody Identification Expert Module". Journal of Medical Systems, vol. 9, No. 3, pp. 121 - 138 (1985).

Southern E. M., "DNA Fingerprinting by hybridisation to oligonucleotide arrays". Electrophoresis, vol. 16, No. 9, pp. 1539 - 1542 (1995).

Southern, E. M., et al., "Analyzing and comparing nucleic acid sequences by hybridization to arrays of oligonucleotides: evaluation using experimental models". vol. 13, No. 4, pp. 1008-1017 (Aug. 1992).

St. Louis, M, et al., "The Dombrock blood group system: A Review" , Transfusion 43: 1126-1132 (2003).

Steemers, F. J. (2000) Screening unlabeled DNA targets with randomly ordered fiber-optic optic gene arrays. Nat. Biotechnol., 18, 91-94.

Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953 - 1955 (2003).

Stevens, P. W., et al. "Imaging and Analysis of Immobilized Particle Arrays". Analytical Chemistry. vol. 75, pp. 1147-1154 (2003).

Storry et al, "Genetic Basis of blood group diversity". British Journal of Haematology, vol. 126, pp. 759 - 771 (2004).

Strobel E., et al., "The molecular basis of Rhesus antigen E", Transfusion 44:407- 409 (2004).

Sukhishvilli, S. A. et al. "Adsorption of human serum albumin: Dependence on molecular architecture of the oppositely charged surface" J. Chem. Phys. 110, 10153-10161 (1999).

Sun et al., "Continuous, Flow-Through Immunomagnetic Cell Sorting in a Quadrupole Field". Cytometry, vol. 33, pp. 469 - 475 (1998).

Suzawa et al., "Adsorption of Plasma Proteins onto Polymer Latices". Advances in Colloid and Interface Science, vol. 35, pp. 139 - 172 (1991).

Svitel, et al., "Combined Affinity and Rate Constant Distributions of Ligand Populations from Experimental Surface Bindinh Kinetics and Equilibria". Biophysical Journal, vol. 84, pp. 4062 - 4077 (Jun. 2003).

Syvanen, " From Gels to Chips: Minisequencing Primer Extensions for Analysis of Pont Mutations and Single Nucelotide Polymorphisms", Human Mutation 13:1-10 (1999).

Syvanen, A., et al., "Identification of Individuals by Analysis of Biallelic DNA Markers, Using PCR and Solid-Phase Minisequencing". Am. J. Hum. Genet, vol. 52, pp. 46-59 (1993).

Syvannen, A. "Toward genone-wide SNP genotyping". Nature Genetics Supplement. vol. 37: s5-s10 (2005).

Sze. MIS Diode and Charge-Coupled Device. The Physics of Semiconductors, Chapter 7, pp. 362-430 (2nd Edition) (1981).

Takeda et al. "Conformational Change of Bovine Serum Albumin by Heat Treatment", J. Protein Chemistry 8:653-659, No. 5 (1989).

Tanaka, T., et al., "Mechanical instability of gels at the phase transition", Nature, vol. 325, pp. 796 - 798 (1987).

Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).

Tarnok et al., "Cytometric Bead Array to Measure Six Cytokines in Twenty-Five Microliters of Serum," Clinical Chemistry, (2003), vol. 49, No. 6, pp. 1000-1002.

Taylor et al., "Linked oligodeoxynucleotides show binding cooperativity and can selectively impair replication of deleted mitochondrial DNA templates", Nucleic Acids Research. vol. 29, No. 16, pp. 3404 - 3412 (2001).

Tobitani et al. "Heat-induced gelation of globular proteins. 1. Model for the effects of time and temperature onthe gelation time of BSA gels." Macromolecules. vol. 30:4845-4854 (1997).

Tokumasu F. et al., Development and application of quantum dots for immunocytochemistry of human erythrocytes, J. Microscopy, 2003, pp. 256-261, vol. 211, pt. 3.

Tonisson et al., "Arrayed primer extension on the DNA chip; Method and applications", Microarray Biochip Technology, Biotechniques Books, 247 - 262 (2000).

Tsuchihashi, Z. et al. "Progress in high throughput SNP genotyping methods", the Pharmacogenomics Journal 2:103-110 (Apr. 2002).

Trau et al., "Field-induced layering of colloidal crystal", Science, vol. 272; pp. 706-709 (1996).

Trang D.T.X. et al. "One step concentration of malarial parasite-infected red blood cells and removal of contaminating white blood cells", Malaria Journal (2004) pp. 1-7 from http://www.malariajournal.com/content/3/1/7.

Trau et al., "Nanoencapsulated microcrystalline particles for superamplified biochemical assays". Anal. Chem, vol. 74, No. 21, pp. 5480 - 5486. Web Release Date: Sep. 25, 2002.

Turcanu et al, "Cell Identification and isolation on the basis of cytokine secretion: A novel tool for investigating immune responses". Nature Medicine, vol. 7, No. 3, pp. 373 -376 (Mar. 2001).

Tyagi et al., Molecular Beacons: Probes that Flouresce upon Hybridization, Nature Biotechnology vol. 14, pp. 303-308 (1996).

Vainrub, A., et al., "Sensitive quantitative nucleic acid detection using oligonucleotide microarrays". vol. 125, No. 26, pp. 7798-7799, (Jul. 2, 2003).

Van Kempen, et al., "Mean and Variance of Ratio Estimators Used in Fluorescence Ratio Imaging". Cytometry, vol. 39, pp. 300 - 305 (2000).

Van Zoelen, "Receptor-ligan interaction: a new method for determing binding parameters without a priori assumptions on non-specific binding". Biochem J., vol. 262, pp. 549 - 556 (1989).

Vasiliskov, A. V., et al., "Fabrication of Microarray of Gel-Immobilized Compounds on a Chip by Copolymerization". BioTechniques, vol. 27, pp. 592 - 606 (Sep. 1999).

Vaynberg et al. "Structure and extent of absorbed gelatin on acrylic latex and polystyrene collodial particles". Journal of Colloid and Interface Science. vol. 205:131-140 (1998).

Vet, J. A. M. (1999) Multiplex detection of four pathogenic retroviruses using molecular beacon. Proc. Natl. Acad. Sci. USA, 96, 6394-6399.

Vilain. "CYPs, SNPs, and Molecular Diagnosis in the Postgenomic Era". Clinical Chemistry, vol. 44, pp. 2403 - 2404 (1998).

Wahl et al., "Efficient transfer of large DNA fragments from agarose gels to diazobenzyloxymethyl-paper and rapid hybridization by using dextran sulfate". Proc. Natl. Acad. Sci. USA. vol 76, No. 8: 3683 - 3687 (1979).

Wang, D., et al, "Large-Scale Identification, Mapping, and Genotyping of Single-Nucleotide Polymorphisms in the Human Genome". Science, vol. 280, No. 5366, pp. 1077 - 1082 (May 15, 1998).

Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).

Weinfeld et al., "Selective hydrolysis by exo- and endonucleases of phosphodiester bonds adjacent to an apurinic site". Nucleic Acids Research, vol. 17, No. 10: 3735 - 3744 (1989).

Weissenbach et al. "A Second generation linkage map of the human genome". Nature, vol. 359, pp. 794 - 801 (1992).

Wen, et al., "Planar Magnetic Colloidal Crystals". Physical Review Letters, vol. 85, No. 25, pp. 5464 - 5467 (2000).

Wiedmann, M., et al., Ligase Chain Reaction (LCR) - Overview and Applications, PCR Methods and Applications, Genome Research, vol. 3, pp. s51 - s64 (1994).

Yeang et. al. Molecular classification of multiple tumor types. Bioinformatics vol. 17 Suppl. 1, pp. s316-s322 (2001).

J. F. Chapman et al., Working Party of the BCSH: "Guidelines for compatibility procedures in blood transfusion laboratories", Transfusion Medicine, vol. 14, pp. 59 - 73 (2004).

Yamashita et al., "Thermodynamics for the preparation of micron-sized, monodispersed highly monomer absorbed polymer particles utilizing the dynamic selling method". Colloids and Surfaces, vol. 153, pp. 153 - 159 (1999).

Yao et al., "Molecular-beacon-based array for sensitive DNA analysis". Analytical Biochemistry, vol. 331, pp. 216-223 (2004).

Fukuda et al., "Noncontact manipulation of DNA molecule 1. Transportation of DNA molecule by dielectric force". Nippon Kikai Gakkai Ronbunshu, vol. 62: 2765 - 2772 (1996).

* cited by examiner (a)

(b)

ARRAYS OF MAGNETIC PARTICLES

CROSS-REFERENCE TO RELATED APPLICATIONS

This application is a continuation of application Ser. No. 10/204,799, filed Feb. 19, 2003, now U.S. Pat. No. 7,892,854, which is an application under U.S.C. §371 of PCT" International Application No. PCT/US01/20179, filed Jun. 21, 2001, which claims priority to U.S. Provisional Application No. 60/213,106, filed Jun. 21, 2000.

FIELD OF THE INVENTION

The present invention generally relates to the field of materials science and analytical chemistry.

The present invention discloses a process for the production of libraries of encoded magnetic particles, and the formation of planar assemblies inclusive of such particles. The present invention also discloses a platform for the implementation of multistep bioanalytical assay protocols permitting the integration of sample preparation steps with the simultaneous analysis of binding interactions between multiple types of analytes and binding agents.

BACKGROUND OF THE INVENTION

Many bioanalytical procedures such as affinity purification and many biochemical assays such as immunoassays and DNA hybridization assays require the separation of specific molecules or constituents from a complex mixture. In the context of molecular and cell biology, magnetizable polymeric particles ("beads") have been widely used for this aspect of sample preparation. For example, magnetic beads displaying a short oligo-dT capture probe serve to extract messenger RNA (mRNA) molecules from a cell lysate. Following addition of particles to the lysate, molecules are captured by hybridization of their poly-A tails to the capture probe, trapped in a magnetic field gradient generated by a permanent magnet, retained by the applied magnetic field during the exchange of the lysate for fresh buffer and released into suspension by removal of the magnetic field ("Biomagnetic Techniques in Molecular Biology," Technical Handbook, $3^{rd}$ Edition, DYNAL, 1998). In a similar manner, magnetic beads displaying antibodies directed against specific cell surface antigens serve to selectively extract cells of the desired type from a given suspension ("Cell Separation and Protein Purification", Technical Handbook, $2^{nd}$ edition, DYNAL, 1997). A recent example describes a method of magnetic cell separation describes the use of magnetic particles in conjunction with optical imaging of trapped cells (A. G. J. Tibbe et al. "Optical tracking and detection of immunomagnetically selected and aligned cells" Nature Biotech., 17, 1999, 1210-1213).

The integration of assay steps, a principal objective motivating the introduction of clinical analyzers and other examples of laboratory automation, in today's state of the art relies upon a 96-well (or related) microwell format of multiple discrete reaction wells to accommodate standard robotic liquid handling ("pipetting") and reading of assay signals from individual wells by plate readers. Commercial robotic pipetting systems have been recently introduced to automate sample preparation based on the use of magnetic beads for separation. However, the integration of sample processing and a highly parallel array format of analysis by way of microfluidic operations, highly desirable in connection with the miniaturization of biochemical and analytical assay procedures, has not been described to date.

The imprinting of multiple binding agents such as antibodies and oligonucleotides on planar substrates in the form of spots or stripes facilitates the simultaneous monitoring of multiple analytes such as antigens and DNA in parallel ("multiplexed") binding assays. The miniaturization of this array format for increasing assay throughput and studying binding kinetics are described (R. Ekins, F. W. Chu, Olin. Chem. 37, 955-967 (1991); E. M. Southern, U. Maskos, J. K. Elder, Genomics 13, 1008-1017 (1992)). In recent years, this approach has attracted substantial interest particularly in connection with performing extensive genetic analysis (G. Ramsay, Nat. Biotechnol. 16, 40-44 (1998); P. Brown, D. Botstein, Nat. Genet. 21, 33-37 (1999); D. Duggan, M. Bittner, Y. Chen, P. Meltzer, J. M. Trent, Nat. Genet. 21, 10-14 (1999); R. Lipshutz, S. P. A. Fodor, T. R. Gingeras, D. J. Lockhart, Nat. Genet. 21, 20-24 (1999)).

The principal techniques of array fabrication reported to date include: refinements of the original "spotting" in the form of pin transfer or ink jet printing of small aliquots of probe solution onto various substrates (V. G. Cheung, et al., Nat. Genet. 21, 15-19 (1999)); sequential electrophoretic deposition of binding agents in individually electrically addressable substrate regions (J. Cheng, et al., Nat. Biotechnol., 541-546 (1998)), and methods facilitating spatially resolved in-situ synthesis of oligonucleotides (U. Maskos M. Southern, Nucleic Acids Res. 20, 1679-1684 (1992); S. P. A. Fodor, et al., Science 251, 767-773 (1991)) or copolymerization of oligonucleotides (A. V. Vasiliskov, et al., BioTechniques 27, 592-606 (1999)). These techniques produce spatially encoded arrays in which the position within the array indicates the chemical identity of any constituent probe (BioTechniques 27, 592-606 (1999)). All of these techniques of the prior invention require that array formation be completed prior to initiation of the assay of interest. Therefore, none of the techniques of array formation of the prior art permit the real-lime formation of arrays subsequent to completion of the binding interaction of interest.

Monodisperse magnetic particles confined to planar substrates or interfaces, and exposed to a uniform magnetic field oriented normal to the plane of the interface, form a variety of ordered two-dimensional structures (W. Wen, L. Zhang and P. Sheng "Planar Magnetic Colloidal Crystals" Phys. Rev. Lett., 85, (25), 5464-5466, 2000; M. Golosovksy, Y. Saado, and D. Davidov "Self-assembly of floating magnetic particles into ordered structures: A promising route for the fabrication of tunable photonic band gap materials" Appl. Phys. Lett., 75, (26), 4186-4170, (1999); K. Zhan, R. Lenke, and G. Maret "Two-stage melting of paramagnetic colloidal crystals in two dimensions" Phys. Rev. Letter., 82, (13), 2721-2724, 1999).

Many techniques have been suggested for the synthesis of these particles. These techniques attempt to endow the magnetic particles with certain properties that make them desirable for certain applications. These techniques can be grouped into two categories, the first category relating to synthesis of a magnetic core and the second category relates to the synthesis of a magnetic shell.

Patents that may be considered of interest in the first category include:

U.S. Pat. No. 4,358,388 to Daniel et al and U.S. Pat. No. 5,356,713 to Charmot et al. disclose a process which utilizes a suspension polymerization approach. One drawback of the process is the difficulty in controlling the mono-dispersity of the resulting magnetic Latex, and the process does not appear well suited for the generation of fluorescent magnetic particles U.S. Pat. No. 4,654,267 to Ugelstead et al discloses a nitration method which produces particles with a para-magnetic core. Following magnetization, the particles are coated with functional polymers to provide a reactive shell to produce super-paramagnetic particles of controlled morphology, polydispersity, pore size distribution, magnetic loading and surface chemistry. The encoding of such particles has not been described.

U.S. Pat. No. 4,873,102 to Chang et al discloses a process of forming magnetic polymer particles containing crystals of magnetite uniformly throughout the pores. The particles can only be used under hydrophilic conditions.

U.S. Pat. No. 5,356,713 to Charmot et al discloses magnetizable composite microspheres which are useful in biological applications but are limited by their size distribution to other applications.

U.S. Pat. No. 5,512,439 to Hornes at al discloses monodisperse, super-magnetic particles carrying a plurality of molecules of an oligonucleotide which may be used for single stranded nucleic acids. The oligonucleotides may be covalently attached or affinity bonded.

U.S. Pat. No. 5,698,271 to Liberti discloses a method for the manufacture of magnetically responsive particles. The particles have applications in a variety of preparative and diagnostic techniques.

U.S. Pat. No. 5,866,099 to Owen et al discloses a magnetic-polymer particle useful in immunoassay techniques and biological/medical applications. The particle is produced by co-precipitation of transition metals in the presence of a polymer having available coordination sites.

Patents that may be considered of interest in the second category include:

U.S. Pat. No. 5,736,349 to Sasaki et al discloses a magnetic particle for an immunoassay method which comprises a core and a coating layer. An antigen or antibody is bound onto the surface of the coating layer.

U.S. Pat. No. 5,648,124 to Sutor et al discloses a process for the production of magnetic particles by hetero-coagulation utilizing oppositely charged core particles and magnetite particles. The dispersed magnetite may be a coated micropar-ticle which can be further coated with one or more outer polymeric coatings.

U.S. Pat. Nos. 6,013,531, 5,283,079 and 5,091,206 to Wang et al disclose a process for producing magnetically responsive polymer particles. The particles comprise a polymeric core particles coated evenly with a layer of polymer containing magnetically responsive metal oxide. The surface of these magnetically responsive polymer particles can be coated further with a layer of functionalized polymer. These magnetically responsive polymer particles can be used for passive o covalent coupling of biological material and used as solid phase for various types of immunoassays.

Several methods have been described for the synthesis of stained magnetic particles. Patents that may be considered of interest include U.S. Pat. No. 5,395,688 to Wang which discloses a process for producing magnetically responsive fluorescent polymer particles composed of a fluorescent polymer core particle that is evenly coated with a layer of magnetically responsive metal oxide. The method utilizes preformed fluorescent polymeric core particles which are mixed with an emulsion of styrene and magnetic metal oxide in water and polymerized. A two-step reactive process such as this suffers from the drawback of possible inhibition of polymerization by the fluorescent dye or conversely bleaching of the fluorescence by the shell polymerization process. The use of such magnetic particles containing fluorescent tags for the calibration of certain solid phase assays has been described in U.S. Pat. No. 6,013,531. Following completion of this step, the particles are coated with functional polymers to provide a reactive shell.

The creation of core-shell particles from dispersed colloidal matter can be accomplished by a multistep (layer-by-layer) strategy. The process involves step-wise adsorption of charged polymers or nanoparticles and oppositely charged polyelectrolytes onto colloidal particles, exploiting primarily electrostatic interactions for layer buildup. (Caruso et al "Magnetic Core-Shell Particles: Preparation of Magnetite Multilayers on Polymer Latex Microspheres" Adv. Mater. 1999, 11, 950-953) A shell applied by electrostatic physisorption is not desirable for bioanalytical assays because it is chemically unstable under changes of assay conditions, particularly salt concentration, and promotes non-specific adsorption and denaturation of charged biomolecules; the particles described in this prior art reference are unsuitable in connection with the assay formats contemplated herein.

While the foregoing references disclose the use of magnetic particles, none of the prior art particles appear to possess the properties that are necessary to meet the criteria which are necessary for the successful performance of the assays described herein including a preferred size range, substantial monodispersity, chemical functionalization and synthetic flexibility, the latter permitting the rapid construction of libraries of encoded magnetic particles that can be functionalized on demand, the chemical diversity represented in these libraries greater than 2. In addition, magnetic particles must meet certain standards of quality to permit the reproducible assembly of customized arrays to ensure consistent performance in quantitative assays.

SUMMARY OF THE INVENTION

The present invention provides methods, compositions and processes relating to the implementation of bioanalytical assay procedures for multiplexed molecular interaction analysis. The processes of the invention employ a multiplicity of encoded magnetic particles, distinguishable on the basis of their encoding. Such particles display one or more binding agents which are capable of interacting with one or more specific analytes upon coming into contact such particles.

The present invention provides a process for the preparation of libraries of particles which are a composite of an encoded particle and a multitude of magnetic nanoparticles ("composite particles"). Such composite particles can be functionalized to be able to be utilized in a particular assay. Examples of such functionalization include the inclusion of binding agents such as oligonucleotides, DNA, peptides or proteins. Such composite particles include an optically differentiable code, such code selected to reflect the nature of the displayed binding agent, such that the composite particles and their associated binding agents are distinguishable by real time, in-situ inspection. Custom bead arrays can be fabricated on demand using such libraries. Such arrays are useful in bioassays, including assays involving multiplexed molecular interaction analysis.

The bioanalytical assay platform disclosed herein utilizes libraries of composite particles to integrate principal assay steps including sample capture and preparation, processing and analysis. In a preferred embodiment, analysis is performed in a highly parallel bead array format in which arrays are assembled in real time following completion of sample preparation and processing steps.

BRIEF DESCRIPTION OF DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which:

FIG. 27($ii$) is a schematic illustration of the 2D structure of the bead assembly after application of a magnetic field of about 100 Gauss. FIG. 27($iii$) is a schematic illustration of a close-up of 2D assembly in FIG. 27($ii$). FIG. 27($iv$) is a schematic illustration of the 2D arrangement for a higher (2×) bead concentration under a magnetic field of about 20 Gauss.

DETAILED DESCRIPTION OF THE PREFERRED EMBODIMENTS

The fabrication of application-specific bead arrays may involve multiple processes in a multi-step sequence which may be automated using existing liquid handling technology and laboratory automation. The process described herein and referred to as random encoded array detection ("READ") includes the fabrication of random encoded arrays as well as the use of such arrays in bioassays, including assays involving multiplexed molecular interaction analysis, including but not limited to the interaction of analyte and binding agent molecules, as exemplified by DNA and protein analysis. Random encoded arrays, as described herein, as well as in U.S. Pat. No. 6,251,691 overcome many of the shortcomings associated with processes employing multi-step sequences.

As used herein, the terms "analyte" and "binding agent" refer to molecules involved in binding interactions. By way of example, analyte and binding agent may include DNA or RNA fragments (e.g., oligonucleotide), aptamers, peptides, and proteins, antigens and small organic molecules. In a particular assay, binding of these fragments to their complementary sequences (hybridization) is analyzed. In another particular assay, binding interactions between ligands and receptors are analyzed.

As used herein, the term "particles" refers to colloidal particles and beads. The term "particle" is also used in connection with the encoded particles and magnetic particles of the invention.

As used herein, the term "magnetic particle" refers to a particle possessing a permanent or induced dipole moment.

Figure 1:
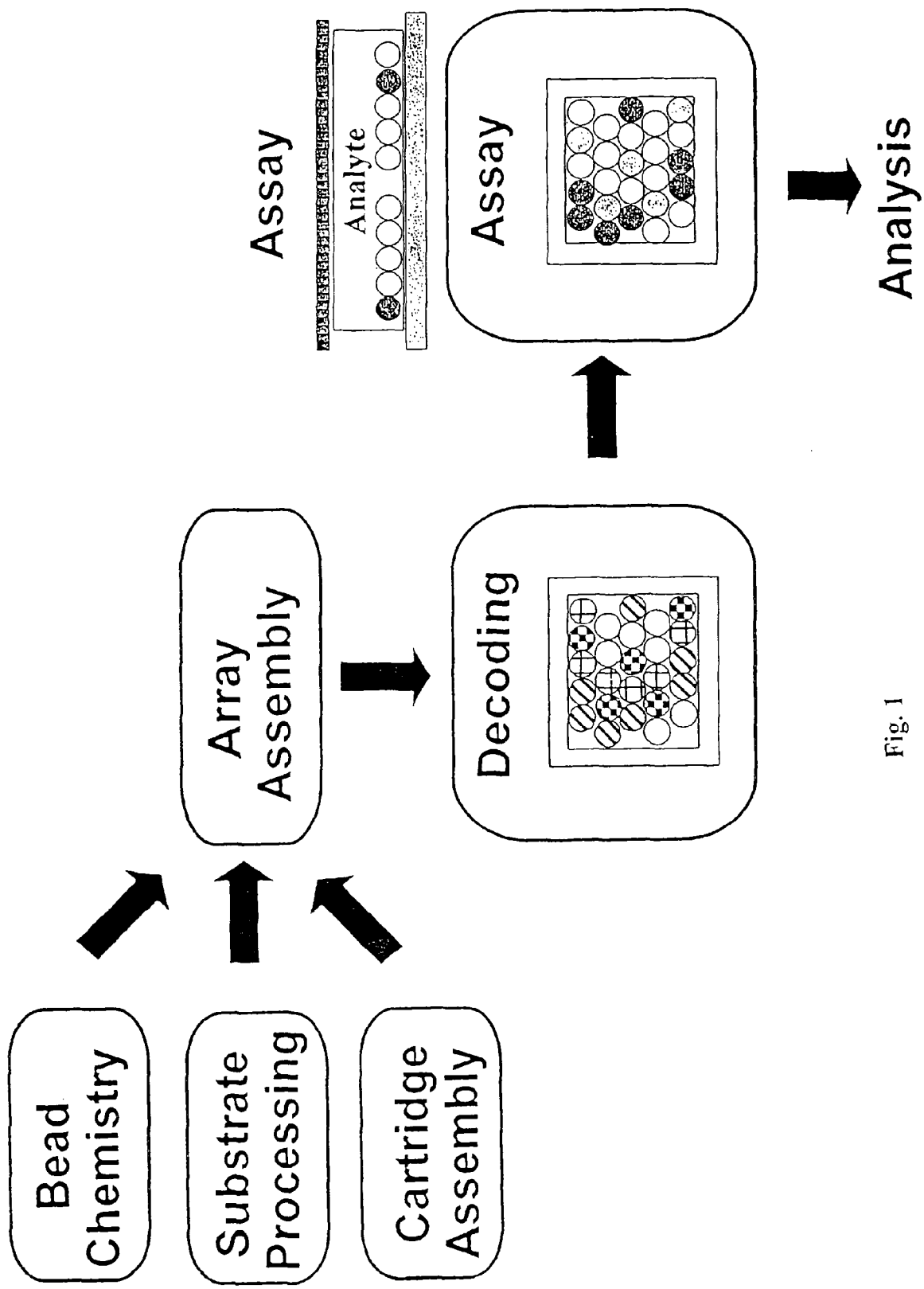
FIG. 1 is an illustration of process flow including the production of random encoded bead arrays and their use in multiplexed assays.

FIG. 1 provides a schematic overview of the functional components and process flow by which custom bead arrays may be prepared and used in performing multiplexed biomolecular analysis according to the present invention. The array is prepared by employing separate batch processes to produce application-specific substrates (e.g., chip at the wafer scale), to produce beads that are encoded and functionalized (e.g., at the scale of ~10^8 beads/100 μl of suspension) or to produce beads that are encoded, magnetic and functionalized. The beads subjected to respective quality control (QC) steps prior to array assembly, such as the determination of morphological and electrical characteristics. In addition, actual assays are performed on beads in suspension, before they are introduced to the substrate, to optimize assay conditions, generally with the objective to maximize assay sensitivity and specificity and to minimize bead-to-bead variations. For substrates, QC steps may include optical inspection, ellipsometry and electrical transport measurements.

Once the chemically encoded and biologically functionalized beads are combined with the substrate (e.g., chip), the process described in U.S. Pat. No. 6,251,691 ("LEAPS") in conjunction with the process described in PCT/US97/08159 may be used for rapid assembly of dense arrays on a designated area on the substrate within the same fluidic phase, avoiding problems contributing to spot-to-spot as well as chip-to-chip variability without the need for retooling or process redesign. Furthermore, the bead array format permits chip-independent characterization of beads as well as optimization of assay conditions. In addition, multiple bead arrays can be formed simultaneously in discrete fluid compartments maintained on the same chip. Once formed, these multiple bead arrays may be used for concurrent processing of multiple samples. The integration of LEAPS with microfluidics produces a self-contained, miniaturized, optically programmable platform for parallel protein and DNA analysis. U.S. Pat. No. 6,251,691 and PCT/US97/08159 are incorporated herein by reference in their entirety.

In certain embodiments of the present invention, chemical encoding may be accomplished by staining beads with sets of optically distinguishable tags, such as those containing one or more fluorophore dyes spectrally distinguishable by excitation wavelength, emission wavelength, excited-state lifetime or emission intensity. The optically distinguishable tags made be used to stain beads in specified ratios, as disclosed, for example, in Fulwyler, U.S. Pat. No. 4,717,655. Staining may also be accomplished by swelling of particles in accordance with methods known to those skilled in the art, (Molday, Dreyer, Rembaum & Yen, J. Mol Biol 64, 75-88 (1975); L. Bangs, "Uniform Latex Particles, Seragen Diagnostics, 1984]. For example, up to twelve types of beads were encoded by swelling and bulk staining with two colors, each individually in four intensity levels, and mixed in four nominal molar ratios. Combinatorial color codes for exterior and interior surfaces is disclosed in International Application No. PCT/US/98/10719, which is incorporated herein by reference in its entirety.

Figure 2:
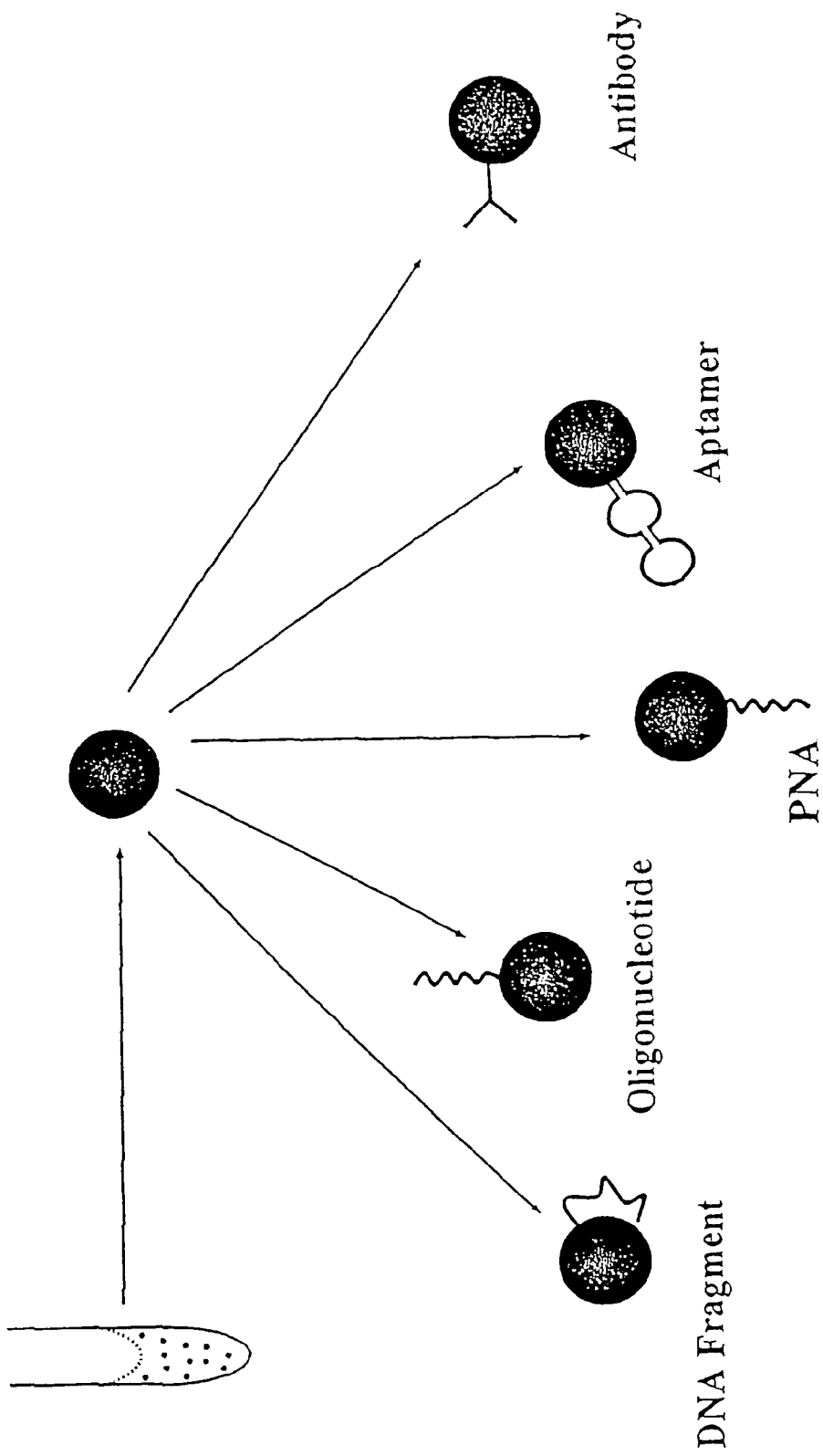
FIG. 2 is an illustration of the functionalization of beads.

Beads are functionalized by binding agent molecules attached thereto, the molecule including DNA (oligonucleotides) or RNA fragments, peptides or proteins, aptamers and small organic molecules in accordance processes known in the art, e.g., with one of several coupling reactions of the known art (G. T. Hermanson, Bioconjugate Techniques (Academic Press, 1996); L. Ilium, P. D. E. Jones, Methods in Enzymology 112, 67-84 (1985). In certain embodiments of the invention, the functionalized beads have binding agent molecules (e.g., DNA, RNA or protein) covalently bound to the beads. Beads may be stored in a buffered bulk suspension until needed. Functionalization typically requires one-step or two-step reactions which may be performed in parallel using standard liquid handling robotics and a 96-well format to covalently attach any of a number of desirable functionalities to designated beads, as illustrated in FIG. 2. In a preferred embodiment, beads of core-shell architecture will be used, the shell composed in the form of a thin polymeric blocking layer whose preferred composition is selected; and functionalization performed in accordance with the targeted assay application, as known in the art. Samples may be drawn for automated QC measurements. Each batch of beads provides material for hundreds of thousands of chips so that chip-to-chip variations are minimized.

Figure 3:
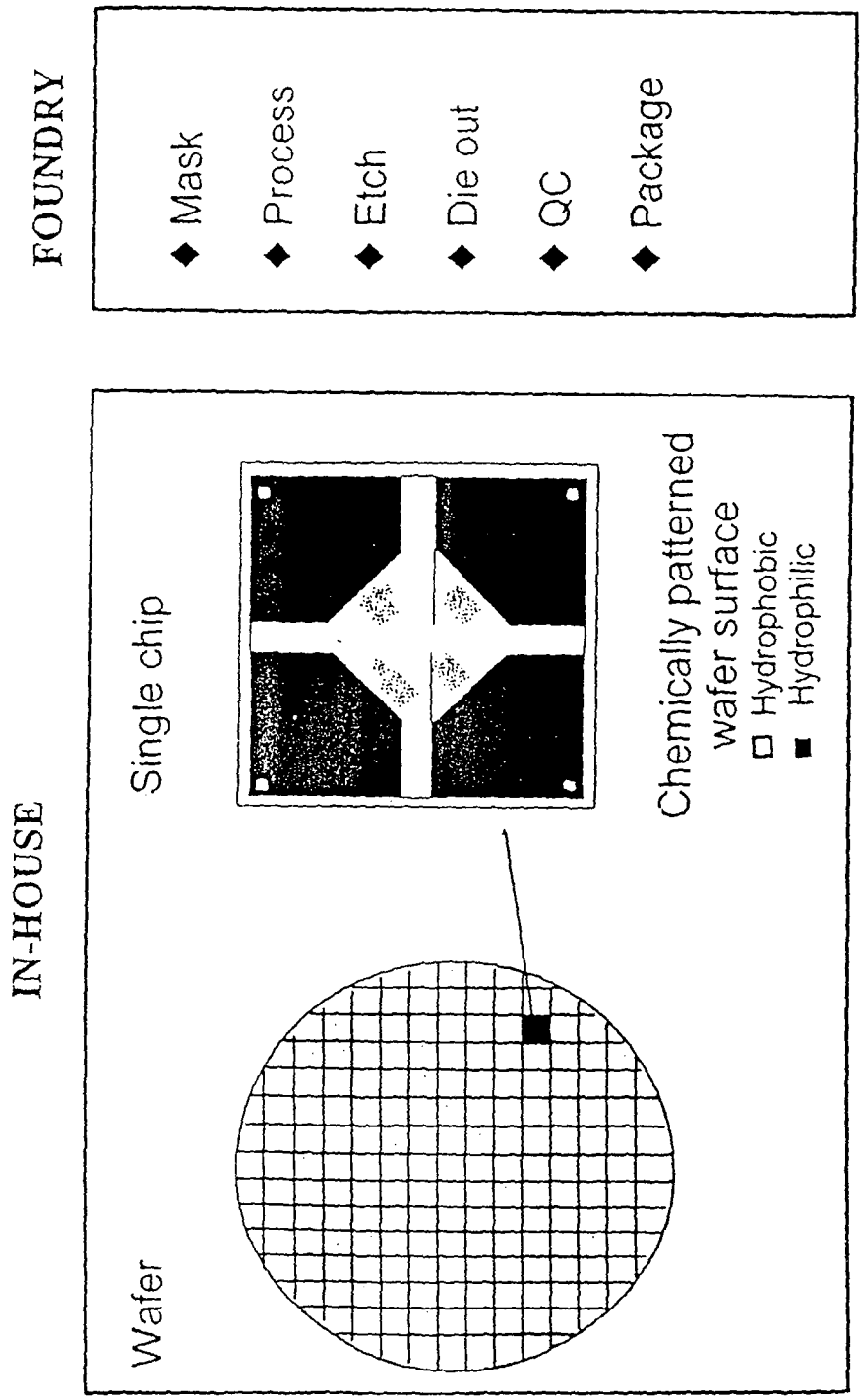
FIG. 3 is an illustration of steps in chip design and wafer-scale production.
Figure 4:
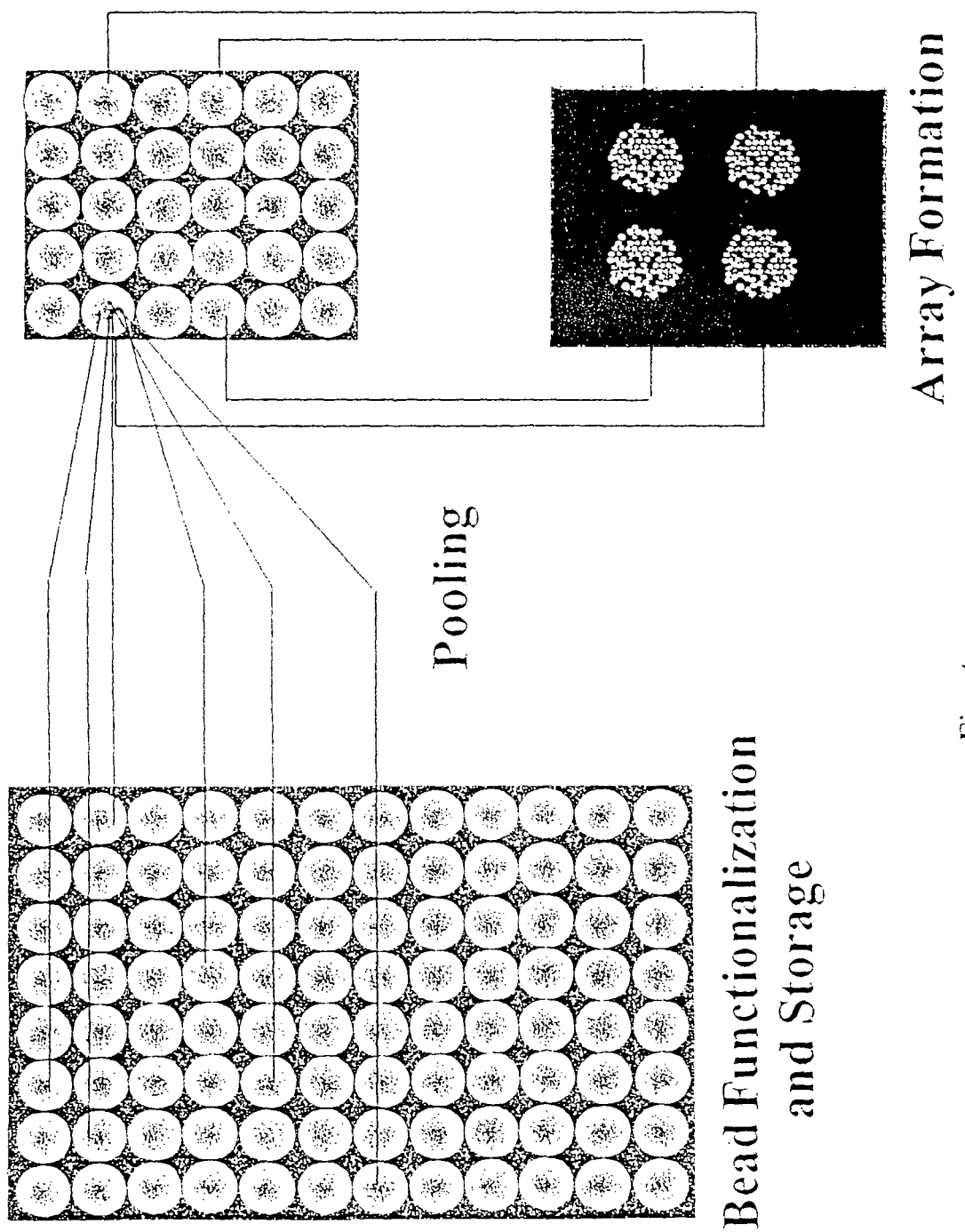
FIG. 4 is an illustration of on-demand assembly of random encoded arrays.

Substrates (e.g., chips) used in the present invention may be patterned in accordance with the interfacial patterning methods of LEAPS, by for example, patterned growth of oxide or other dielectric materials to create a desired configuration of impedance gradients in the presence of an applied AC electric field. Patterns may be designed so as to produce a desired configuration of AC field-induced fluid flow and corresponding particle transport. Substrates may be patterned on a wafer scale by invoking semiconductor processing technology, as illustrated in FIG. 3. In addition, substrates may be compartmentalized by depositing a thin film of a UV-patternable, optically transparent polymer to affix to the substrate a desired layout of fluidic conduits and compartments to confine fluid in one or several discrete compartments, thereby accommodating multiple samples on a given substrate.

In certain embodiments of the invention, the bead array is prepared by providing a first planar electrode that is substantially parallel to a second planar electrode ("sandwich" configuration) with the two electrodes being separated by a gap and containing an electrolyte solution. The surface or the interior of the second planar electrode is patterned with the interfacial patterning method. Encoded and functionalized beads are introduced into the gap. When an AC voltage is applied to the gap, the beads form a random encoded array on the second electrode (e.g., "chip"). And, also using LEAPS, an array of beads may be formed on a light-sensitive electrode ("chip"). Preferably, the sandwich configuration described above is also used with a planar light sensitive electrode and another planar electrode. Once again, the two electrodes are separated by the a gap and contain an electrolyte solution. The functionalized and encoded beads are introduced into the gap. Upon application of an AC voltage in combination with a light, the beads form an array on the light-sensitive electrode.

In certain embodiments, the application-specific bead arrays useful in the present invention may be produced by picking aliquots of designated encoded beads from individual reservoirs in accordance with the specified array composition and "pooled"; aliquots of pooled suspension are dispensed onto selected substrate (e.g., chips) in a manner preventing the initial fusion of aliquots. Aliquots form a multiplicity of planar random subarrays of encoded beads, each subarray representing beads drawn from a distinct pool and the physical array layout uniquely corresponding to the identity of aliquots drawn from pooled bead populations.

Planar arrays or assemblies of encoded beads on a substrate which are chemically or physically encoded may be used. To this, spatial encoding may also be added to increase the number of assays that may be conducted. Spatial encoding, for example, can be accomplished within a single fluid phase in the course of array assembly using LEAPS to assemble planar bead arrays in any desired configuration in response to alternating electric fields and/or in accordance with patterns of light projected onto the substrate. LEAPS creates lateral gradients in the impedance of the interface between silicon chip and solution to modulate the electrohydrodynamic forces that mediate array assembly. Electrical requirements are modest: low AC voltages of typically less than $10V_{pp}$ are applied across a fluid gap of typically 100 µm between two planar electrodes. This assembly process is rapid and it is optically programmable: arrays containing thousands of beads are formed within seconds under electric field. The formation of multiple subarrays, can also occur in multiple fluid phases maintained on a compartmentalized chip surface.

The multiplexed assays of the present invention may also be performed using encoded beads that are assembled, but not in an array, on the substrate surface. For example, by spotting bead suspensions into multiple regions of the substrate and allowing beads to settle under gravity, assemblies of beads can be formed on the substrate. In contrast to the bead arrays formed by LEAPS, these assemblies generally assume low-density, disorder configurations. However, the combination of spatial and color encoding attained by spotting mixtures of chemically encoded beads into a multiplicity of discrete positions on the substrate still provides a degree of multiplexing that is sufficient for certain biological assays.

Binding interaction between the binding agent on those beads and an analyte may be performed either before or after the encoded array is assembled on the substrate. For example, the bead array may be formed after the assay, subsequent to which an assay image and a decoding image may be taken of the array. Alternatively, the beads may be assembled in an array and immobilized by physical or chemical means to produce random encoded arrays, e.g., with the appearance of the array shown in FIG. 10. The arrays may be immobilized, for example, by application of a DC voltage to produce random encoded arrays with the appearance of the array shown in FIG. 10. The DC voltage, set to typically 5-7 V (for beads in the range of 2-6 μm and for a gap size of 100-150 μm) and applied for <30 s in "reverse bias" configuration so that an n-doped silicon substrate would form the anode, causes the array to be compressed to an extent facilitating contact between adjacent beads within the array and simultaneously causes beads to be moved toward the region of high electric field in immediate proximity of the electrode surface. Once in sufficiently close proximity, beads are anchored by van der Waals forces mediating physical adsorption. This adsorption process is facilitated by providing on the bead surface a population of "tethers" extending from the bead surface; polylysine and streptavidin have been used for this purpose.

In certain embodiments, the particle arrays may be immobilized by chemical means, for example, by forming a composite gel-particle film. In one exemple for forming such gel-composite particle films, a suspension of microparticles is provided which also contains all ingredients for subsequent in-situ gel formation, namely monomer, crosslinker and initiator. The particles are assembled into a planar assembly on a substrate by application of LEAPS, e.g., AC voltages of 1-20 $V_{p-p}$ in a frequency range from 100's of hertz to several kilohertz are applied between the electrodes across the fluid gap. Following array assembly, and in the presence of the applied AC voltage, polymerization of the fluid phase is triggered by thermally heating the cell ~40-45° C. using an IR lamp or photometrically using a mercury lamp source, to effectively entrap the particle array within a gel. Gels may be composed of a mixture of acrylamide and bisacrylamide of varying monomer concentrations from 20% to 5% (acrylamide:bisacrylamide=37.5:1, molar ratio), or any other low viscosity water soluble monomer or monomer mixture may be used as well. Chemically immobilized functionalized microparticle arrays prepared by this process may be used for a variety of bioassays, e.g., ligand receptor binding assays.

In one example, thermal hydrogels are formed using azo-diisobutyramidine dihydrochloride as a thermal initiator at a low concentration ensuring that the overall ionic strength of the polymerization mixture falls in the range of ~0.1 mM to 1.0 mM. The initiator used for the UV polymerization is Irgacure 2959® (2-Hydroxy-4'-hydroxyethoxy-2-methyl-propiophenone, Ciba Geigy, Tarrytown, N.Y.). The initiator is added to the monomer to give a 1.5% by weight solution.

In certain embodiments, the particle arrays may be immobilized by mechanical means. For example, an array of microwells may be produced by standard semiconductor processing methods in the low impedance regions of the silicon substrate. The particle arrays may be formed using such structures by, for example, utilizing LEAPS mediated hydrodynamic and ponderomotive forces are utilized to transport and accumulate particles on the hole arrays. The AC field is then turned off and particles are trapped into microwells, and are therefor, mechanically confined. Excess beads are removed leaving behind a geometrically ordered random bead array on the substrate surface.

When the bead array is immobilized before the assay, the array functions as a two-dimensional affinity matrix which displays receptors or binding agents (e.g., oligonucleotides, cDNA, aptamers, antibodies or other proteins) to capture analytes or ligands (DNA, proteins or other small cognate ligands) from a solution that is brought in contact with the array. The bead array platform may be used to perform multiplexed molecular analysis, such as, e.g., genotyping, gene expression profiling, profiling of circulation protein levels and multiplexed kinetic studies.

Figure 5:
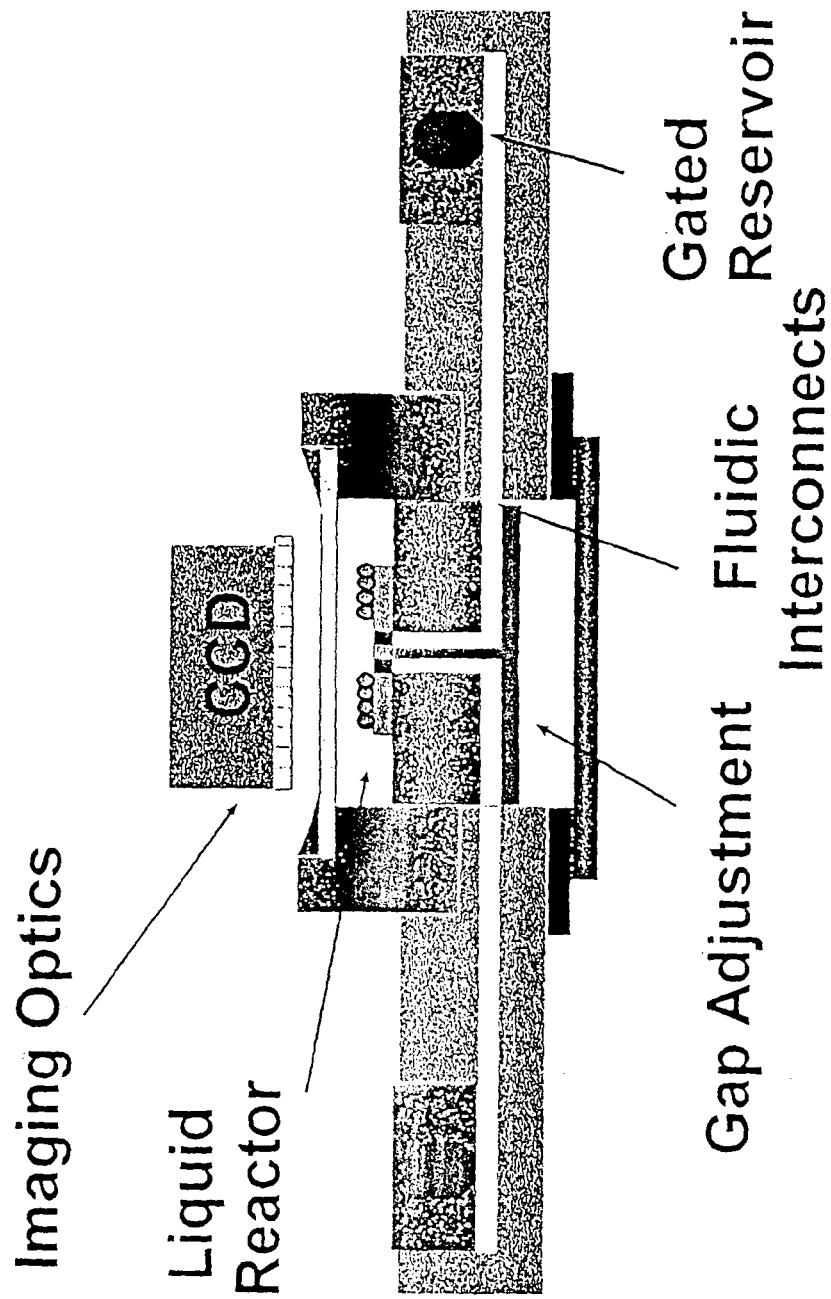
FIG. 5 is an illustration of palmtop microlab.
Figure 6:
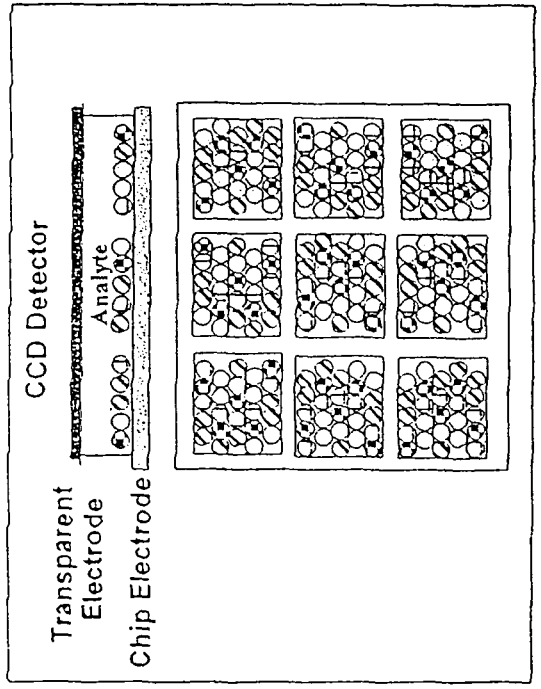
FIG. 6 is a schematic illustration of assay and decoding images used in the random encoded array detection process of the invention.
Figure 6:
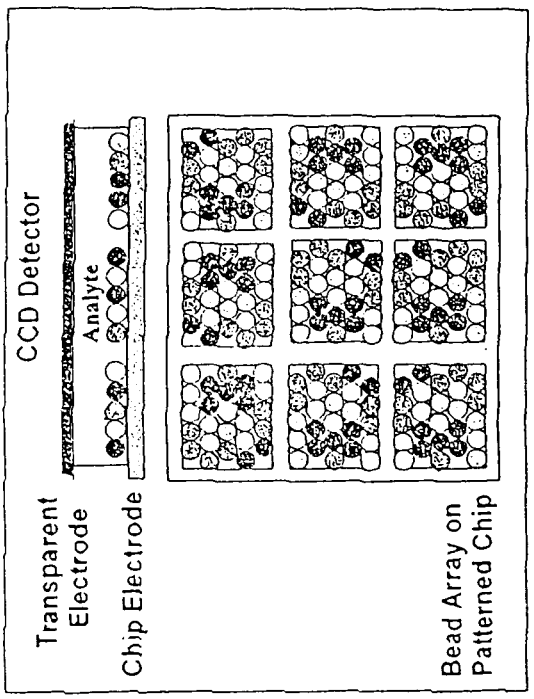

Substrates (e.g., chips) can be placed in one or more enclosed compartments, permitting samples and reagents to be transported in and out of the compartments through fluidic interconnection. On-chip immunoassays for cytokines, e.g., interleukin (IL-6) may be performed in this format. Serum sample and fluorescent labeled secondary antibodies are introduced to the reaction chamber sequentially and allowed to react with beads immobilized on the chip. FIG. 5 illustrates a design of a reaction chamber which may be used in the multiplexed assays according to the present invention. Reactions can also be performed in an open compartment format similar to microtiter plates. Reagents may be pipetted on top of the chip by robotic liquid handling equipment, and multiple samples may be processed simultaneously. Such a format accommodates standard sample processing and liquid handling for existing microtiter plate format and integrates sample processing and array detection.

In certain embodiments, the presence of the analyte-binding agent interactions are associated with changes in the optical signatures of beads involved in the interactions and these optical changes detected and analyzed. The identities of the binding agents involved in the interactions are determined by detecting the chemically or physically distinguishable characteristic associated with those beads. Preferably, chemically distinguishable characteristics include chemical molecules including flurophore dyes, chromophores and other chemical molecules that are used for purposes of detection in binding assays.

The detection of the chemically or physically distinguishable characteristic and the detection of optical signature changes associated with the binding interactions may be performed while the particles are assembled in a planar array on a substrate, for example, by taking an assay and a decoding image of the array and comparing the two, for example, a comparison of the assay and the decoding image comprises the use of optical microscopy apparatus including an imaging detector and computerized image capture and analysis apparatus. The decoding image may be taken to determine the chemically and/or physically distinguishable characteristic that uniquely identifies the binding agent displayed on the bead surface, for example, by determining the identity of the binding agents on each particle in the array by the distinguishable characteristic. The assay image of the array is taken to detect the optical signature of the binding agent and the analyte complex. In certain embodiments, fluorescent tags (fluorophore dyes) may be attached to the analytes such that when the analytes are bound to the beads, the flourescent intensities change, thus providing changes in the optical signatures of the beads. In certain embodiments, the decoding image is taken after the beads are assembled in an array and immobilized and before taking the assay image, preferably before contacting the binding agents on the beads with an analyte. In certain other examples, the binding interactions occur while the beads are in solution, and assembled into an array afterwards and the decoding and assay images are obtained.

The identity of the binding agent of the binding agent-analyte complex is carried out by comparing the decoding image with the assay image.

Figure 7:
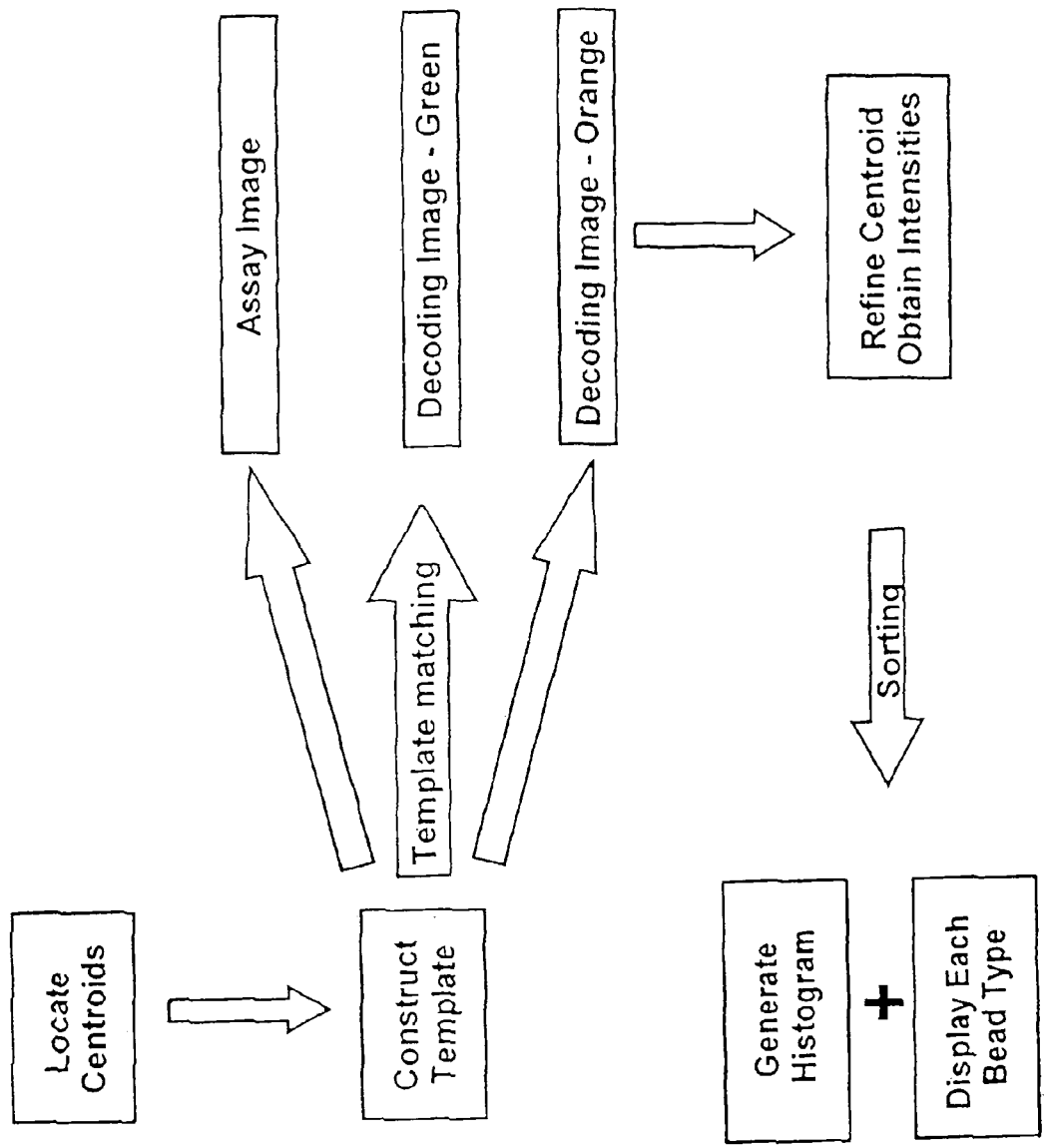
FIG. 7 is a flow chart summarizing algorithms and steps in the analysis of images.
Figure 8:
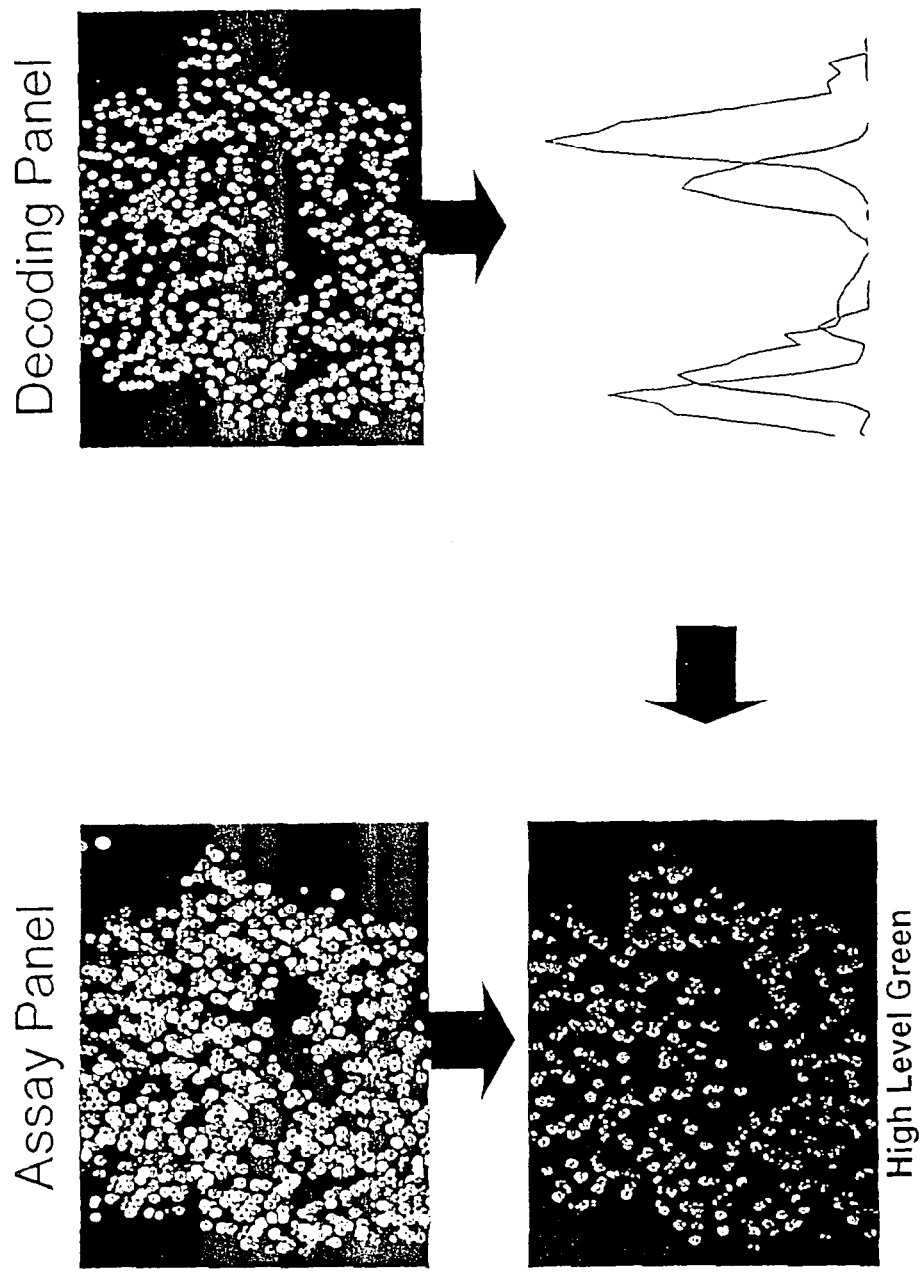
FIG. 8 is an illustration of steps in the decomposition of assay images according to bead type by application of the image analysis algorithm summarized in FIG. 7.

In preferred embodiments, images analysis algorithms that are useful in analyzing the data obtained from the decoding and the assay images. These algorithm may be used to obtain quantitative data for each bead within an array. As summarized in FIG. 7, the analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances.

The methods of the present invention may be used for determining the association and the dissociation constants e.g., by introducing the analyte in a time-dependent manner and analyzing the binding as a function of time, or by washing away the bound analyte in a time-dependent manner and also analyzing the binding as a function of time.

The methods of the present invention may be used for determining the affinity constants of analyte-binding agent interactions, for determining the number of analyte-binding agent complexes formed The present invention also provides methods for determining the concentration of an analyte in a biological sample.

The methods of the present invention may also be used to determining elements of a co-affinity matrix of a given analyte against a panel of binding agents. In one example, the extent of the interaction between the analyte and the binding agents in a panel in competitive, multiconstituent equilibrium reaction may be determined. Determination of co-affinity constants provides useful applications, as described below.

The successful rate of transplantation for several types of organs directly relates to compatibility of Human Leukocyte Antigen (HLA) between donor and recipient. Serological testing of the recipients for the Panel Reactive Antibodies (PRA) is one of the crucial steps to avoid possible rejections. Cross-reaction in PRA testing is a very common phenomenon due to similarity of some HLA antigen structures and the nature of development of these antibodies. In fact, HLA antigens can be organized into groups based on apparent serological cross-reactivity between the groups. These groups are termed Cross-Reactive-Groups (CREGs). In current clinical setting, antibodies from a patient are tested against different antigens in individual reactions. Although a reactive pattern of the antibodies can be generated combining the results from different reactions, the competitive nature of interactions between different antibodies and antigens is not reflected in such a pattern. In other cases, several antigens are mixed together for a binding assay. Lack of identification of each antigen in the system prevents generation of a binding profile. The result is only the averaged signal from several antigens. In the bead array system, a panel of different antigens is presented to the antibody analytes in a competitive binding environment, and each antigen can be identified through its association with different types of beads. Thus, binding intensity on each antigen in the competitive reactions can be extracted in a single assay. This co-affinity matrix system will provide binding profiles for the CREGs and greatly advance the understanding of the nature of the reaction and improve the accuracy for the related clinical decisions. For example, a N-antibody and M-antigen system provides a matrix of N×M of possible reactions. It is possible to determine K-nm, the affinity constant governing the interaction between the nth antibody against the mth antigen, where m=1, 2, . . . M, and n=1, 2, . . . N. For applications where absolute co-affinity constants are not needed, binding profile will be generated for various antibodies in accordance with the methods of the present invention and results from a patient sample can be matched to these profiles or combination of these profiles.

Co-affinity matrix may also be used to characterize the analyte. For example, combination of the coefficients of the co-affinity matrix and known concentrations of analyte and binding agents participating in the formation of analyte-binding agent complexes serves to define a competitive binding interaction descriptor, e.g., The molecular interaction parameter, $$P_n(R_m) = \frac{K_{mn}[L_n]}{\sum_j K_{mj}[L_j]}$$

provides a characterization of the molecular interaction between a binding agent, $R_m$, and an analyte, $L_n$, in the presence of analytes $\{L_j; 1 \leq j \leq N\}$, all of which exhibit a finite affinity, $K_{mj}$, for that binding agent. That is, $P_n$, $0 \leq P_n \leq 1$, represents a normalized specificity of binding agent $R_m$ for analyte $L_n$ in a multiconstitutent competitive reaction and serves as a robust characterization of that binding agent based on co-affinities displayed in a multiconstituent competitive reaction. See also P. H. von Hippel et al., Proc. Natl. Acad. Sci. USA 83, 1603 (1986), incorporated herein by reference.

The pattern of binding interaction of a analyte against a panel of binding agents may be used to characterize the analyte and compare it with other molecules. In addition, by generating the co-affinity matrix of a analyte using a reference panel of binding agents, such affinity may be used to determine if a sample later introduced to the panel of binding agents contains an impurity by observing the deviation in the binding pattern.

The present invention also provides use of superparamagnetic particles ("magnetic particles") as described in U.S. Pat. No. 5,759,820 and European Patent No. 83901406.5 (Sintef), which may then be used in integrated the sample preparation step with the assay step involving encoded bead arrays. Both of these references are incorporated herein by reference.

Superparamagnetic particles may be encoded with a chemically or physically distinguishable characteristic (e.g., fluorescent tag) and used performing bioassays of the present invention. In certain embodiments, the particles are assembled using LEAPS, as with non-magnetic encoded beads. The encoded nanoparticles can be also be used in array generation, and assayed. The present invention also includes the formation of a planar array of encoded and functionalized superparamagnetic particles on a substrate by application of magnetic field to said particles.

The invention provides a novel process for making color encoded magnetic beads, a simple and flexible one-step process to introduce into preformed polymeric microparticles a well controlled amount of magnetic nanoparticles, prepared in accordance with the procedure described below, along with well controlled quantities of one or more fluorescent dyes. In an embodiment of the present invention, the quantity of the magnetic nanoparticles is controlled to produce magnetic particles that form an array on a substrate upon application of magnetic field to said particles. This process involves swelling the polymer particles in an organic solvent containing dyes and magnetic nanoparticles and therefore applies to any polymer particle which can be subjected to standard swelling procedures such as those disclosed in the prior art of fluorescent staining of microparticles. Unlike encoding methods in which the magnetic material and the fluorescent dyes are each located to different areas of the (core/shell) of the magnetic particle, uniform swelling of particles ensures the distribution of magnetic particles throughout the interior volume. This process also permits the quantitative control of the nanoparticle as well as dye content over a wide range, thereby permitting the tailoring of the particles' magnetic susceptibility as well as fluorescence intensities. An additional method of the present invention to control the magnetic properties of the host particles, other than to control loading, is to tune the size of the magnetic nanoparticles by adjusting the water content of the micellar synthesis reaction (see below). Physical or chemical coupling of biomolecules possible on the particle surface utilizing preexisting functional groups. Leaching out of magnetic nanoparticles is readily eliminated by growing a further polymeric shell on the particle.

The invention also provides a novel process for the production of libraries of encoded magnetic particles, by a two-step process. The first step in the process involves the production of a sub-library of magnetic nanoparticles and the second step in the process involves the production of a sub-library of encoded particles. Following sub-library formation, as more specifically described below, the members of each sub-library are endowed with a coupling site and also functionalized The sub-library of magnetic nanoparticles can be produced by combining a metal oxide dispersion with a monomer solution and forming a polymer matrix of particles encapsulating particles of metal oxide. The metal oxide dispersion may include a metal oxide, used alone or in combination with a different metal oxide. The metal oxide may include without limitation, oxides of iron, manganese, cobalt, zinc, nickel and copper, or the like. The monomer solution may include a monomer, used alone or in combination with a different monomer. The monomer may include without limitation, styrene, methyl-methacrylate, acrylamide, ethylene-glycol acrylate, hydroxy-ethyl-methacrylate, vinyl-toluene, divinyl-benzene, or the like. Alternatively, a polymer solution can be used and may include a polymeric material such as cellulose, protenaceous polymer, glass, agarose, gelatin, or the like. The magnetic nanoparticles may be on any size and shape, but are preferably, spherical, monodisperse and from about 0.01 to about 1 micron, preferably from about 0.05 to about 0.4 microns.

The sub-library of encoded particles can be formed by encapsulating an optical identifier in a polymeric material. The polymeric material may include one polymer, used alone or in combination. The polymers may include without limitation, polystyrene, polymethyl-methacrylate, poly-acrylamide, poly-ethylene-glycol, poly-hydroxy-ethyl-methacrylate, polyvinyl-toluene, poly-divinyl-benzene, brominated polystyrene, polyacrolein, polyethylene, polyurethane, polyvinyl alcohol, polyvinylchloride or combinations thereof, or the like. The optical identifier may include one or more dyes with emission wavelengths between 200 nm and 1200 nm. Preferred dyes include but are not limited to pyro-methane and coumarin dyes. More than one dyes with distinguishable emission spectra can be used simultaneously and are selected based on their emission spectra.

The encoded particles of the invention may be of any size and shape, but are preferably polymeric, spherical, monodisperse and from about 0.6 to about 100 microns, preferably from about 1.5 to about 10 microns.

Depending on the application of interest as may be illustrated from the embodiments and examples that follow, each sub-library of the invention can be customized. In one embodiment, such customization can be accomplished by endowing the magnetic nanoparticles with a coupling site or a functional site which can both be selected based on the application of interest. Such sites can be formed by attachment of a molecular group of interest to the outside surface of the magnetic particle. The coupling sites may be formed during the polymerization step and the functional sites may be formed at a later stage, prior to formation of the composite particles as illustrated below. Molecular entities of applicability to the invention for the generation of a coupling site include without limitation any group such as carboxylic, ester, amine, aldehyde, alcohol, or halide, streptavidin, avidin, neutravidin, biotin or the like. Molecular entities of applicability to the invention for the generation of a functional site include without limitation streptavidin, avidin, neutravidin, biotin, protein A or the like. The pre-selection of a molecular entity to endow the magnetic nanoparticles of the invention with a particular functional site provides the ability to compile a certain class of sub-libraries which can be useful in the performance of certain assays. In an illustration of the embodiment of this invention, in order to perform an assay for detecting the presence of a nucleic acid of interest, one would provide the applicable functional site to enable the coupling of one or more oligonucleotide or cDNA. In another illustration of the embodiment of this invention, to perform an assay for detecting the presence of a protein of interest, one would provide a functional site to enable the coupling of one or more antigen or antibody which are specific to the detection or modulation of the protein of interest. Such functional coupling can be accomplished prior to or following forming the composite particles of the invention.

Generally, the foregoing functional and coupling groups can be attached to the outside surface of the magnetic nanoparticle by covalent attachment using known methods in the art. Following formation of the site of interest on the magnetic nanoparticles, the sub-library of magnetic nanoparticles can be brought in contact with the sub-library of encoded particles and the magnetic nanoparticles can be caused to attach to the encoded particles through the coupling site using known method in the art, while leaving the functional site unattached and available for the performance of assay of interest.

In another application of the invention, as illustrated in the following Examples, the metal oxide loading of the composite particles of the invention can be controlled and adjusted so as to induce a magnetic response of interest. The foregoing can be accomplished by controlling the number of magnetic nanoparticles which bind to the surface of the encoded particle.

In another application of the invention, as illustrated in the following Examples, the optical identifier in the encoded particles can be incorporated in specified ratios to accomplish the objectives of the application of interest. The control of the ratio of the optical identifier can be accomplished using known methods in the art such as for example the method disclosed in U.S. Pat. No. 4,717,655.

Following customization of the sub-library of magnetic nanoparticles, as illustrated in the following Examples, a library of composite particles can be formed by covalently attaching a multitude of functionalized magnetic nanoparticle to the outer surface of an encoded particle, the properties of the particles being pre-selected depending on the assay to be performed. AS exemplified herein, the chemical diversity represented in the library of the composite particles of the invention is greater than 2. In another embodiment, the composite particles of the invention may be produced during execution of the assay itself. The assay invokes the binding interaction between one functional group displayed on a magnetic nanoparticle of the invention and a second molecular group displayed on the encoded particle of the invention to produce the composite particle of the invention. In the course of the assay, heterostructures composed of magnetic and non-magnetic particles can be formed as a result of the formation of a complex between functional and molecular groups following which the composite particles of the invention can be arranged into array format for detection.

The composite particles of the invention can be manipulated on a substrate which may be patterned in accordance with the interfacial patterning methods disclosed in U.S. Pat. No. 6,251,691. Following patterning, arrays of the composite particles of the invention can be prepared utilizing the "sandwich" configuration.

The composite particles of the invention can also be manipulated and assembled into ordered arrays in response to magnetic fields. The presence of magnetic field gradients induces a force on the composite particles ($\sim \frac{1}{2}(\chi V/\mu o)$del ($B^2$)), where $\chi$ the magnetic susceptibility of a composite particle, V its volume, B magnitude of the magnetic field (flux density)) the direction and magnitude of which depends on the exact nature of the magnetic field distribution and the strength of the magnetic field. A proper combination of an uniform axial field and localized field gradient generating structures can be used to capture and immobilize (reversibly) the composite particles of the invention in an array format. Such a capability of being able to form 2D arrays as well as immobilize such particles has particular applicability in connection with the performance of multi-step assays involving buffer exchange and multiple wash steps. A particularly useful structure for generating a uniform axial as well as tunable gradient in the vertical direction is a pair of electromagnetic coils such that their individual field directions oppose each other. Hence by adjusting the gap between the coils or the relative position of the sample with respect to the coils and by varying the individual currents in the coils, the force on the composite particles of the invention ($\frac{1}{2}(\chi V/\mu o)$ BdB/dz can be controlled.

As a function of increasing magnetic field strength, ordered planar assemblies of field-dependent number density (or equivalently, average inter-particle distance) and linear strings of beads oriented normal to the substrate can be formed.

In a preferred embodiment, planar structures are formed at or near a substrate by application of a uniform magnetic field oriented normal to the substrate plane. For typical values of magnetic susceptibility of composite particles with an average diameter of 3.2 μm, prepared as described in Examples provided herein, a field producing a magnetic induction in the range of approximately 1,000 to 2,000 Gauss suffices to produce planar assemblies. Permanent magnets are available which, when placed in immediate proximity to the substrate, generate a field near the substrate surface of sufficient field strength to realize the desired planar configuration of the assembly. Requisite magnetic fields configurations also can be produced by an electromagnet, for example in solenoid or Helmholtz configuration known to the art; the substrate can be introduced into the magnet bore or can be placed in immediate proximity to the coil(s) outside of the bore so as to ensure the orientation of the field substantially normal to the substrate plane. The magnetic field generated in such arrangements increases with the current applied to the coils(s) of the electromagnet, thereby providing for the application of magnetic fields which vary in time, for example in the form of a linear ramp (for current increasing linearly in time) or sinusoidally (for current varying sinusoidally as a function of time, i.e., an AC current).

Given the field-dependence of the number density within the planar assembly or array, an electromagnet configuration, via real-time control of the current, thus provides a means to reversibly adjust the number density of the assembly in real time. In a preferred embodiment, an AC current, with frequency in the range 10 Hz to 10 MHz, and more typically in the rage of 10 Hz to 10 kHz, is superimposed on a DC current, the amplitude of the AC current chosen to be small compared to the magnitude of the DC current: the former provides a temporal variation of interparticle distance within the assembly while the latter sets the average density. This induced density variation of the planar assembly will set up an electrokinetic response and local flow in the surrounding fluid medium. This magnetic field-induced flow has utility, for example by providing local mixing to enhance the kinetics of any reaction of interest occurring near the substrate and/or near the particle surface. In addition, spatially modulated magnetic fields can be produced by patterning the substrate with perm-alloy using methods known to the art.

The invention discloses a platform for the implementation of multistep bioanalytical assay procedures using the libraries of the composite particles of the invention to integrate multiplexed molecular interaction analysis with sample preparation and processing steps. Sample preparation may include capture and separation of desired analytes from a given mixture, and sample processing may include any desired transformations carried out on captured analytes and/or binding agents. Analysis typically may include the detection and recording of indicators of the degree of molecular interaction between bead-displayed binding agents and analyte molecules, an optical signature such as fluorescence or chemiluminescence representing a typical example of such an indicator; in addition, analysis may include the in-situ decoding the identities of binding agents associated with individual particles.

In each particular library of the present invention, a binding agent of interest in a desired assay is associated with a distinguishable tag in the form of a color-code. Of specific interest to the present invention are sub-libraries of encoded particles which enable real-time decoding, and hence the determination of the chemical identity of the binding agent. In the present invention, pre-selected binding agent are separately attached to the magnetic nanoparticles of the invention, to produce a sub-library of functionalized magnetic nanoparticles, and this sub-library is combined with a separately prepared sub-library of encoded particles serving as bead tags so as to uniquely associate to each functionalized magnetic nanoparticle contained in the first sub-library. This process provides unique flexibility in controlling the composition and possible permutations of functional groups and tags in the resulting library.

In one embodiment of the present invention, a library of the composite particles of the invention can be utilized in conjunction with standard microwell format and liquid handling robotics. The microwells contain a set of particles selected from the library in accordance with the requirements of the assay of interest. Multiplexed interaction analysis can be performed in one or more wells or other equivalent reaction vessels, preferably under conditions ensuring that the composite particles of the invention remain in suspension in order to achieve favorable reaction kinetics and maintain optimal mixing of the reaction. Each of the composite particles present in the reaction is able to interact with the same mixture of analyte molecules so as to facilitate the simultaneous formation of multiple binding agent complexes in this multiplexed assay format in a manner described in the Examples set forth herein. Following completion of the molecular interaction and formation of binding agent complexes on the individual particles, within the set contained in each reaction vessel, the particles are analyzed and decoded, for example, by utilizing flow cytometry in a serial mode of analysis, to decode the particles and record assay signals one particle at a time, or by transferring one or sets of particles to substrates permitting the formation of planar assemblies for example by permitting the particles to settle under gravity.

In a preferred embodiment, assay integration is achieved in a microfluidic environment that eliminates the microwell format. As discussed below, sample capture, subsequent transformations of bead-displayed binding agents or analytes and real-time formation of random encoded assemblies of encoded particles subsequent to completion of the binding interaction, the latter permitting instant imaging detection in accordance with the READ process, are all integrated in a highly parallel assay format. A random encoded bead array, composed of the composite particles of the invention formed in real-time by application of a magnetic field in accordance with the present invention, provides a platform which can be used to perform multi-step assay sequences.

Figure 22:
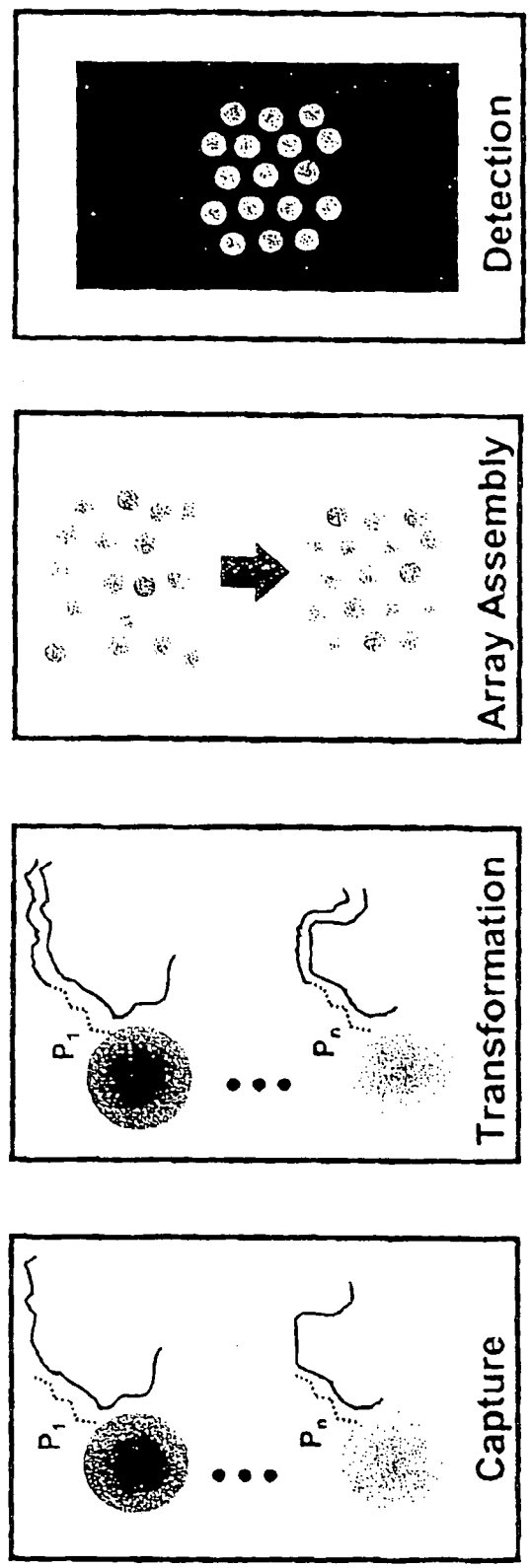
FIG. 22 is an illustration of multi-step assay sequence having applicability to a wide range of biochemical assays.

For purposes of illustration of the invention, four sets of steps (namely capture, transformation, post-transformation array assembly and random encoded array detection) can be carried as shown in FIG. 22. These steps are further illustrated in the Examples that follow and provide the ability to perform an integrated bioanalytical assay. The assay protocol may be implemented in a microfluidic device of standard design, composed of one or more fluidic compartments connected by fluidic conduits and providing for the timed transport of aliquots of fluids using standard methods of pumping. In a preferred embodiment, sample capture and transformation are performed in a first compartment; following transformation, beads are transferred to a second compartment equipped with a magnetic field to complete post-transformation assembly and the READ process.

Sample of interest and a customized set of the composite particles are introduced into a first compartment and allowed to interact so as to permit capture of analytes from the sample to bead-displayed binding agents. Following application of a magnetic trap, one or more washing cycles are performed which involve the replacement of the content of the first compartment by aliquots of fresh buffer and finally, to initiate the transformation step, the introduction of an aliquot of reagents required for the transformation reaction, as described in the Examples provided herein.

The following describes in more detail the four steps of the process of the invention.

1. Capture

The analysis of biological samples typically begins with complex mixtures such a blood, serum or cell suspensions that contain not only the analytes of interest, be they antibodies, antigens, RNA, DNA or other biomolecules, but also a great variety of constituents which may interfere with the intended analysis. As with standard analytical chemical separation, it is generally desirable if not necessary to separate the analyte fraction of sample from the remainder. The suitability of certain magnetic particles for this purpose has been widely documented in the prior art, said particles, when used in the microwell format, generally requiring a high magnetic susceptibility to permit their collection and immobilization within reasonable time in magnetic field gradients which may be generated in a laboratory setting by use of permanent magnets. In this step, the capture of functional groups of interest, including, for example, genomic DNA fragments and the like to a first set of magnetic particles can be accomplished. The capture step is immediately followed by one or more wahing cycles involving the introduction of fresh buffer to replace mobile (non-imobilized) constituents of the original mixture. Inductive elements also have been described to produce magnetic fields and field gradients within a miniaturized environment.

In certain instances, it may not be necessary to distinguish between different types of analytes of interest; examples include the extraction of total mRNA from cell lysate by hybridization of the common poly-A tail sequence to oligo-dT displayed on standard magnetic particles or the affinity purification of a class of antibodies, say IgG, by binding of the Fc portion of the molecule to bead-displayed protein A, as in standard affinity purification.

However, in many instances, it is desirable or necessary to capture multiple analytes from a given sample in an analyte-specific manner. In the absence of a library of the composite particles of the invention, the sample require splitting into multiple aliquots, an additional step which not only has the potential to introduce inaccuracies such as pipetting error or contamination, but require the use of prohibitively small amounts of available sample. In contrast, libraries of the composite particles of the invention facilitate multiplexing by way of simultaneous capture in an analyte-specific manner. Examples include the sequence-specific capture of multiple mRNA targets of interest from cell lysate to matching bead-displayed capture sequences; the selection of multiple cDNA targets from a cDNA library; or the capture of multiple rare types of lymphocytes, identified by their respective repertoire of expressed cell surface antigens, to bead-displayed monoclonal antibodies. As described in Example 25, sample introduced in the specific capture step can be produced in a first, non-specific capture step involving, for example the magnetic nanoparticles of the invention.

In one embodiment of magnetic capture of the composite particles during wash cycles, permanent magnets known in the prior art may be employed to achieve temporary immobilization. Here, miniaturization of the assay environment ensures that particles always reside within a short distance of typically not more than 100 μm from the nearest bounding surface of the reaction vessel, thereby reducing the time required to collect particles of given magnetic susceptibility from suspension into a magnetic gradient, or, conversely, to minimize the requisite magnetic susceptibility to ensure trapping within a given collection time, typically not more than 5 minutes and preferably not more than 0.5 minutes, by a magnetic field and field gradient of given strength. For the composite particles of the present invention, the magnetic susceptibility as determined by the constituents of the shell rather than the core, and they are therefore particularly well suited to miniaturized assay environments.

One embodiment of the present invention may utilize designs of inductive elements known to the art for particle trapping at or near planar substrate surfaces. In a preferred embodiment, capture is performed within a first microfluidic compartment permitting application of magnetic fields. For example, a planar fluidic compartment may be sandwiched between two permanent magnets which are arranged to provide a sufficiently string trap to hold particles against the two bounding surface of the compartment in the presence lateral flow up to a certain rate, but will release them in the presence of higher flow rates; equivalent magnetic field configurations also are readily produced by combination of solenoid magnets. A further alternative is provided by an axially symmetric configuration such as a capillary tube of 10-100 μm diameter which may be inserted into the center of a quadru-polar field to provide trapping.

2. Transformation

The transformation of the captured analytes, or, in some cases relevant to DNA analysis, the analyte-mediated transformation of the bead-displayed probe itself represents an important processing step. Within the context of molecular biology, the most important processing steps involve several well studied enzyme-mediated modifications of RNA or DNA, notably including, in the former case, reverse transcription, and in the latter case, ligation, extension of bead-displayed probes (also known as primers) or amplification by cycling of extension reactions, most prevalently by application of polymerase chain reaction (PCR) protocols well known to the art. Specifically of interest to the present invention are implementations of on-bead RNA and DNA modification reactions. As with the capture step, multiplexing of reactions such as PCR using bead-tagged primers calls for the use of libraries of the composite particles of the present invention. An example is the solid-phase amplification of captured "particle-tagged" fragments. In the transformation step, "particle-tagged" DNA fragments are subjected to a set of "multiplex" transformation steps such as for example PCR amplification. Another example is the polymerase-mediated extension of bead-displayed probe to produce a bead-displayed cDNA strand whose composition is complementary to the captured RNA target In general, it also is possible to create solution-borne products as a result of the transformation which may then be captured to a second set of the composite particles of the invention as exemplified herein.

Captured protein analytes also may be transformed prior to further analysis. For example, proteins modified to contain a histidine derivative may be modified by chelation to nickel-functionalized reagents and tags using methods known to the art.

3. Post-Transformation Array Assembly

The present invention utilizes the magnetic field-induced formation of arrays comprising the composite particles of the invention as a means to produce random encoded assemblies and arrays of particles within the context of a highly bioanalytical parallel assay format in real time following completion of transformation. This process can produce planar assemblies of the composite particles of the invention in designated regions of the substrate surface to facilitate subsequent imaging of assemblies, and can produce such assemblies and ordered arrays under the widely varying conditions ensuring successful molecular interaction analysis and stability of the resulting binding agent complex, these conditions pertaining to buffer formulation (salt concentration, pH), presence of additional constituents such as surfactant or adjuvant, temperature and the like. Finite regions of the substrate can be delineated by interfacial patterning as described in the LEAPS process. In addition, spatially modulated magnetic fields can be produced by substrate patterning using, for example, permalloy in accordance with standard procedures.

The particles of the invention can be assembled into planar assemblies or ordered planar arrays in response to applied magnetic fields. For example, particles provided within suspension in a fluidic compartment bounded by two substantially planar surfaces that are arranged in a mutually parallel configuration in a sandwich geometry, when exposed to a magnetic field oriented in a direction normal to the bounding surfaces, will form a planar assembly. For given particle magnetic susceptibility as controlled by the methods of the invention, ordered planar assemblies of characteristic number density will form in response to increasing magnetic field strength; in addition, linear strings of beads oriented normal to the substrate (and hence substantially parallel to the applied field) can be formed.

The application of suitably designed magnetic fields generated by a configuration of permanent magnets or electromagnets are well known in the art. Permanent magnets can be designed so as to produce the field strength required to realize the desired configuration of the assembly. Requisite magnetic field configurations can be produced by an electromagnet, for example in solenoid or Helmholtz configuration known to the art; the substrate can be introduced into the magnet bore or can be placed in immediate proximity to the coil(s) outside of the bore so as to ensure the orientation of the field substantially normal to the substrate plane.

In another embodiment, a magnetic trap of the type described in connection with the capture step can be employed to exchange the buffer employed for molecular interaction analysis for a second buffer that is optimized to realize conditions ensuring rapid array assembly by application of LEAPS.

4. Random Encoded Array Detection

Once assembled, the random encoded array of the composite particles of the invention may be imaged to record assay signals and may be decoded to identify binding agents associated with individual beads within the array by the methods and procedures described herein.

Following formation of an array with the composite particles of the invention, the array provides a platform which can be used to read the results of the multi-sep assay sequences. The methods disclosed herein permit rapid customization of DNA or protein arrays without the need for process redesign and avoid problems contributing to spot-to-spot as well as chip-to-clip variability. Furthermore, the particle array format permits chip-independent characterization of particles as well as optimization of assay conditions. In addition, multiple particles arrays can be formed simultaneously in discrete fluid compartments maintained on the same chip, permitting the concurrent processing of multiple samples.

In order that the invention described herein may be more fully understood, the following examples are set forth. It should be understood that these examples are for illustrative purposes and are not to be construed as limiting this invention in any manner.

EXAMPLES

Example 1

Optically Programmable Array Formation

Figure 9:
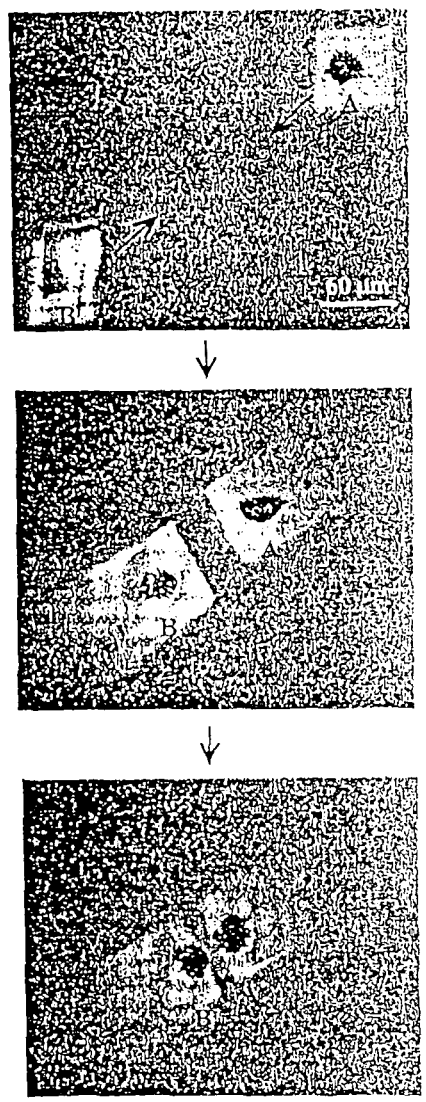
FIG. 9 is an illustration of optically programmable array assembly of random encoded arrays.

As illustrated in FIG. 9, LEAPS serves to simultaneously assemble multiple random encoded subarrays and to "drag-and-drop" these subarrays into separate, but proximate locations on the chip within a common, enclosed liquid environment. Two sets of beads (2.8 μm Oligo-(dT)$_{25}$, Dynal, Oslo, Norway), dispensed from separate reservoirs A and B, were simultaneously assembled into distinct subarrays within the same fluid; sub-arrays were then simultaneously placed into desired destinations as directed by spatially varying illumination profiles which were generated and projected onto the substrate by a PC-programmable illumination pattern generator (described in U.S. Ser. No. 09/397,793, filed Sep. 17, 1999, which is incorporated herein by reference in its entirety). This drag-and-drop operation reduced the separation between the two sub-arrays from approximately 250 μm to 20 μm. Beads were moved at 5 V$_{pp}$ at a frequency of 2 kHz; total power projected onto the substrate surface was ~5 mW. The combination of chemical and spatial encoding permits a given set of chemical bead markers to be used multiple times and reduces the demands placed on either encoding dimension while facilitating the realization of large coding capacities.

Example 2

Array Formation on Patterned Surface

Figure 10:
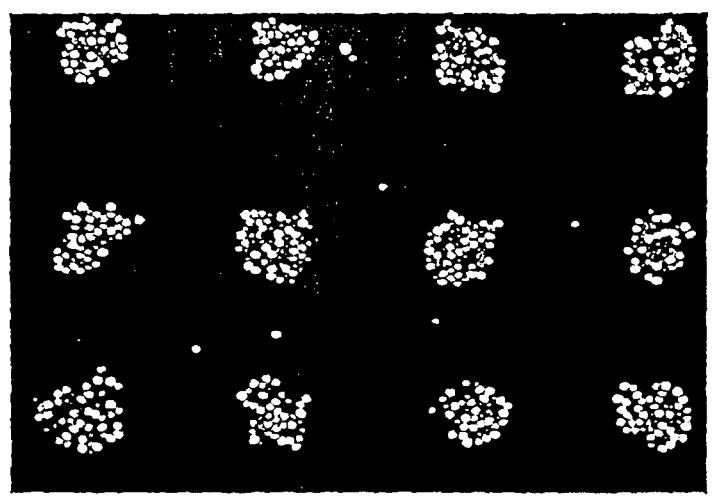
FIG. 10 is an illustration of an array composed of random encoded subarrays.

Illustrated in FIG. 10 is an array of encoded beads assembled on a patterned silicon chip using an AC voltage of 1-2 $V_{pp}$ and a frequency of 100-150 Hz, applied across a 100 µm electrode gap filled with an aqueous bead suspension; a thermal oxide (~1000 Å) on the substrate was patterned by etching the oxide to a thickness of 50-100 Å in a set of square features (~30×30 µm$^2$) on 130 µm centers; arrays of similar layout also can be produced in response to suitable illumination patterns. Each sub-array shown here contains approximately 80 beads coupled with anti-cytokine monoclonal antibodies. Carboxylate-modified polystyrene beads of 5.5 µm diameter (Bangs Laboratory, Fishers, Ind.) were stained with a combination of two types of fluorescent dyes and were then functionalized with anti-cytokine-mAb. The assembly process ensures collection of all beads at the substrate surface. Bead encoding was as follows: IL-2 (Bright Red); IL-4 (Dim Red); IL-6 (Bright Green); M-CSF (Dim Green) and TNF-α (Yellow).

Example 3

Formation of Arrays of Magnetic Nanoparticles

Colloidal particles exhibiting a finite diamagnetic susceptibility, when disposed on a planar substrate can be assembled into ordered arrays in response to increasing magnetic fields. Commercially available superparamagnetic particles (Dynal, Oslo, NO), dispersed from a fluid suspension onto the planar surface of the lower of two parallel bounding surfaces of a fluid cell ("sandwich" geometry), when exposed to a homogeneous axial magnetic field (oriented normal to the substrate plane), will form ordered assemblies. As a function of increasing magnetic field strength, and for given diamagnetic susceptibility of the particles as controlled by the manufacturing process known to the art, ordered planar assemblies and linear strings of beads oriented normal to the substrate can be formed. Permanent magnets can be designed so as to produce the field strength required to realize the desired configuration of the assembly. Requisite magnetic field configurations can be produced by an electromagnet in solenoid or Helmholtz configuration known to the art; the substrate can be introduced into the magnet bore or can be placed in immediate proximity to the coil(s) outside of the bore so as to ensure the orientation of the field substantially normal to the substrate plane. Spatially modulated magnetic fields can be produced by patterning the substrate with permalloy using methods known to the art.

Example 4

Formation of Random Bead Assemblies

Aliquots of solution containing suspended beads were placed onto several distinct positions on a planer substrate of silicon capped with a thin silicon oxide layer (other substrates may be used here). Beads were allowed to settle under gravity to form random assemblies. To delineate discrete positions on the substrate, one of the following two methods were used. According to the first method, a silicon gasket (of 250 um thickness), displaying a grid of multiple round holes of 1 mm or 2 mm diameter (Grace Bio-labs, Bend, Oreg.) is placed on the hydrophilic surface to define microwells (of 0.25 to 0.5 ul volume) for multiple discrete samples of bead suspension. According to the second method, small aliquots of fluid containing beads (0.2 ul to 0.5 ul in volume) are directly placed onto a hydrophilic surface in one or more designated areas so as to ensure formation of discrete droplets; spacers are not needed in this case. As solvent evaporates (at room temperature or, for rapid drying, at elevated temperature (about 60 C), beads are left in random positions on the substrate. DNA polymorphism reactions have been tested in assemblies formed in both manners. Optionally, beads settling under gravity may be immobilized by chemical capture layers provided on the substrate. An application of random bead assemblies to determine affinity constants in a multiplexed format is described in Example 6.

Example 5

An Automated Chip-Scale Array Manufacturing Process

Figure 11:
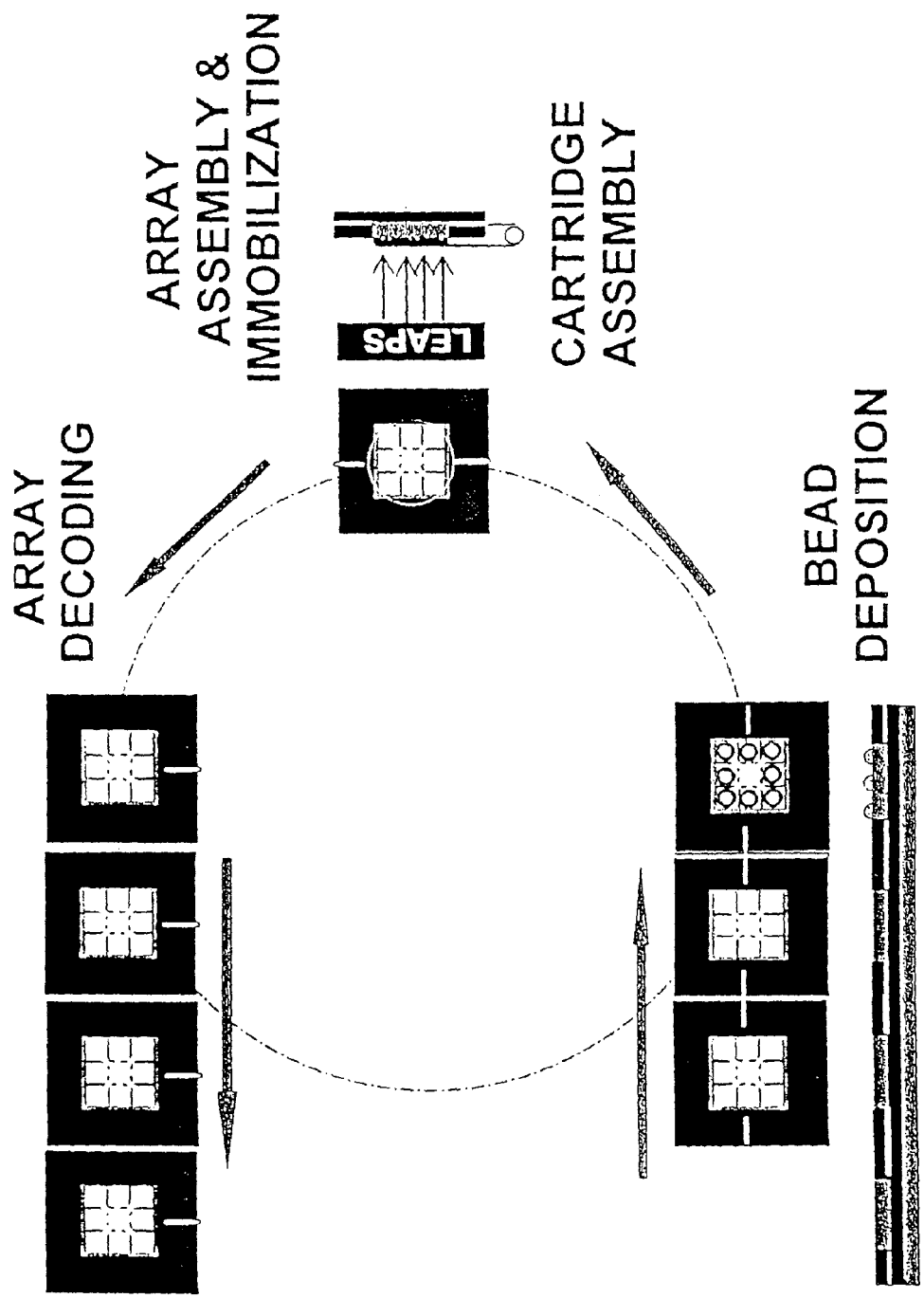
FIG. 11 is an illustration of stations in an automated chip-scale bead array manufacturing and quality control process.

As illustrated in FIG. 11, the process involves liquid handling and pipetting of beads onto chips mounted in single-chip cartridges or multi-chip cartridges. Bead arrays are formed using methods such as those in Examples 1, 2 or 3, followed by array immobilization and decoding. The resulting decoding images are stored for later use along with an optional chip ID ("bar code").

Example 6

Determination of Affinity Constants by Post-Assay Analysis of Bead Assemblies Quantitative binding curves for the cytokines TNF-α and IL-6. Binding curves were generated by performing sandwich immunoassays using chemically encoded beads in suspension, said suspensions being confined to one or more reaction compartments delineated on-chip, or in one or more reaction compartments off chip. By completing the reaction with beads maintained in suspension, assay kinetics similar to homogeneous assays can be attained. Following completion of the binding reaction, beads were assembled on chip to permit multiplexed quantitative image analysis. Random assemblies prepared according to Example 4 or ordered bead arrays prepared according to Example 1 or 2 may be used. An advantage of ordered, dense assemblies produced by the methods of Examples 1 or 2 is the higher spatial density and higher assay throughput attained by processing a greater number of beads.

Figure 12:
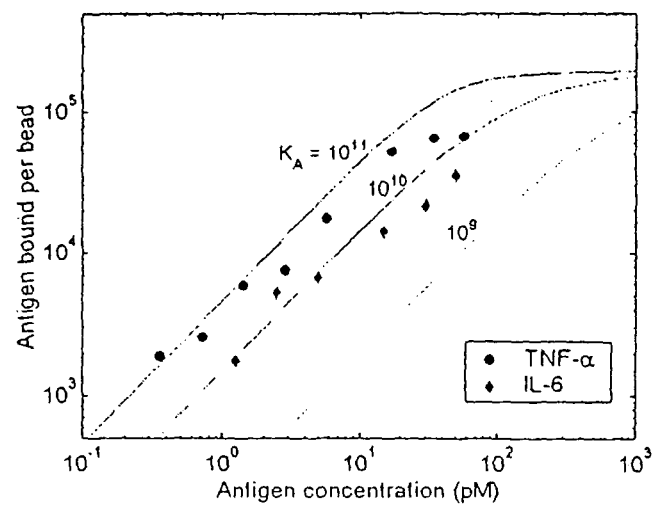
FIG. 12 is an illustration of quantitative binding curves for two cytokines.

As an illustration, FIG. 12 displays quantitative binding curves for TNF-α and IL-6, obtained from randomly dispersed beads. A commercial-grade 8-bit video-CCD camera (Cohu, San Diego, Calif.) was used in a mode permitting multi-frame integration. The range of concentrations of antigen used in the two assays was 700 fM to 50 pM for TNF-α and 2 pM to 50 pM for IL-6. At each concentration, the number of molecules bound per bead was estimated by comparison with calibration beads coated with known quantities of Cy5.5-labeled BSA per bead; requisite adjustments were made to account for differences in fluorescence quantum efficiency between labeled secondary antibodies and BSA.

This format of analysis permits the determination of the affinity constant, $K_A=[LR]/([R_O-LR][L])$, where, in accordance with the law of mass action, [LR] denotes the number of receptor-ligand pairs per bead and [L] denotes the solution concentration of ligand. By specifying the number of beads per ml, $n_B$, and specifying a value for $[R_O]$ in terms of the number of receptors per bead, theoretical binding curves, computed for given $K_A$, are compared to a plot of the number of bound molecules per bead as a function of bulk ligand concentration. The absolute number of ligands bound per bead may be determined for given bulk concentration by measuring the mean fluorescence intensity per bead and referencing this to the fluorescence intensity recorded from calibration beads included in the array.

The estimated number of molecules bound per bead is compared to theoretical binding curves derived from the law of mass action. The three curves shown correspond to values of the affinity constant, $K_A$, of $10^{11}$/molar, $10^{10}$/molar and $10^9$/molar, respectively. The initial number of antibodies per bead, $R_0$, equals $2\times10^5$/bead and $n_B=10^5$/ml. Each data point represents the average of three replicates, with an assay-to-assay variation of <45%. Setting the assay sensitivity to correspond to that level of fluorescence which yields a signal-to-noise level of unity in the assay images, the sensitivity of the cytokine assays characterized in FIG. 12 is set at ~2,000 bound ligands/bead, corresponding to respective detected concentrations of 700 fM for TNF-α and 2 pM for IL-6.

While commercial ELISA kits use enzymatic amplification to enhance sensitivity, at the expense of additional complexity relating to assay conditions and controls, our bead array assay format, even without enzymatic amplification, our on-chip assay format permits monitoring of cytokines at circulating levels (Normal TNF-α level in serum is 50-280 fM and normal IL-6 level in serum is 0-750 fM. www.apbiotech.com/technical/technical_index.html), providing a dynamic range which approaches that of standard, i.e. amplified single-analyte ELISA assays (Assay kits of R & D Systems and Amersham (not the recent High-Sensitivity assays). Further improvements at hardware and software levels are possible.

Example 7

Genotyping by Polymorphism Analysis

Figure 13:
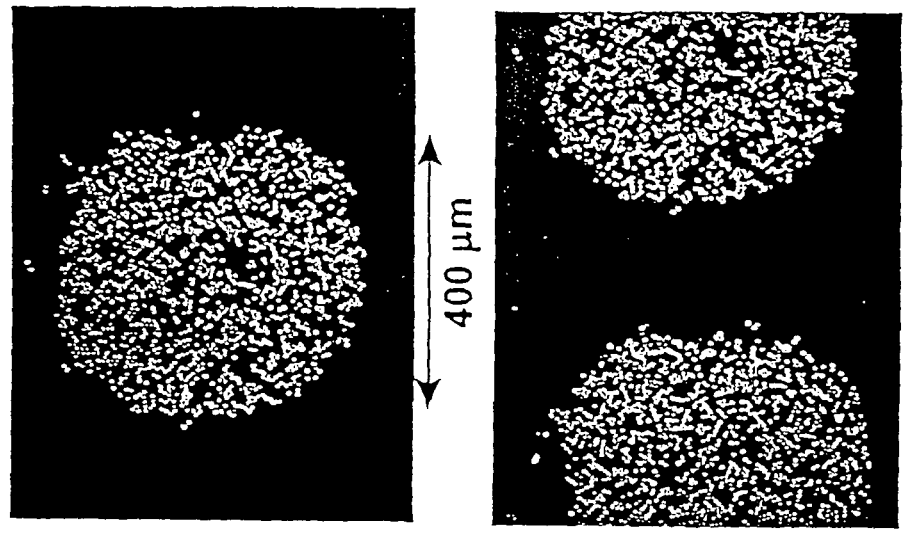
FIG. 13 is an illustration of array design for polymorphism analysis.
Figure 13:
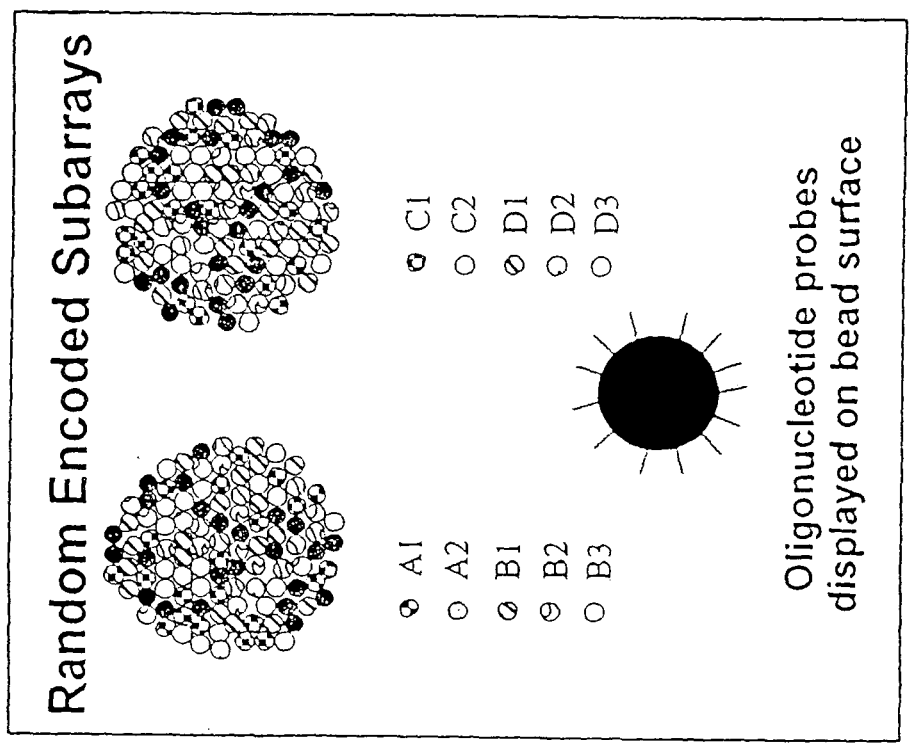

To illustrate the application of the present invention to the implementation of genotyping, FIG. 13 shows the design of the assay in which five pairs of 20-mer binding agents corresponding to four polymorphic regions of a gene were coupled to color-encoded beads. The pairs of binding agents α1, α2 and β1, β2 each display a single nucleotide difference in their respective sequences; the pair δ3, δ4 displays a difference of three nucleotides, the binding agents in the set γ1, γ3, γ3, γ4 display small insertions and deletions. The ten binding agents were are divided into two subgroups of five which were incorporated into two subarrays. In this example, there are several hundred beads for each type. Following bead immobilization, an on-chip hybridization reaction was performed in TMAC buffer (2.25 M tetramethylammonium chloride, 37 mM Tris pH 8.0, 3 mM EDTA pH 8.0, and 0.15% SDS) at 55° C. for 30 min. The analyte is a 254-base PCR fragment produced from a patient sample and fluorescently labeled at the 5'-prime end with BODIPY 630/650 (Molecular Probes, Eugene, Oreg.). Image acquisition was performed after replacing the assay buffer with fresh TMAC buffer.

Figure 14:
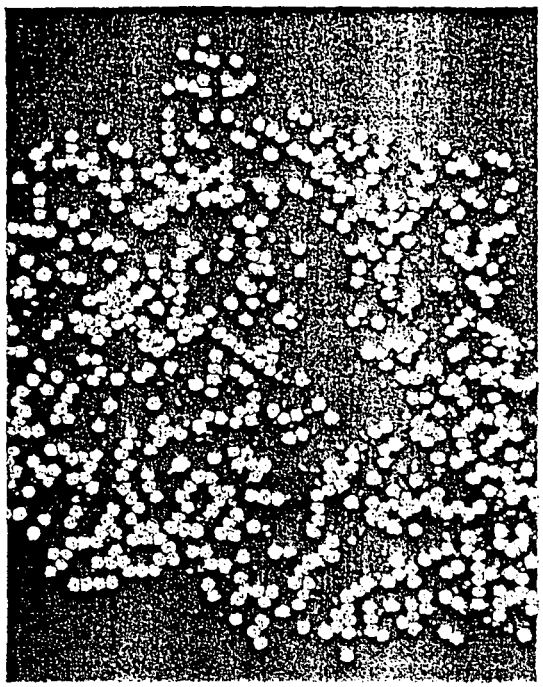
FIG. 14 is a fluorescence micrograph of assay and decoding images recorded from one subarray shown in FIG. 13 in the course of polymorphism analysis
Figure 14:
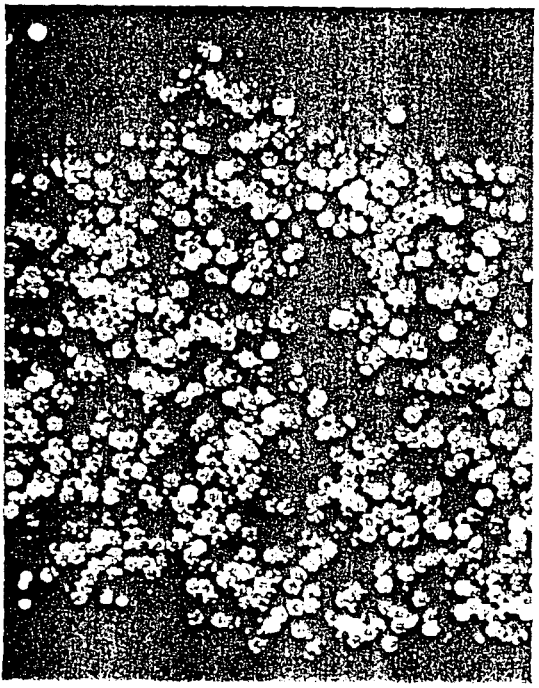
Figure 15:
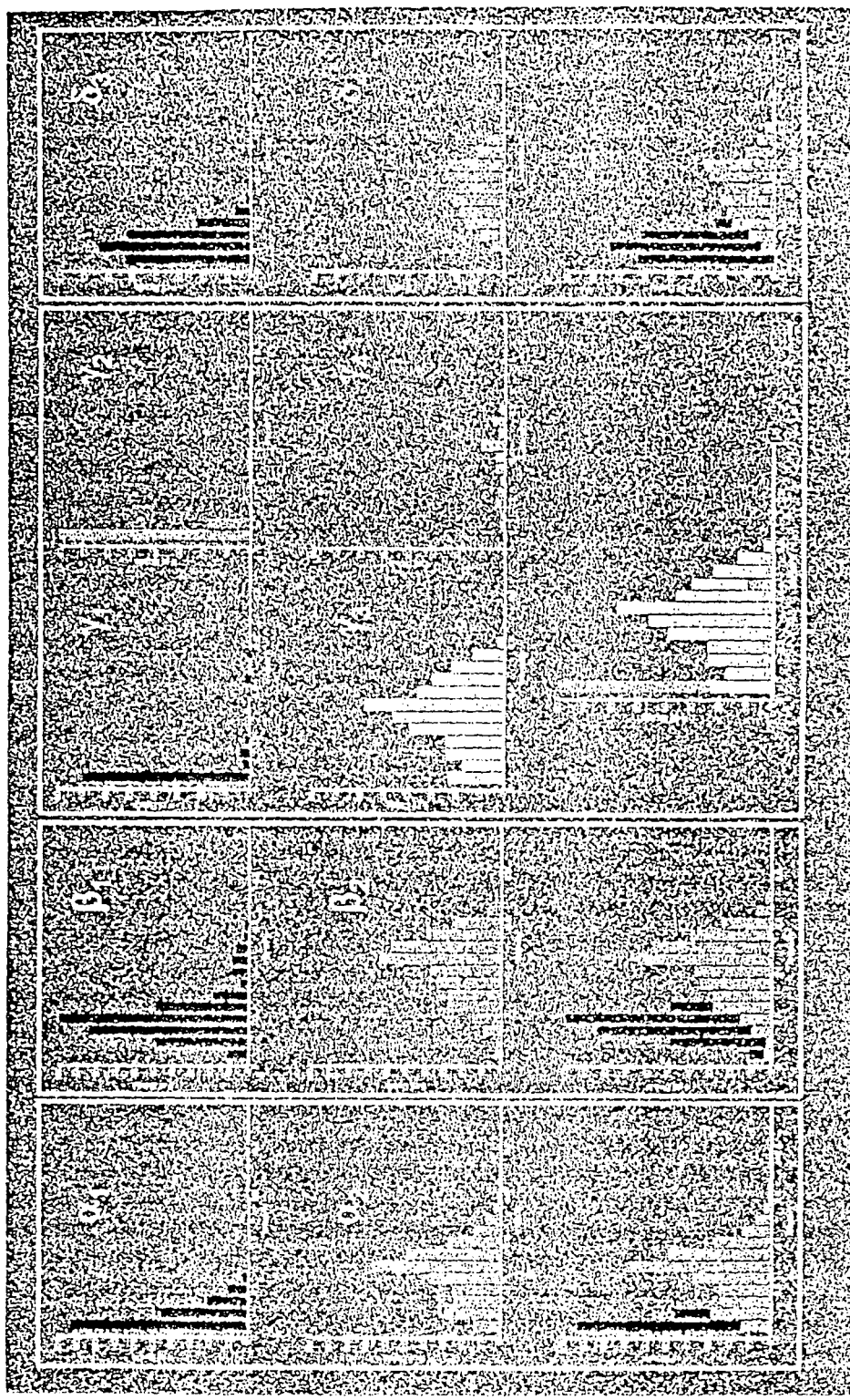
FIG. 15 is an illustration of assay results in the form of intensity histograms obtained from the analysis of assay images such as the one illustrated in FIG. 14.

FIG. 14 shows decoding and assay images for one subarray. Each bead shown in the assay image obtained after hybridization is analyzed to determine fluorescence intensity and bead type; as with the cytokine assay, the latter operation compares assay and decoding images using a template matching algorithm. FIG. 15 displays the resulting intensity histograms for each bead type: in these histogram plots, the horizontal axis refers to relative signal intensity from 0 to 1 and the vertical axises refer to bead numbers. The histograms show that most of the beads displaying probe α1 bind no analyte while most of the beads displaying probe α2 exhibit significant binding; the mean signal level of α2-beads exceeds that of α2-beads by a factor of ~3.2, indicating that analyte contains DNA sequences complementary to α2 but not α1. For the patient sample presented here, the histogram indicates a genotype of the analyte DNA characterized by complementarity to binding agents α2, β2, γ3, γ4 and δ4 in the polymorphic region of the gene.

Example 8

Gene Expression Analysis: cDNA Fragments

The method of the present invention has been used to fabricate arrays composed of beads displaying oligonucleotides as well as DNA fragments (e.g., up to ~1,000 bases in length). Strands were biotinylated at multiple positions by nick-translation and were attached to streptavidin-functionalized beads (M-280, Dynal, Oslo, NO). Arrays were formed using an AC voltage of 800 Hz at $10V_{pp}$.

Example 9

Looped Probe Design for Universal Lbeling

Figure 16:
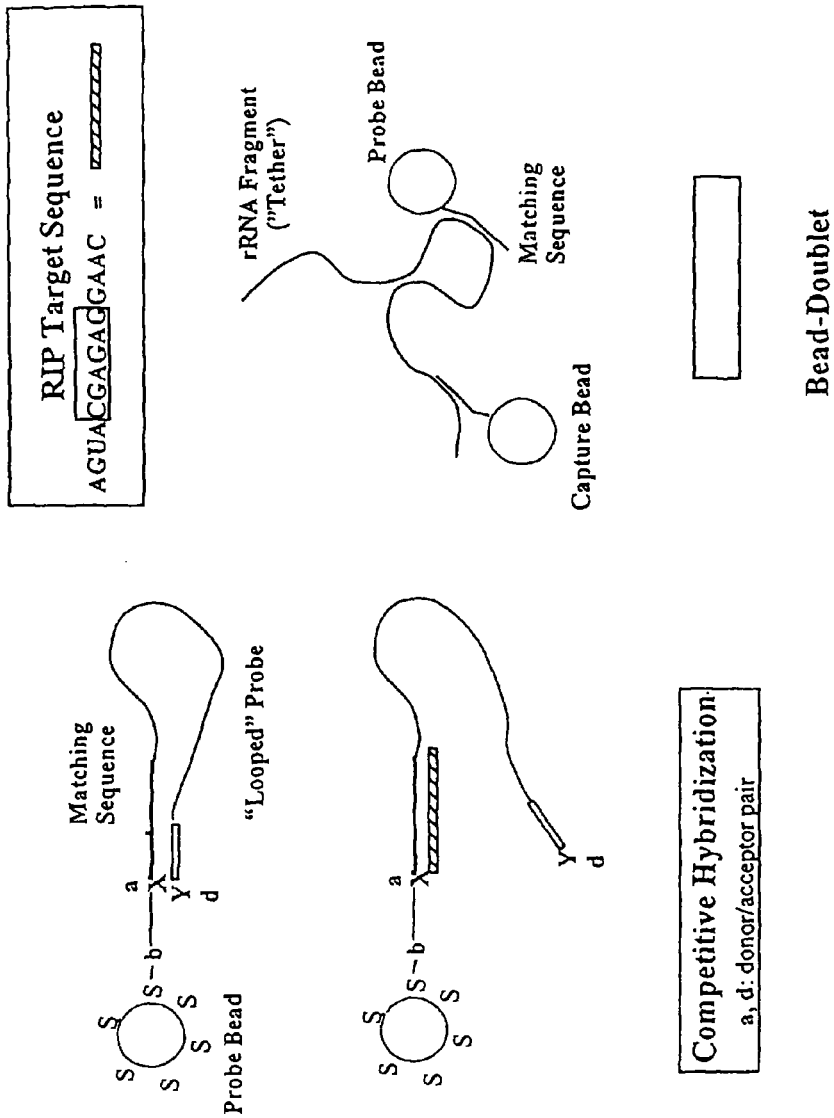
FIG. 16 is an illustration of design of a "looped probe" for hybridization assays.

A looped probe design in FIG. 16 takes advantage of fluorescence energy transfer to obviate the need for labeled target. As with the molecular beacon design (S. Tyagi, D. P. Bratu. F. R. Kramer, Nature Biotech. 16, 49-53 (1998)), the probe in FIG. 16 assumes two different states of fluorescence in the closed loop and open loop configurations, but in contrast to the molecular beacon contains a portion of its binding motif within the stem structure to permit molecular control of stringency in competitive hybridization assays.

Example 10

Quantitative Multiplexed Profiling of Cytokine Expression

Figure 17:
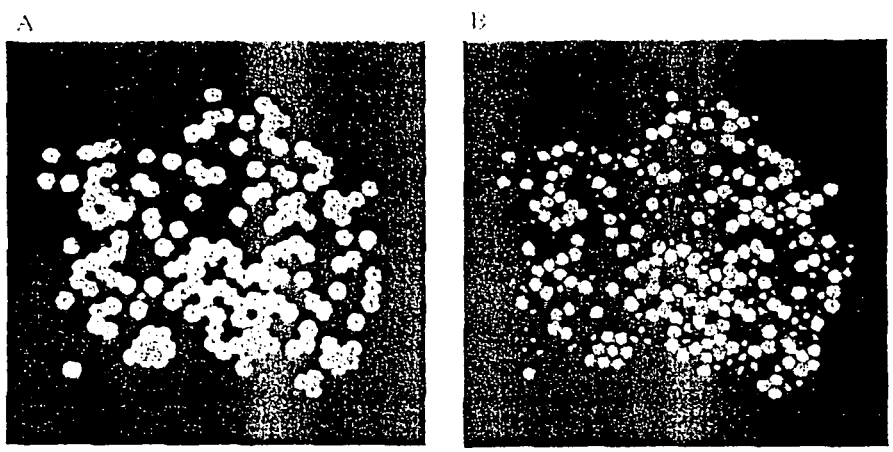
FIGS. 17A and 17B are fluorescence micrographs of assay and decoding images recorded in the course of the analysis of multiple cytokines.

FIG. 17 displays a pair of assay and decoding images recorded from a single random array in a multiplexed sandwich immunoassay. An array containing five distinct types of beads, each displaying a monoclonal anti-cytokine antibody (mAb), was exposed to a sample solution (such as serum) containing two cytokine antigens (Ag). Subsequent addition of Cy5.5-labeled secondary antibodies (pAb*) results in the formation of ternary complexes, mAb-Ag-pAb*. The on-chip immunoassay was performed by adding 300 μl of sample with 7 nM cytokines in assay buffer (20 mM NaPi pH 7.4, 150 mM NaCl, 10 mg/ml BSA) to the bead array immobilized on the chip, and allowing the reaction to proceed at 37° C. for one hour. The buffer was replaced by adding 12 nM solution of labeled secondary antibodies in assay buffer. After one hour of incubation at 37° C., fresh buffer was added on top of the chip and image acquisition was performed. Antibodies and antigens used in the assays were obtained from R&D Systems (Minneapolis, Minn.); the secondary antibody was labeled with Cy5.5 using a standard kit (Amersham Pharmacia Biotech, Piscataway, N.J.).

The decoding image FIG. 17B shows five types of beads in a false-color display with the same encoding pattern as that of FIG. 10. All beads are of the same size (5.5 μm diameter); the apparent difference in the size of beads of different types in the decoding image is an artifact reflecting different internal bead staining levels and "blooming" during CCD recording of the decoding image. Comparison (using the image analysis methods disclosed herein) of the decoding image with the assay image in FIG. 14A reveals that active beads, of yellow and bright green types, captured TNF-α and IL-6, respectively. This assay protocol has been extended to the following set of twelve cytokines: IL-1α, IL-1β, IL-2, IL-4, IL-6, TGF-β1, IL-12, EGF, GM-CSF, M-CSF, MCP-1 and TNF-α. The on-chip immunoassay requires no additional washing other than changing reagent solutions between assay steps. Comparison between assay and decoding images shows that two different cytokines were present in the sample, namely IL-6 and TNF-α. The pre-formed arrays described in this example also permit the determination of affinity constants in a manner analogous to the analysis described in Example 6.

Example 11

Aptamers for Protein Profiling

Aptamers may be selected from large combinatorial libraries for their high binding affinities to serum proteins (L. Gold, B. Polisky, O. Uhlenbeck, M. Yarus, Annu. Rev. Biochem. 64: 763-797. (1995)). Random encoded arrays of aptamer-functionalized beads would serve to monitor levels of serum proteins; correlations in binding patterns on the array (see also Example 10) may serve as a phenotype of disease states.

Example 12

Mixed DNA-Protein Arrays

Of significant interest to genomic functional analysis is the fact that the method of the present invention accommodates protein and DNA arrays without change in array manufacturing methodology. Specifically, mixed arrays composed of beads displaying DNA and corresponding proteins can be used to analyze the gene and gene product within the same fluid sample.

This has been demonstrated for a combination of immunoassay and DNA hybridization. For example, a mixed array composed of beads functionalized with anti-cytokine monoclonal antibodies (mAb) and with oligonucleotides was produced. Two sequential assays were performed on this single chip. First, an immunoassay was performed in accordance with the protocol described in Example 10. Following completion of the on-chip immunoassay, image is acquired and the DNA analyte was added to the hybridization buffer (2×SSC, 1×Denhardt's) at a final concentration of 20 nM and allowed to react at 37° C. for 1 hr. Fresh hybridization buffer was added to the chip and image acquisition was performed to record of the additional hybridization assay.

Example 13

Affinity Fingerprinting

The analysis of receptor-ligand interactions relevant to prior art methods assumes ideal specificity. That is, only the ideal situation is considered of a single ligand present in solution reacting with its matching receptor and vice versa. However, in most multiple assay systems, a considerable level of cross-reactivity may exist. That is, any single ligand may associate with several receptors, while any single type of receptor may have a finite affinity towards more than one ligand.

The present invention includes a model that is developed to analyze multiplexed READ assays for such a system under the following assumptions: each of these reversible reactions is characterized by its own affinity constant; no reaction occurs between the bulk species; there is no interaction between the complexes formed on the surface. These assumptions can be relaxed, at the expense of increasing the complexity of modeling, by accounting for reactions in the bulk and between the surface species. The standard reaction-diffusion equation for single receptor-ligand pair formation [R. W. Glaser, Anal. Biochem. 213, 152-161 (1993)], is generalized to allow for multiple reactions at each bead surface:

$$\frac{\partial [L_i \cdot R_j]}{\partial t} = k_{on,ij}[L_i]\left([R_{j,0}] - \sum_{n,m}[L_m \cdot R_n]\right) - k_{off,ij}[L_i \cdot R_j] \quad (2)$$

$$\forall i, j, L_i \equiv L_i(t, x, 0)$$

The first term on the right of Eq. (1) describes the association of ligands and receptors into complexes and involves of concentration of free sites on the surface. The second term describes the disassociation of complexes by way of release of ligands, thereby freeing up receptor sites for further reaction. Since a maximum of (i×j) bimolecular complexes can form, there could be as many boundary conditions generated from the above equation. For the equilibrium case, the left hand-side of Eq. (1) is set to zero, and the matrix of coaffinities, $[K_{ij}] = k_{on,ij}/k_{off,ij}$, can then be defined to accommodate cross-reactivities between multiple species in the bulk and on the surface. In a batch reactor under equilibrium conditions, we may solve the system of differential equations to obtain the number of molecules of each ligand bound on beads of each type.

| | | |
|---|---|---|
| $L_1$ | Ligand concentration | 10 pM |
| $L_2$ | Ligand concentration | 100 pM |
| $R_{01}$ | Initial receptor concentration | $1 \times 10^4$/bead |
| $R_{02}$ | Initial receptor concentration | $1 \times 10^4$/bead |
| $n_{B1}$ | Bead number density | $1 \times 10^4$/ml |
| $n_{B2}$ | Bead number density | $1 \times 10^4$/ml |
| [K] | Coaffinity matrix | $[1 \times 10^{11}\ 1 \times 10^9$ $1 \times 10^8\ 1 \times 10^{11}]$ 1/mole |

As an illustrative example, the ligand distribution has been calculated (from the model in Eq (1)) for a reference set of two ligands and two types of receptors immobilized on two different sets of beads. The coaffinity matrix is assumed known for each ligand-receptor combination in the reference set; to investigate the detection of a third ligand, it is assumed here that diagonal elements of the 2×2 matrix, $[K_{ij}]$, are large compared to off-diagonal elements. The presence of a third ligand in the reactor alongside the two original ligands perturbs the equilibria between the various complexes and the reactants in the reference system, and for ligand molecules tagged with fluorescent labels, the intensity observed from the perturbed system differs from that observed in the reference case.

Figure 18A:
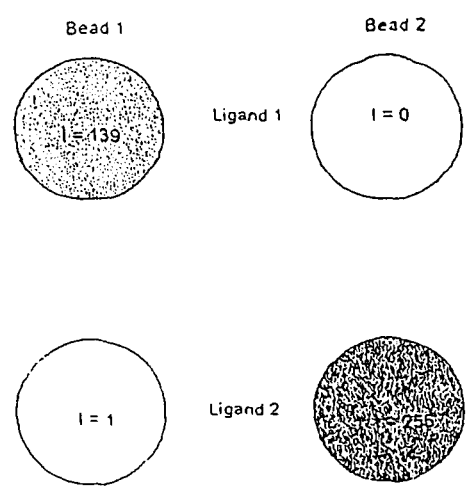
FIGS. 18A and 18B are illustrations of numerical simulations of cross-correlations in receptor-ligand systems with multiple competing receptor-ligand interactions.

FIG. 18A shows the reference case in which the concentrations and coaffinity matrix were set to the values shown in the accompanying table; the bead intensity was defined on a linear scale of 0-255, the latter representing the intensity of the brightest beads. FIG. 18A shows the contribution of each ligand to the bead intensity. Due to the lower concentration of $L_1$, the intensity of Bead 1 is less compared to Bead 2, cross-reactivities are essentially undetectable.

Next, the system was perturbed with a third ligand, taking the concentration $L_3$ to be 1 pM and assuming that the new ligand has considerable amount of cross-reactivity with each of the receptors; $K_{3,1}=1\times10^{11}$/M, $K_{3,2}=1\times10^{10}$/M. Calculation of the fluorescent intensity of each bead in the presence of the third ligand yields the pattern in FIG. 18A which reveals an increase in the intensity of Bead 1 due to the third ligand, while leaving the intensity of Bead 2 unaffected due to the higher concentration of $L_2$ in the system and the lower affinity of $L_3$ to $R_2$. Thus, $L_3$ may be detected under the condition that it has a relatively high affinity to one of the receptors and is in significant amount compared to the competing ligand.

The evaluation of the coaffinity matrix (and comparison with theoretical modeling as disclosed herein) under conditions in which a mixture of ligands is permitted to interact with a multiplicity of receptors arranged in a random encoded bead array format provides a methodology to establish a characteristic feature set of cross-correlations in the mutual competitive binding affinities of multiple ligands and receptors. These co-affinities provide a robust means to characterize receptor-ligand binding equilibria by their affinity fingerprinting patterns. Deviations from well-defined reference cases also permit detection of "perturbing" ligands in solutions.

Example 14

Multiplexed Analysis of Reaction Kinetics

As illustrated in the foregoing examples, extensive washing generally is not required to discriminate beads from a background of solution fluorescence. Consequently, assay image sequences may be recorded in a homogeneous assay format to document the evolution of a binding reaction and to determine kinetic data for each of the binding reactions occurring.

Homogeneous binding assays may be performed in simple "sandwich" fluidic cartridges permitting optical microscopic imaging of the bead array and permitting the introduction of an analyte solution into a chamber containing a random encoded array of beads. More generally, the array also may be exposed to an analyte or other reaction mixtures under conditions of controlled injection of fluid aliquots or continuous flow of reactants or buffer. Using theoretical modeling, optimal combinations of relevant performance control parameters of this bead array reactor may be identified to minimize the time to equilibration or to maximize the portion of analyte captured by the array [K. Podual and M. Seul, TM KP-99/02]. Flow rate can be controlled by any of a number of available pumping mechanisms [M. Freemantle, C&EN, 77: 27-36].

TABLE

Figure 18B:
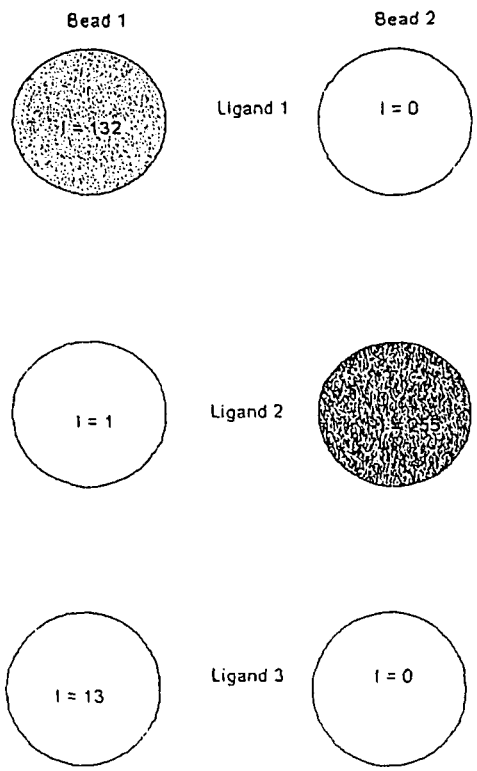

List of parameters used in simulations (FIG. 18)

| Parameter, units | Value |
|---|---|
| Initial Receptor Coverage $c_{R,0}$, moles/m$^2$ | $8 \times 10^{-9}$ |
| Vol Flow Rate, Q, μl/s | 1.0 |
| Diffusivity, D, cm$^2$/s | $1 \times 10^{-7}$ |
| ON-Rate, $k_{on}$/(M s) | $1 \times 10^5$ |
| Affinity Constant, $K_A$, /M | $1 \times 10^{11}$ |
| "Sandwich" Reactor Gap Size H, mm | 0.1 |
| Reactor Length, L, mm | 10 |
| Reactor Width, W, mm | 10 |

Figure 19:
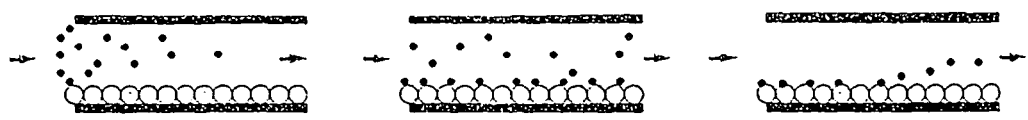
FIG. 19 is an illustration of numerical simulations of receptor-ligand association and disassociation kinetics.
Figure 19:
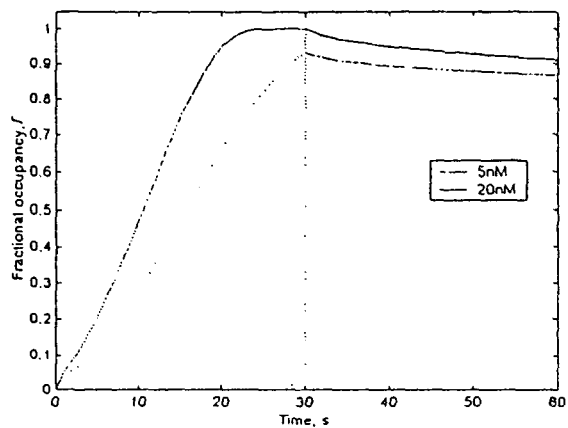

The analysis of image sequences permits kinetic data to be generated from which ON-rates and OFF-rates are determined with the aid of a theoretical model of the reaction-diffusion kinetics of the type illustrated in the foregoing example in FIG. 19. FIG. 19A displays stages in an adsorption-desorption cycle involving solution-borne analytes and a bead array immobilized at the bottom of a "sandwich" reaction chamber. The first panel depicts the initiation of the adsorption process; the second panel depicts the state of the reactor close to equilibrium when most of the beads have reached equilibrium; the last panel depicts the state of the reactor under the desorption cycle in which ligand-free fluid is injected and adsorbed molecules desorb from the bead surface. FIG. 19B displays the adsorption-desorption kinetics of a single receptor-single ligand system obtained by numerical solution of a reaction-diffusion system for a single type of receptor-ligand reaction; two cases of different concentrations of ligand are shown. Parameters used in the simulation are listed in the accompanying Table.

In contrast to prior art methods [D. G. Myszka, Curr. Opin. Biotechnol. 8: 50-57.], the present method relies on imaging and permits multiplexing. In addition, generalized models of the type introduced in Example 6 permit the analysis of complex binding kinetics for multiple simultaneous receptor-ligand interactions even in the presence of cross-reactions between multiple ligands and receptors.

The ability to monitor reaction kinetics in an array format will enable several approaches to enhancing the specificity of receptor-ligand or binding agent-analyte interactions in complex mixtures. For example, temperature programming may be invoked to enhance the specificity of DNA hybridization reactions. Similarly, the stringency of conditions applied to a hybridization reaction may be varied while the array response is being monitored; for example, hybridization may be conducted in a hybridization buffer under conditions leading to excess "non-specific" binding; specificity is enhanced by switching to a wash buffer of increasing stringency while monitoring the array response.

Example 15

Multi-Step Assay Sequences Using Encoded Arrays of Magnetic Particles

Methods and apparatus using biochemically functionalized super-paramagnetic particles for sample preparation in molecular and cellular biology and for a variety of enzyme-catalyzed on-bead reactions have been described ["Biomagnetic Techniques in Molecular Biology", Technical Handbook, 3$^{rd}$ Edition, 1998, Dynal, Oslo, NO]. These bead-based methods can be combined with the Random Encoded Array Detection format of the present invention to implement multi-step on-chip assay manipulations.

Figure 20:
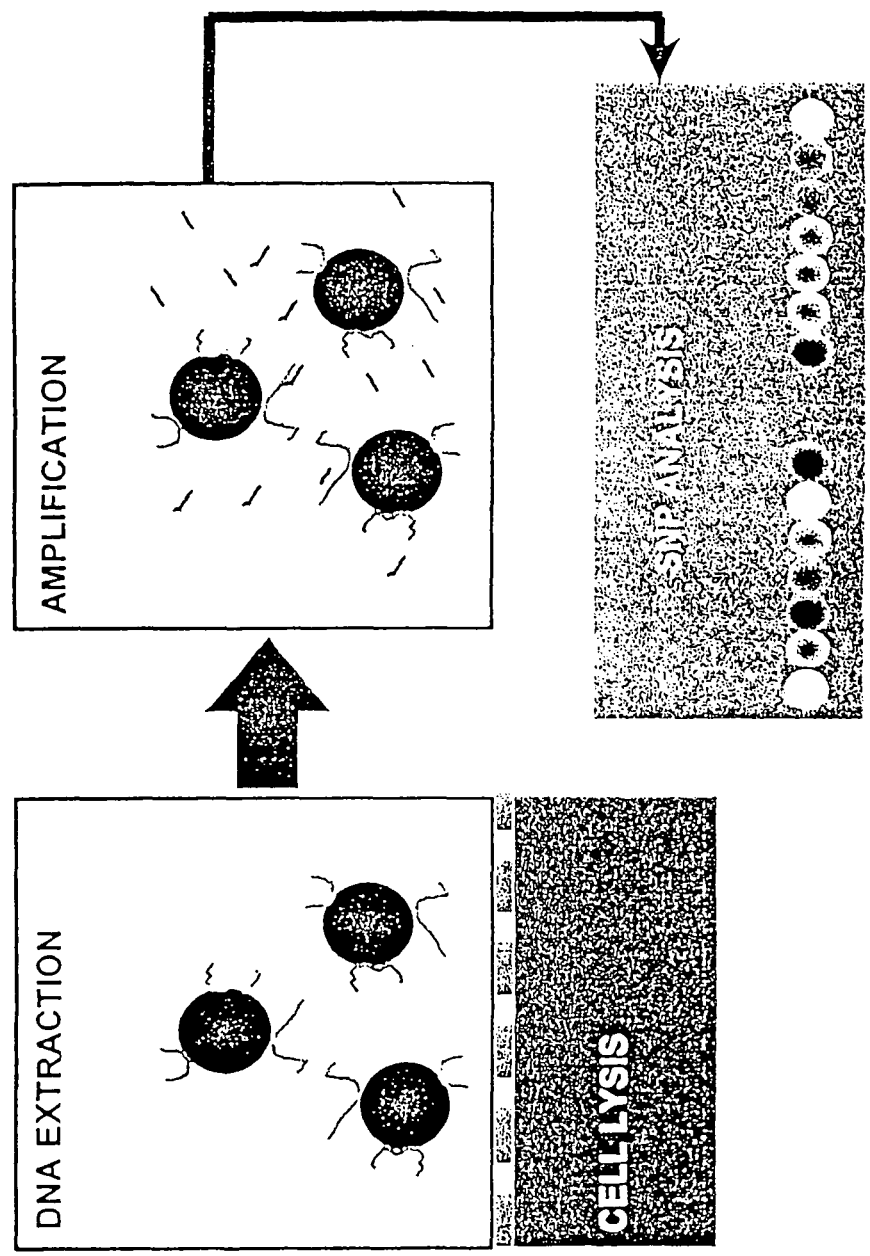
FIG. 20 is an illustration of integrated sample capture using magnetic capture beads and array-based detection using the random encoded array detection process of the invention.

For example, FIG. 20 illustrates the integration of a sequence of steps in a miniaturized format for multiplexed genotyping using a single chip with multiple compartments. First, cells are captured from a patient sample by affinity selection using functionalized magnetic beads, cells are lysed electrically or chemically in a first compartment, and genomic DNA is captured to the surface of a multiplicity of magnetic beads by non-specific binding; next, beads are collected by magnetic force into a second compartment which is in fluidic contact with the first compartment, within which the beads and DNA are washed with desired buffers; next, beads are further transferred to a location where PCR is performed using bead-coupled DNA as a template; multiple PCR strategies known in the art are available for this step (F. Fellmann, et. al., Biotechniques, 21:766-770); next, PCR products released into are captured by hybridization to a pre-assembled random encoded array displaying binding agents that are specific to different polymorphism targeted by the PCR amplification.

The use of encoded magnetic particles in conjunction with the optical programmability of LEAPS confers the ability to form reversibly immobilized arrays and to conduct programmable multi-step assay sequences under conditions in which beads are used in suspension when this is most favorable, for example to enhance reaction kinetics, and arrays are formed in real-time when this is most favorable, for example to provide a highly parallel format for imaging detection and assay read-out.

Figure 21:
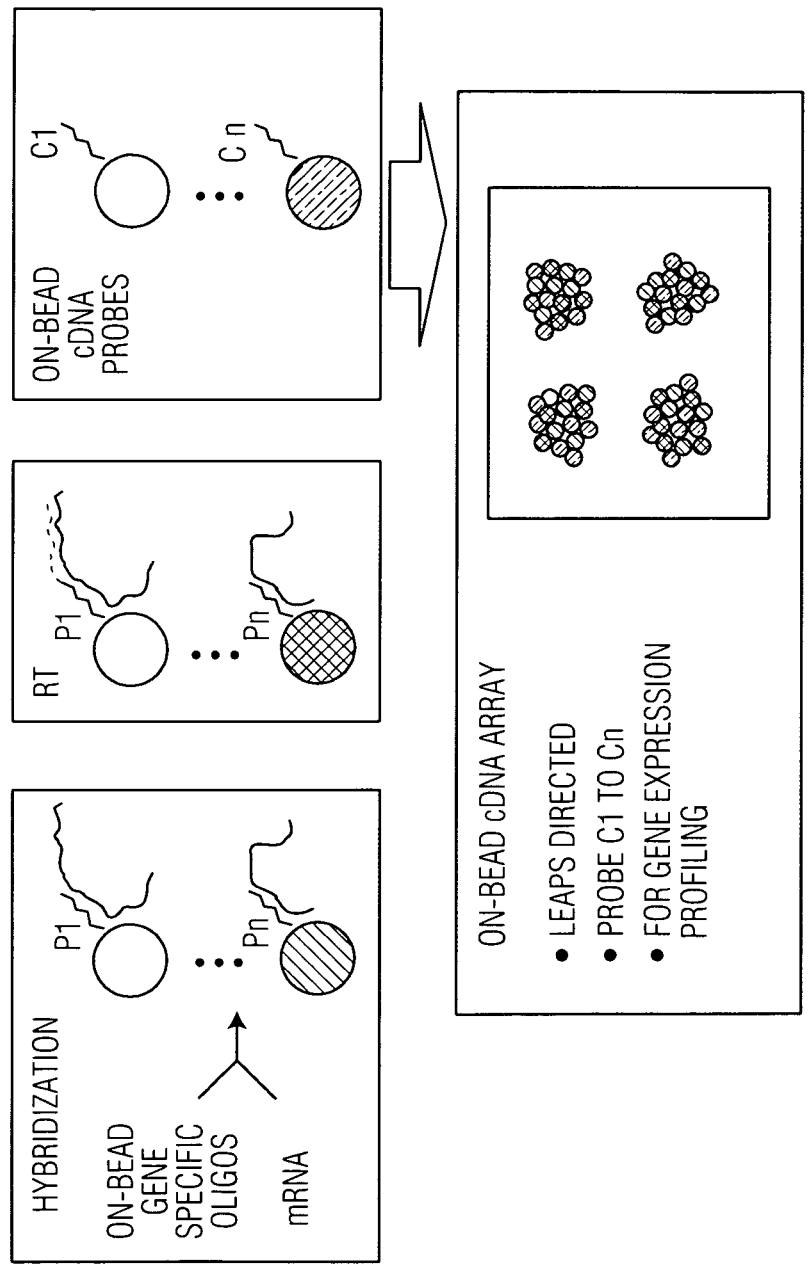
FIG. 21 is an illustration of multi-step assays using composite particles to integrate gene-specific capture, on-bead reverse transcription and post-assay array assembly.

For example, as illustrated in FIG. 21, the following sequence of steps could be integrated in a miniaturized format for the formation of a cDNA bead array. First, a pool of encoded magnetic beads, each bead type displaying a gene-specific probe, is introduced to an mRNA pool, and mRNA molecules are hybridized to their corresponding beads; next, on-bead reverse transcription (RT) is performed using bead-attached mRNA as template [E. Horenes, L. Korsnes, U.S. Pat. No. 5,759,820]; next mRNA is released from the beads; next beads are directed to the surface of a custom-designed chip and a cDNA bead array is formed using LEAPS. Such an array could serve to display binding agents in a gene profiling experiment using another set of mRNA as the target. Alternatively, the cDNA array could be analyzed for its own expression by applying a pool of labeled DNA binding agents to profile the genes of interest within the array.

Example 16

Synthesis of Super-Paramagnetic Iron Oxide γ-$Fe_2O_3$ (maghemite) Particles

The synthesis was carried out in reversed micellar solutions composed of the anionic surfactant, bis(2-ethylhexyl) sodium sulfosuccinate (AOT) and isooctane (Kommareddi et al., Chem. Mater. 1996, 8, 801-809) obtained from Aldrich Chemical Co., Milwaukee, Wis. Stock solutions of 0.5M AOT were used in preparing the reversed micellar solutions containing the reactants $FeSO_4$ (Sigma Chemical Co., St. Louis, Mo.) and $NH_4OH$ (Sigma Chemical Co., St. Louis, Mo.). Specifically, 0.45 ml of 0.9M $FeSO_4$ was added to 5 ml of 0.5M AOT in isooctane, separately 0.45 ml of $NH_4OH$ was added to 5 ml of 0.5M AOT in isooctane. The reaction was initiated by adding the $NH_4OH$ reversed micellar solution to the $FeSO_4$ reversed micellar solution under vigorous stirring. The reaction was allowed to proceed for ~2-3 hrs and then the solvent was evaporated at ~40° C. to obtain a dry surfactant iron oxide composite. This composite was re-dispersed in the organic solvent of choice to give a deep red colored transparent solution.

Example 16a

Synthesis of Magnetic Nanoparticles with a Functional Site

This Example illustrates the creation of a functional site on a magnetic nanoparticle. A surfactant was dissolved in oil to obtain a reverse micellar solution which was used to synthesize the magnetic nanoparticles of Example 16. The resulting reaction mixture was dried to obtain a dry surfactant past which was re-dispersed in an oil of choice. An aqueous solution of monomer(s) and or preformed polymer(s), a cross-linking agent and initiator were added. The mixture was subjected to a polymerization step, and the polymerized reaction product was dried. The dried mass was dispersed in aqueous buffer; and the methods can be combined with READ to implement multi-step on-chip assay manipulations.

Example 16b

Coupling of a Biomolecules

This Example illustrates the coupling of a biomolecule to the magnetic nanoparticles of the invention. The magnetic nanoparticle of Example 16a can be further functionalized to perform an assay fo interest by binding to the functional site on the magnetic nanoparticle certain molecules such as for example DNA (oligonucleotides) or RNA fragments, peptides or proteins, aptamers and small organic molecules. The binding of such molecules can be performed using processes known in the art, for example, using one or several coupling reactions (See, e,g, G. T. Hermanson, Bioconjugate Techniques (Academic Press, 1996); L. Illum, P. D. E. Jones, Methods in Enzymology 112, 67-84 (1985)). Attachment of the molecule of interest to the functional site generally requires a one-step or two-step reaction which can be performed in parallel using standard liquid handling robotics and a 96-well format to covalently attach any of molecules to the functional site on the magnetic nanoparticle.

Specifically, this Example illustrates a method of attaching a probe (for example a protein), to the functional site of a magnetic nanoparticle of the invention, using well-established carbodiimide chemistry. In a 2 ml vial an aliquot containing 10 mg of carboxylate functionalized magnetic nanoparticle was mixed with 1 ml 10 mM borate buffer (pH=8.5). The resulting particles were then separated magnetically using a permanent magnet separator and the supernatant was siphoned off. The separated pellet was washed two times (using the same protocol as above) in 0.1M MES buffer (pH=4.5) and finally re-suspended in 600 µl of the same. In a separate vial 3 mg of Neutravidin (a biotin binding protein, Pierce Chemicals, Rockford, Ill.) was dissolved in 300 µl of the MES buffer and the solution was slowly added to the suspension of the magnetic charged particle. The suspension is sonicated using a probe sonicator. Following sonication, EDAC (1-ethyl-3-(3-dimethylaminopropyl)-carbodiimide) (Aldrich-Sigma, Milwaukee, Wis.) solution (200 mg/ml) was added. The mixture was allowed to react for 2 hours at room temperature, following which the resulting magnetic nanoparticles were magnetically separated, washed one time with a coupling buffer, two times in a borate buffer and resuspended and stored in a storage buffer (PBS pH=7.4, 0.1% (w/v) BSA, 0.5% (w/v) Tween 20, 10 mM EDTA and 0.02% (w/v) $NaN_3$) at 2-8° C.

Example 16c

Preparation of Composite Particles

This Example illustrates the production of encoded magnetic articles. Encoded particles were reacted with the magnetic nanoparticles of Example 16b. In a more general embodiment, super-paramagnetic polymer nanoparticles may also be used (such as those obtained from MACS microbeads, Miletnyi Biotech Inc, Auburn, Calif.; Captivate ferrofluid particles, Molecular Probes, Eugene, Oreg.; Nanomag particles, Micromod, Rostock, Germany).

Figure 23:
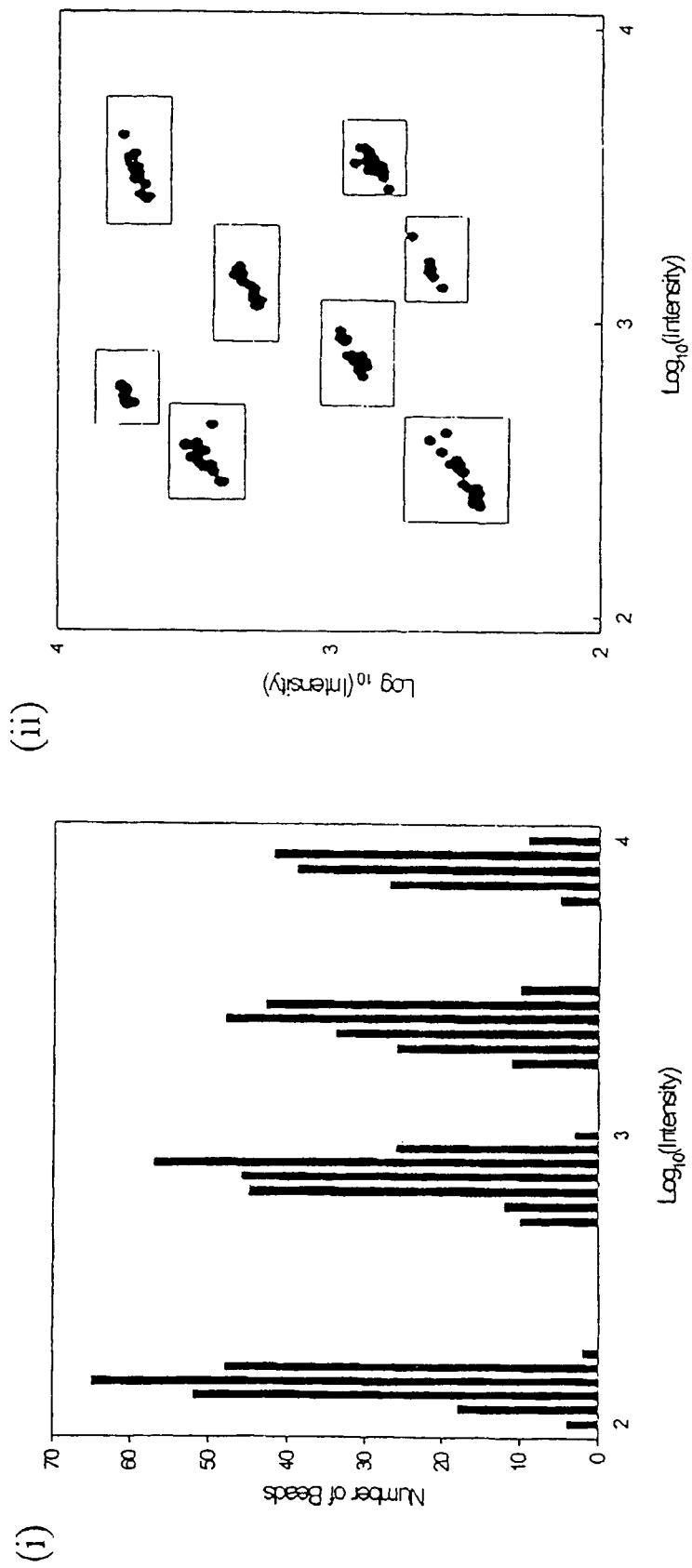
FIG. 23($i$) is a histogram showing four different types of single optically particles and FIG. 23($ii$) is a dot plot of eight dual encoded particles.

FIG. 23 illustrates a sub-library of 12 types of encoded magnetic particles. The encoded particles were synthesized using 3.2 µm diameter cross-linked polystyrene particles with tosyl surface groups (Bangs Labs, Fishers, Ind.) and two hydrophobic pyrromethane dyes which were each introduced by swelling and bulk staining. The dyes were individually introduced to obtain four intensity levels, and were mixed in four nominal molar ratios. Following, 100 µl of a 1% solution of the colored Latex (in PBS) was mixed with 100 µl or 200 µl of Captivate ferrofluid (streptavidin conjugate, 200 nm diameter, used as supplied) (Molecular Probes, Eugene, Oreg.) or 100 µl of Nanomag dextran coated. Streptavidin functionalized magnetite particles 130 nm diameter were used as supplied) (Nanomag particles, Micromod, Rostock, Germany). The whole reaction volume is made up to 500 µl using phosphate buffer pH 7.8 and the coupling reaction is allowed to proceed overnight. The resulting particles are separated magnetically washed 1×, resuspended and stored instorage buffer (PBS pH=7.4, 0.1% (w/v) BSA, 0.5% (w/v) Tween 20, 10 mM EDTA and 0.02% (w/v) $NaN_3$) at 2-8° C.

Example 16d

Controlling the Content of Metal Oxide

This Example illustrates the method by which the content of the metal oxide can be controlled to impart on the magnetic moment of the encoded magnetic particle of the invention. This can be accomplished by varying the number of magnetic nanoparticles which can bind to the surface of the encoded particle For ease of monitoring, and by way of illustration, instead of magnetic nanoparticles, Fluoronanogold, a fluorescein-gold nanoparticle—streptavidin conjugate (supplied from Nanoprobes, Yaphank, N.Y.) was used to monitor the number of particles. The reagent contained ~0.08 mg/ml of streptavidin and was used as received.

Figure 24:
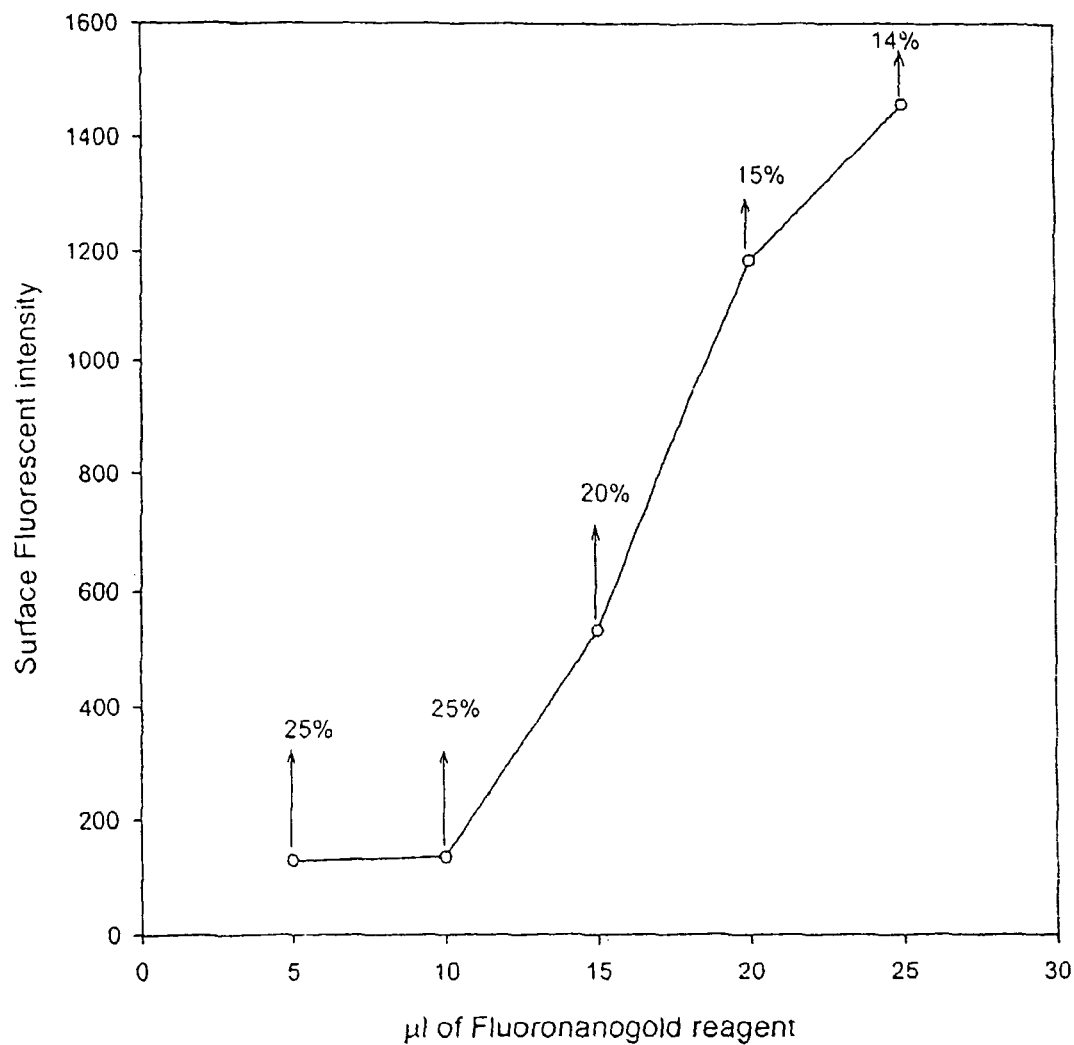
FIG. 24 is an illustration of the variation of magnetic loading.

In this Example, 0.5 mg of biotin functionalized 3.36 µm diameter polystyrene beads (Spherotech, Libertyville, Ill.) was suspended in 500 µl of 20 mM phosphate buffered saline (150 mM) at pH 7.4 with 0.1% BSA. Varying amounts of Fluoronanogold reagent were added to the bead solution and the streptavidin-biotin binding reaction allowed to proceed for 1 hour at room temperature, following which the microparticles were separated by centrifugation and supernatant removed. FIG. 24 shows the fluorescence intensity from the particles bound on the surface as a function of the amount of Fluoronanogold reagent added.

Example 17

Synthesis of Fluorescently Colored and Magnetic Polymer Bead Composites

A stock solution of hydrophobic fluorescent dye and the iron oxide particles was made by re-dispersing the dried magnetic composite and the dye in the solvent of choice, for example a $CHCl_3$ (Aldrich Chemical Co., Milwaukee, Wis.) or $CH_2Cl_2/CH_3OH$ mixture (70/30 (v/v)) (Aldrich Chemical Co., Milwaukee, Wis.). A predetermined amount of polymer beads was washed thoroughly in methanol (3×) and then evaporated dry. Simultaneous incorporation of the fluorescent dye and the iron oxide nanoparticle was achieved by swelling the beads in organic solvent/nanoparticle/dye mixture. The swelling process was completed within ~1 hr. Following this the polymer beads were separated by centrifugation and washed with methanol (3×) followed by isooctane (2×) and then methanol (2×) and finally redispersed in 0.2% SDS-DI water solution.

Example 18

Formation of Arrays by Application of a Magnetic Field

The composite particles of the invention when exposed to a homogeneous axial magnetic field (oriented normal to the substrate plane), can be arranged in 2D array format. As a function of increasing magnetic field strength which is dependent on the paramagnetic susceptibility of the composite particle, planar assemblies can be formed. Permanent magnets can be designed so as to produce the field strength required to realize the desired configuration of the assembly. Requisite magnetic field configurations can also be produced by an electromagnet in solenoid or Helmholtz configuration known to the art; the substrate can be introduced into the magnet bore or can be placed in immediate proximity to the coil(s) outside of the bore so as to ensure the orientation of the field substantially normal to the substrate plane. Spatially modulated magnetic fields can be produced by patterning the substrate with perm-alloy using methods known to the art.

In this Example, three differently sized composite particles with wherein the encoded particles are 3.2 microns, 6.9 microns and 10.9 microns were synthesized as described herein, as expected, the magnetization of the composite particles increased with increasing particle size.

Figure 25:
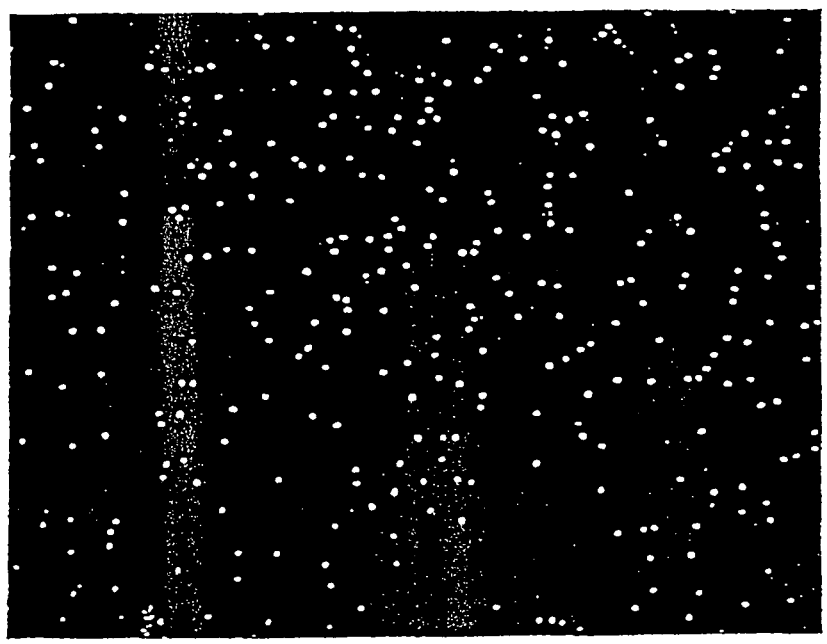
FIG. 25 is an illustration the composite particles of the invention exposed to a magnetic field.

FIG. 25 shows a 2D geometry of 3.2 microns composite particle exposed to a magnetic field of approximately 1000 Gauss produced using a permanent magnet.

Example 19

Two-Dimensional Colloidal Arrays: Formation of Magnetic "Wigner" Crystals

Figure 26:
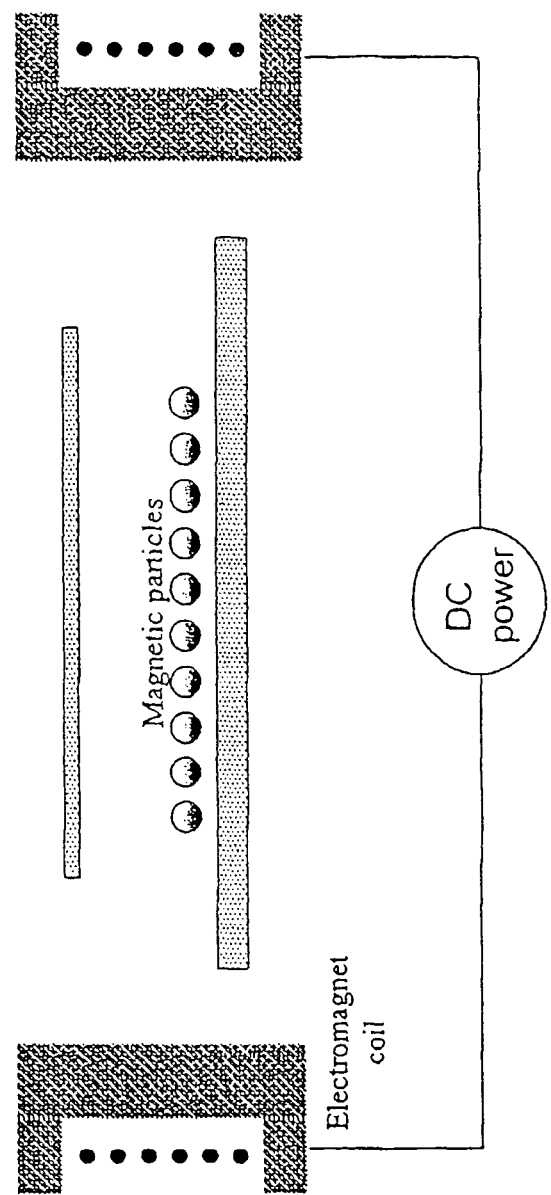
FIG. 26 is a schematic illustration of the experimental assembly for application of a magnetic field.
Figure 27:
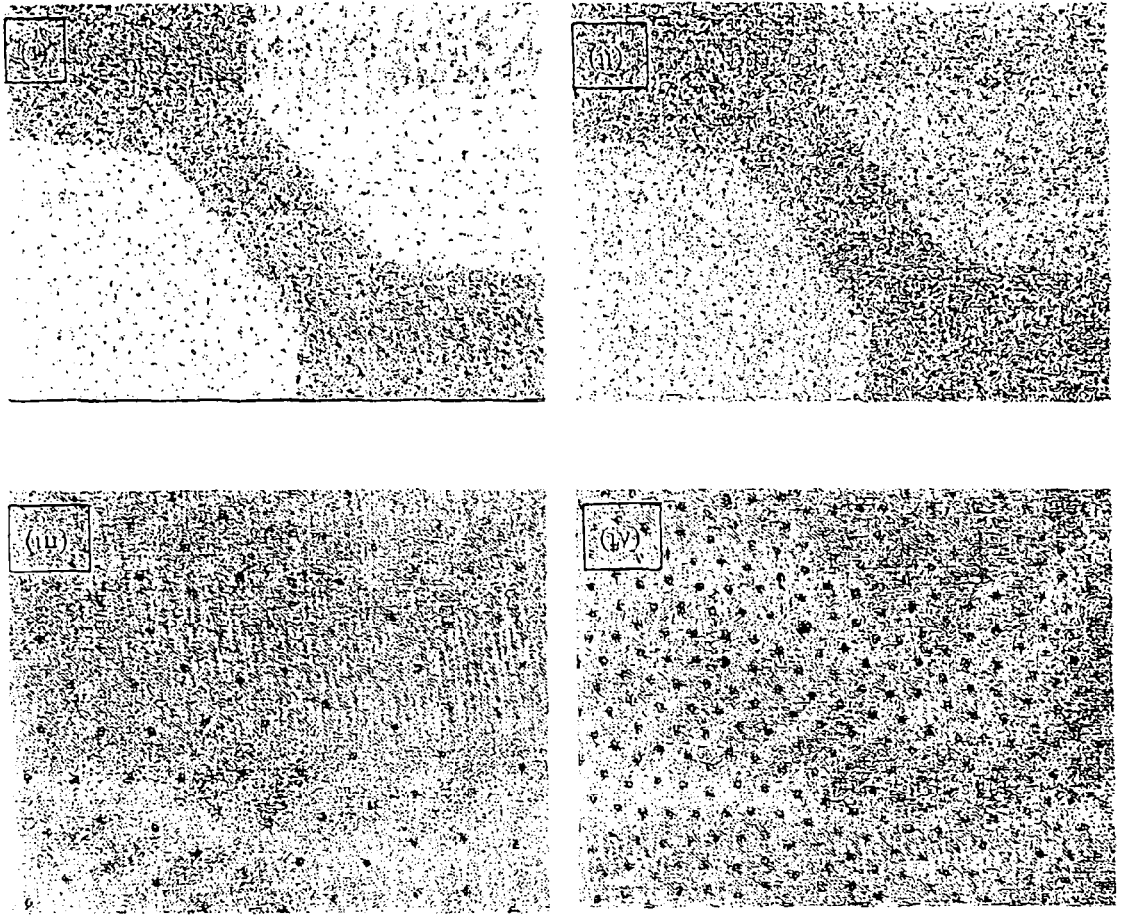
FIG. 27($i$) is a schematic illustration of the 2D structure of the bead assembly before application of a magnetic field.

This Example illustrates the ability to manipulate the composite particles of the invention. Exemplification is provided by the manipulation of superparamagnetic particles suspension such as superparamagnetic $Oligo(dT)_{25}$ microparticle (Dynal, Lake Success, N.Y.). Suspension of these particles are formed by mixing the particle at a concentration of ~5× $10^7$ beads/ml) in 0.01 M saline, containing 0.05% triton-X100 (Sigma-Aldrich, Milwaukee, Wis.) as a stabilizer. The magnetization of the particles is completely reversible and, at low field strengths, is proportional to the external field through the effective volumetric magnetic susceptibilty (=0.192). The suspensions are held on a microscope stage in a sandwich cell formed by a silicon electrode and an ITO coated glass electrode separated by an adhesive spacer ~100 µm thick. A nominally uniform magnetic field is generated in the sample by a coil of copper-wire placed underneath the sandwich cell. After application of the magnetic field the evolution of the suspension structure is recorded with a CCD camera attached to a VCR and the images digitized for farther analysis. FIG. 26 shows the experimental setup and FIG. 27 shows a series of snapshots illustrating the formation of 2-dimensional magnetic arrays.

When a magnetic field is applied, the particles acquire magnetic moments $m=4/3\pi a^3 \mu_o \chi H$, where a is the particle radius, $\mu_o$ the magnetic permeability of vacuum, and H is the external field.

Example 20

Streptavidin-Biotin Binding Assay Using Fluorescent Magnetic Microparticles

Figure 28:
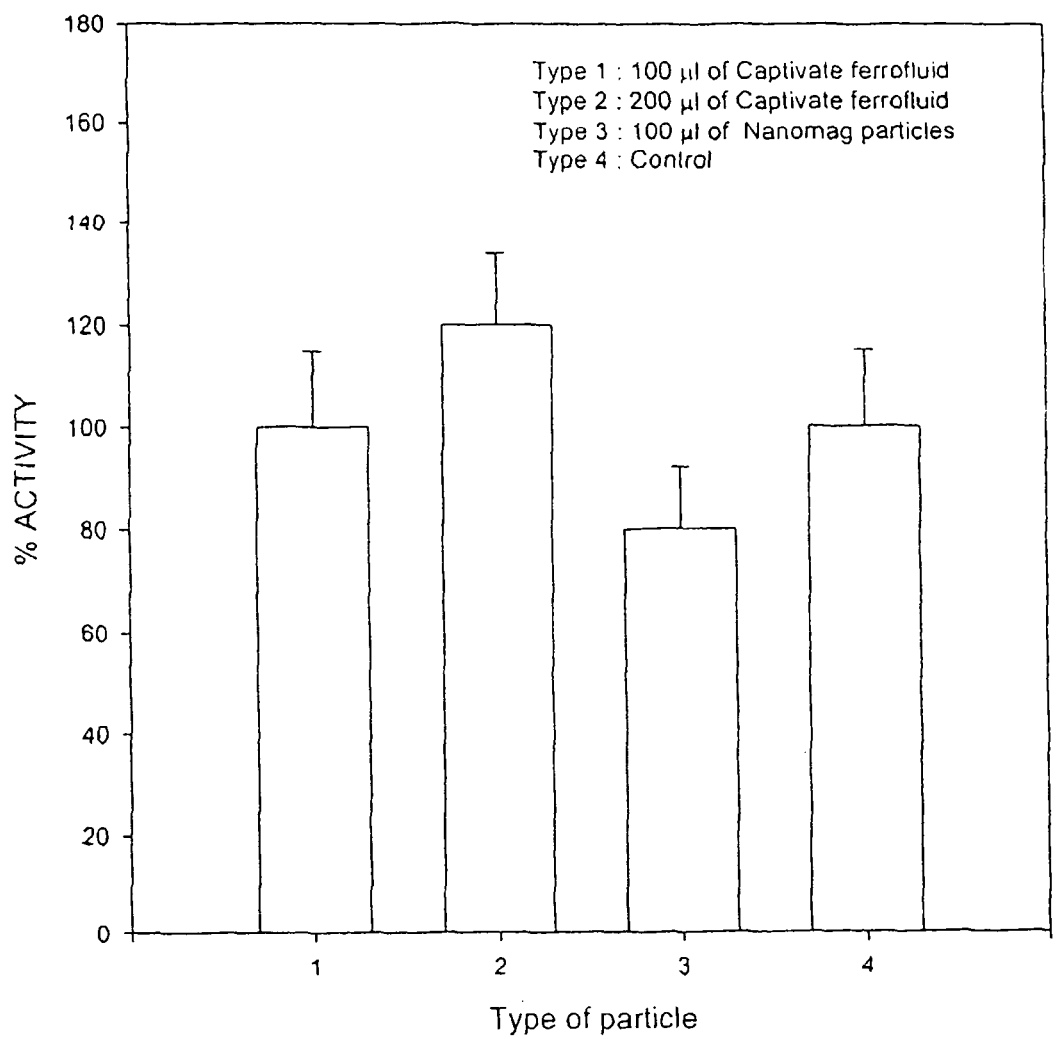
FIG. 28 shows results of a streptavidin-biotin binding assay using the encoded and magnetic particles of the invention.

In this Example, to 100 µl of a suspension of the composite particles of the invention, which have been functionalized with neutravidin as described in Example 16c (1%) solids is added to a 1.5 ml vial and the suspension diluted with 900 µl of PBS with 0.01% (w/v) of Tween-20 (PBST). The composite particles of the invention are mixed by vortexing and then separated magnetically and the supernatant aspirated off. The pellet is resuspended in 980 µl of PBS. 20 µl of a biotin-Oligo $(dT)_5$-CY5.5 (IDT, Coralville, Iowa) at a concentration (26.7 ng/ml). The mixture is incubated for 30 minutes at room temperature. Following this the particles of the invention are separated magnetically and washed 2× in PBST and resuspended in 1 ml of PBST. The particles of the invention are then assembled on a chip and their surface fluorescence estimated using the method previously described. The results are shown in FIG. 28. For purposes of comparison, the encoded particles of the invention in the absence of the magnetic nanoparticles of the invention, but having covalently attached thereon neutravidin were also reacted to the biotinylated probe using the procedure described in this Example.

Example 21

On-Chip Hybridization of Target Molecules

This Example relates to on-chip hybridization of target molecules to oligonucleotides probes immobilized to the composite particles of the invention. Biotinylated oligonucleotides with known base sequence were first coupled to a given type of color-coded composite particles that have been previously coated with Neutravidin on the surface. The coupling reaction was carried out in 0.1 ml coupling buffer (150 mM NaCl, 0.05 mM ethyenediamine tetra-acetic acid (EDTA), 0.5% bovine serum albumin, 0.5 mM Tris-HCl, and 100 mM sodium phosphate, pH 7.2) with 0.4 µM biotinylated oligonucleotides, and approximately $6.7 \times 10^5$ particles. The coupling reaction mix was incubated at room temperature for 30 min with vortexing. Upon completion of the coupling reaction, the particles were collected by centrifugation. The unreacted sites of the NeutriAvidin on the surface were blocked by using 0.1% biotin in 150 nM NaCl and 100 mM sodium phosphate, pH 7.2 with 0.05% Tween-20. The blocking was carried out at room temperature for 20 min with vortexing. After blocking, the particles were washed with 0.2 ml of 150 mM NaCl and 100 mM sodium phosphate, pH 7.2 with 0.05% Tween-20. The foregoing procedure can be utilized to couple any biotinylated oligonucleotides of interest to different types of Neutravidin-coated particles of the invention.

Figure 29:
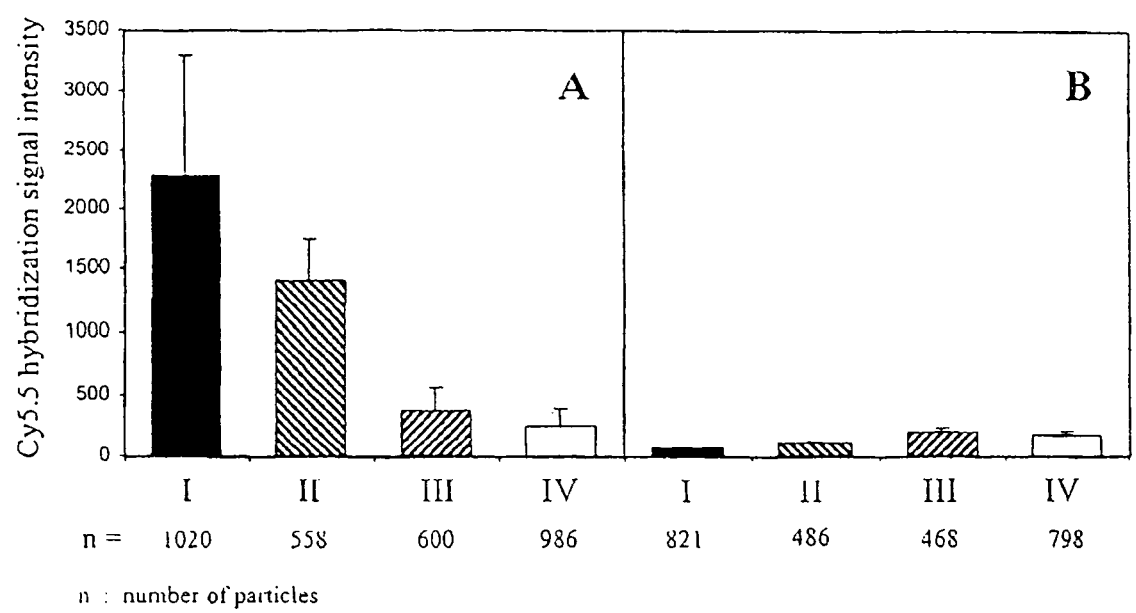
FIG. 29 shows results of a hybridization assay using the encoded and magnetic particles of the invention.

Several types of color-encoded particles of the invention were coupled with biotinylated oligonucleotides with known sequences and were combined into one tube for assembly of arrays on silicon chips. The arrays thus formed were then used for on-chip hybridization of peptide nucleic acid (PNA) oligomers to specific complimentary oligonucleotides previously coupled to the micro particles of the invention. Specifically, hybridization was carried out in 30 µl hybridization solution (90 mM NaCl, 83 mM guanidine thiocyanate, 8 mM $MgCl_2$, 17 nM EDTA, 0.02% biotin, 0.1% Tween-20, 70 mM mM Tris-HCl, pH 7.5,) with 218 nM biotinylated PNA oligomers. The arrays in the hybridization mix were incubated at 40° C. for 60 min. Upon completion of hybridization, the arrays were washed with 50 µl of 250 mM NaCl, 10 mM Tris-HCl, pH 7.5, 0.1% Tween-20, at room temperature for 10 min. For detection of the biotinylated PNA oligomers that were hybridized on the composite particles of the invention, the arrays were incubated with Cy5.5-conjugated Streptavidin (18 µg/ml) in 150 mM NaCl and 100 mM sodium phosphate, pH 7.2, at room temperature for 30 min. After washing with 15 mM NaCl, 10 mM Tris-HCl, pH7.5, the arrays were examined by using a fluorescence microscope. Fluorescence emitted from the particles of the invention and the Cy5.5-labeled PNA oligomers were determined by using optical filters with specific wavelengths. The particles of the invention were decoded according to their color codes, and Cy5.5 fluorescence emitted from specific particles was evaluated by using a computer program (READ). Color-encoded particles devoid of magnetic character were used as controls in the assay. Results of the assay are shown in FIG. 29 demonstrate that PNAs specifically hybridize to complimentary oligonucleotides coupled on the composite particles. Fluorescence signal intensity was determined from four types of the particles of the invention (I, II, III and IV) from two arrays (Chip A and B, for panels A and B, respectively) in the on-chip hybridization assay. The type I particles are the composite particles of the invention, whereas Types II, III and IV are three different types of the encoded particles of the invention. Types I and II are functionalized encoded particles with biotinylated oligonucleotides that are complementary to the PNA oligomers. Type III encoded particles are functionalized with an oligonucleotide with unrelated base sequence to the PNA. Type IV encoded particles have no oligonucleotides on their surface. Chip B serves as a negative control for chip A, which was incubated with the hybridization mixture but without the target PNA. The symbol "n" denotes the number of particles on each type and the bars represent standard deviation of the mean.

Example 22

Immunoassay Using Fluorescent Magnetic Microparticles

In this Example, the composite particles of the invention are used for carrying-out immunoassays. The composite particles of the invention can be customized to display antibody of interest on their surface. An array of composite particles of the invention can be exposed to the sample solution (such as serum solution) containing antigens of interest. Subsequent addition of fluorescently labeled secondary antibodies results in the formation of ternary fluorescent complex the concentration of which can be monitored by recording the fluorescence from the composite particle surface using methods disclosed in this invention. Arrays of the antibody functionalized composite particles of the invention can thus be used for monitoring serum protein levels, and the binding pattern of the antigens of interest may be useful in protein profiling.

Example 23

Alternative I: Magnetic Field-Induced Array Formation

This Example illustrates the operation of FIG. 22 and a sequence of reaction steps leading from the sequence-specific capture of mRNA molecules to the formation of a EFM bead-displayed cDNA array. Such an array will be useful in many applications. For example, in gene profiling, a planar cDNA array will be useful to profile mRNA concentrations; alternatively, the cDNA array can be probed directly using a pool of labeled DNA binding agents or probes to profile the genes of interest within the array. The protocol, performed in a temperature controlled device, comprises the following steps: (1) introducing a set of the composite particle of the invention into a first compartment containing a pool of mRNA molecules, each particle type displaying a gene-specific oligonucleotide probe; mRNA molecules are permitted to anneal to their corresponding probes. Assay conditions for this capture step are known in the and are applicable herein; (2) perform on-particle reverse transcription (RT) using particle-attached mRNA as template and release mRNA from the particles; (3) applying magnetic field from permanent magnet and wash while retaining the particles; (4) releasing the magnetic field and re-suspending the particles in buffer to perform the process of LEAPS; (5) direct the particles to a compartment containing custom-designed chips and form a planar array of the composite particles of the invention using LEAPS.

Example 24

Alternative II: Magnetic Field-Induced Array Formation

This Example illustrates the operation of FIG. 22 and a sequence of reaction steps leading from the sequence-specific capture of mRNA molecules to the formation of a EFM particle-displayed cDNA array. The protocol set forth in Example 21 is used except that a planar array of the composite particles of the invention by applying a magnetic field to is formed using the application of a magnetic field and steps (4) and (5) of Example 21 are omitted.

Example 25

Multistep Assay Sequence Using Arrays of Encoded Magnetic Beads

This Example illustrates a multi-step biochemical reaction protocol which integrates the capture of genomic DNA fragments to a first set of magnetic nanoparticles, followed by magnetic separation and solid-phase amplification of captured "particle-tagged" fragments according to the general process described in FIG. 22. This capture step is followed by a transformation step of concurrent "multiplex" PCR amplification reactions, each reaction containing a small set of primer pairs to produce solution-borne amplicons. These are pooled and placed into contact with a set of the composite particles of the invention for multiplexed analysis invoking post-transformation mediated by application of a magnetic field.

The foregoing can be accomplished by the following steps:
1. Sample Capture and First Transformation Given a solution containing fragments of genomic DNA, divide into four equal parts, aliquots are injected into four separate reaction compartments, equipped to permit temperature and control in accordance with standard PCR temperature cycling protocols. Into each compartment, one or more magnetic nanoparticles-tagged primers are injected. A particle-tagged primer is composed of magnetic nanoparticles displaying an oligonucleotide probe directed against a genomic DNA target fragment of interest, said probe also serving as a first primer of a subsequent polymerase-catalyzed primer extension reaction. The next step permits capture by hybridization of selected fragments to matching particle-displayed probes, said targets serving as templates in subsequent extension reaction. To each compartment, polymerase is added and one or more second primers as needed to permit template-directed extension of particle-coupled capture probes under temperature cycling concurrently in all compartments, thereby producing first extension products, anchored to the magnetic nanoparticles. A magnetic field is applied to form a planar array of magnetic nanoparticles in each compartment. The compartments are washed while retaining particle—anchored extension products A typical PCR protocol using particle-tagged primers to amplify a fragment of genomic DNA is as follows. An oligonucleotide probe corresponding to a specific target position within the fragment of interest is designed with variable 3' terminus aligned at or near the target position. Probes are synthesized to contain a 5' biotin-TEG with a 12 C spacer (Synthegen TX). Probes are attached to streptavidin-coated magnetic beads in accordance with standard reaction protocols such as the following: add to a magnetic bead suspension in 1× TE (100 mM Tris-HCl, 10 mM EDTA), 500 mM NaCl for 45 minutes at room temperature; wash beads with 1× TE, 150 mM of NaCl for 3×; and suspend in 50 µl of same solution. Next, add 1 µl of each bead suspension to to PCR mix containing 1× buffer (100 mM Tris-HCl, pH. 9.0, 1.5 mM Magnesium Chloride, 500 mM KCL), 40 µM Cy5-labeled dCTP (Amersham Pharmacia Biotech NJ), and 80 µM of the remaining three dNTPs, and 3 units of Taq DNA polymerase (Amersham Pharmacia Biotech NJ). Genomic DNA target fragments (40 ng) are added to the PCR mix just prior to initiating extension. Under these conditions, ten cycles of amplification suffice to produce sufficient bead-anchored extension product using a Perk-in Elmer 9600 thermal cycler, a temperature cycle consisting of denaturation (30 s at 90 C), annealing (30 s at 55 C), and extension (20 s at 72 C). Following completion of the extension reaction, beads typically are washed four times by centrifugation in 1× TE buffer.
2. Concurrent Instances of Second Amplification To each reaction compartment, polymerase was injected along with a set of one or more primer pairs designed to select regions within particle-anchored first extension products, each compartment receiving a unique set of such primer pairs concurrent amplification of bead-anchored fragments under temperature cycling is allowed to occur, thereby producing, in each compartment, a set of specific amplicons as directed by the corresponding primer sets admitted into the compartment. Standard PCR reaction protocols (REF) apply to this step.
3. Pooling of Reaction Products, Post-Assay Array Assembly and Detection Solutions containing amplicons are combined to produce analyte solution and transfer to a detection compartment and placed into contact with a set of the encoded and magnetic nanoparticles of the invention, each particle displaying a sequence-specific oligonucleotide probe uniquely directed against one of the amplicons within the analyte solution. Annealing of amplicons to bead-displayed probes to form hybridization complexes is permitted to occur, and analysis of selected regions of target sequence by method of choice, e.g., differential thermal stability of hybridization complexes or probe elongation is performed. A magnetic field is applied to form planar array of the particles of the invention. An assay image signal is recorded. A decoding image is recorded to permit decoding of capture probe identities Standard assay conditions for polymorphismrhism analysis apply to this step, providing also conditions permitting formation of planar arrays of encoded functionalized magnetic beads, such conditions being illustrated herein in connection with Example NN and Figure MM (SB: EFM bead array, induced by permanent magnet.)

Example 26

Mixed Clusters and Arrays

This Example illustrates an assay format wherein target DNA strands are attached to magnetic nanoparticles of the invention. Chemical attachment is readily accomplished using standard protocols of bioconjugate chemistry as known in the art. For example, strands of DNA are readily biotinylated and may then be attached to streptavidin-coated magnetic nanoparticles. Alternatively, particle-displayed DNA strands are produced by PCR using bead-tagged primers, as discussed in Example 21. The requisite set of encoded particles of the invention are produced by the methods provided herein. The particles are functionalized with specific oligonucleotide probes using standard methods of bio-conjugate chemistry as know in the art. In the course of the assay, hetero-structures composed of magnetic nanoparticles and encoded particles are formed as a result of the formation of a complex between binding partners, and these complexes are assembled into a planar array for detection.

Two alternatives are set forth herein. In the first alternative, the size of the optically encoded beads will typically significantly exceed that of the magnetic beads, a typical ratio of respective radii being 100:1; streptavidin-coated magnetic nanoparticles of 100 Å diameter are commercially available, as herein discussed in connection with Example 22. Next, a mixture of magnetic bead-displayed DNA target strands is combined with a set of color-encoded beads displaying oligonucleotide probes under conditions permitting hybridization of matching magnetic bead-tagged target targets to probes. Formation of hybridization complexes will "decorate" each color-encoded bead with a large number of magnetic nanoparticles to produce a magnetic shell, resulting in the formation of a particle of the structure and composition discussed herein.

Application of a magnetic field in accordance with the methods of the present invention, will then produce a planar array of the encoded and magnetic nanoparticles of the invention to permit recording of a multicolor fluorescence image to identify captured DNA targets. Alternatively, assay conditions may be chosen so as to favor the formation of clusters. That is, the magnetic nanoparticles of the invention acting as multi-dentate "ligands", mediate "agglutination" of the encoded particles of the invention into a cluster of the encoded and magnetic of particles of the invention. Application of a strong magnetic field, typically producing magnetization in excess of 1000 Gauss, permits separation of these clusters from solution into a an expanded assembly of isolated clusters.

In a second alternative, the roles, and hence the relative sizes, of magnetic and encoded particles of the invention are reversed so that larger magnetic nanoparticles are decorated by the encoded particles Application of a magnetic field in accordance with the conditions set forth in Example 19, (Dynal beads—solenoid) herein produces a planar array of magnetic nanoparticles wherein each particle will display an optical signal or not display an optical signal depending on whether the particle have been endowed with an optical identifier.

Both alternatives in this Example require reading of multi-optical signatures to identify captured targets. When particle optical loading encoding is achieved by application of a small number of encoding colors, typically two or three, and variation of the ratio of such encoding colors in accordance with standard methods as known in the art, multicolor imaging is readily achieved by standard multicolor fluorescence imaging using multiple filter sets as known in the art. Otherwise, if combinations of multiple distinct colors are used to produce the color code, then methods of multi-spectral imaging are generally available to record the assay image.

We claim:

1. A method of forming an array, comprising:
   providing a plurality of magnetic particles comprising at least two different particle populations, each bearing a different binding agent and being distinguishable by an optically differentiable code associated therewith, suspended in a fluid;
   contacting the magnetic particles with analytes in solution under conditions permitting the binding agents to bind to analytes in an analyte-specific manner;
   assembling the magnetic particles, following said contacting and binding to analytes, in a planar array on one or more chips using a magnetic field; and then forming a gel film on the surface of the chips and immobilizing the magnetic particles on the chips by embedding them in the gel film.

2. The method of claim 1 wherein the particles are randomly placed in the array.

3. The method of claim 1 wherein a plurality of arrays are assembled on a plurality of chips.

4. The method of claim 2 wherein the chips include microwells patterned on the chips.

5. The method of claim 1 wherein the gel film is a polymer.